United States Patent
Xavier et al.

(10) Patent No.: US 12,374,423 B2
(45) Date of Patent: Jul. 29, 2025

(54) SYSTEMS AND METHODS FOR MHC CLASS II EPITOPE PREDICTION

(71) Applicants: THE BROAD INSTITUTE, INC., Cambridge, MA (US); THE GENERAL HOSPITAL CORPORATION, Boston, MA (US)

(72) Inventors: Ramnik Xavier, Boston, MA (US); Daniel B. Graham, Cambridge, MA (US); Chengwei Luo, Cambridge, MA (US)

(73) Assignees: THE BROAD INSTITUTE, INC, Cambridge, MA (US); THE GENERAL HOSPTIAL CORPORATION, Boston, MA (US)

( * ) Notice: Subject to any disclaimer, the term of this patent is extended or adjusted under 35 U.S.C. 154(b) by 1447 days.

(21) Appl. No.: 16/627,193

(22) PCT Filed: Jun. 27, 2018

(86) PCT No.: PCT/US2018/039843
§ 371 (c)(1),
(2) Date: Dec. 27, 2019

(87) PCT Pub. No.: WO2019/006022
PCT Pub. Date: Jan. 3, 2019

(65) Prior Publication Data
US 2022/0293215 A1  Sep. 15, 2022

Related U.S. Application Data

(60) Provisional application No. 62/525,673, filed on Jun. 27, 2017.

(51) Int. Cl.
| | |
|---|---|
| *G16B 20/30* | (2019.01) |
| *A61K 39/00* | (2006.01) |
| *A61K 39/02* | (2006.01) |
| *C07K 14/195* | (2006.01) |
| *G16B 15/30* | (2019.01) |
| *G16B 35/20* | (2019.01) |
| *G16B 40/20* | (2019.01) |

(52) U.S. Cl.
CPC .......... *G16B 20/30* (2019.02); *A61K 39/0208* (2013.01); *C07K 14/195* (2013.01); *G16B 15/30* (2019.02); *G16B 35/20* (2019.02); *G16B 40/20* (2019.02); *A61K 2039/57* (2013.01); *A61K 2039/605* (2013.01)

(58) Field of Classification Search
None
See application file for complete search history.

(56) References Cited

U.S. PATENT DOCUMENTS

| | | |
|---|---|---|
| 5,468,481 A | 11/1995 | Sharma |
| 5,849,589 A | 12/1998 | Tedder et al. |
| 6,379,970 B1 | 4/2002 | Liebler et al. |
| 6,406,705 B1 | 6/2002 | Davis et al. |
| 7,608,279 B2 | 10/2009 | Parisot et al. |
| 2012/0087862 A1 | 4/2012 | Hood |
| 2015/0301044 A1 | 10/2015 | Klein |

FOREIGN PATENT DOCUMENTS

| | | |
|---|---|---|
| WO | WO-2014/210353 A2 | 12/2014 |
| WO | WO-2016/040476 A1 | 3/2016 |
| WO | WO-2016/100977 A1 | 6/2016 |
| WO | WO-2016/168584 A1 | 10/2016 |
| WO | 2017106638 A1 | 6/2017 |
| WO | WO-2017/164936 A1 | 9/2017 |
| WO | 2019006022 A1 | 1/2019 |

OTHER PUBLICATIONS

Gubin et al Science Oct. 5, 2015 vo; 350 iss6257 p. 158-159.*
Andreatta, et al., "Characterizing the Binding Motifs of 11 Common Human HLA-DP and HLA-DQ Molecules using NNAlign", Immunology, vol. 136, No. 3, Jul. 2012, 306-311.
Andreatta, et al., "NNAlign: A Web-Based Prediction Method Allowing Non-Expert End-User Discovery of Sequence Motifs in Quantitative Peptide Data", PLoS One , vol. 6, Issue 11, Nov. 2011, 11 pages.
Chicz, et al., "Predominant Naturally Processed Peptides Bound to HLA-DR1 are Derived from MHC-related Molecules and are Heterogeneous in Size", Nature, vol. 358, No. 6389, Aug. 27, 1992, 764-768.
Chicz, et al., "Specificity and Promiscuity among Naturally Processed Peptides Bound to HLA-DR Alleles", Journal of Experimental Medicine, vol. 178, No. 1, Jul. 1993, 27-47.
Depontieu, et al., "Identification of Tumor-Associated, MHC Class II-restricted Phosphopeptides as Targets for Immunotherapy", Proceedings of the National Academy of Sciences of the United States of America, vol. 106, No. 29, Jul. 21, 2009, 12073-12078.
Hunt, et al., "Peptides Presented to the Immune System by the Murine Class II Major Histocompatibility Complex Molecule I-Ad", Science, vol. 256, No. 5065, Jun. 26, 1992, 1817-1820.
Kim, et al., "Determinants of Immunodominance for CD4 T cells", Current Opinion in Immunology, vol. 34, Jun. 2015, 13 pages.
Lippolis, et al., "Analysis of MHC Class II Antigen Processing by Quantitation of Peptides That Constitute Nested Sets", Journal of Immunology, vol. 169, No. 9, Nov. 2002, 5089-5097.
Mommen, et al., "Sampling from the Proteome to the Human Leukocyte Antigen-DR (HLA-DR) Ligandome Proceeds Via High Specificity", Molecular & Cellular Proteomics, vol. 15, No. 4, Apr. 2016, 1412-1423.

(Continued)

*Primary Examiner* — Joseph Woitach
(74) *Attorney, Agent, or Firm* — Foley & Lardner LLP; Sunit Talapatra

(57) ABSTRACT

A system and method for prediction of immunodominant epitopes is provided herein. MHCII peptidomics was used to discover complex bacterial epitopes and host antigen processing pathways. Novel insights into the features of antigenicity are leveraged to build an algorithm for prediction of immunodominant epitopes. Use of immunodominant epitopes is described.

18 Claims, 29 Drawing Sheets
Specification includes a Sequence Listing.

(56) References Cited

OTHER PUBLICATIONS

Nelson, et al., "Identification of the Naturally Processed Form of Hen Egg White Lysozyme Bound to the Murine Major Histocompatibility Complex Class II Molecule I-Ak", Proceedings of the National Academy of Sciences of the United States of America, vol. 89, No. 16, Aug. 1992, 7380-7383.
Rudensky, et al., "Sequence Analysis of Peptides Bound to MHC Class II Molecules", Nature, vol. 353, No. 6345, Oct. 17, 1991, 622-627.
Seamons, et al., "Competition Between two MHC Binding Registers in a Single Peptide Processed From Myelin Basic Protein Influences Tolerance and Susceptibility to Autoimmunity", Journal of Experimental Medicine, vol. 197, No. 10, May 19, 2003, 1391-1397.
Sette, "Invariant Chain Peptides in Most HLA-DR Molecules of an Antigen-processing Mutant", Science, vol. 258, No. 5089, Dec. 11, 1992, 1801-1804.
Sofron, et al., "High-resolution Analysis of the Murine MHC Class II Immunopeptidome", European Journal of Immunology, vol. 46, No. 2, Feb. 2016, 319-328.
Suri, et al., "First Signature of Islet β-Cell-Derived Naturally Processed Peptides Selected by Diabetogenic Class II MHC Molecules", Journal of Immunology, vol. 180, No. 6, Mar. 15, 2008, 3849-3856.
BPS Bioscience, IL-2-Luciferase Reporter (Luc)—Jurkat Cell Line, May 16, 2017, https://web.archive.org/web/20170516091246/http://lbpsbioscience.com/il2-jurkat-cell-line-60481, 1 page.
Andreatta, et al., "Accurate pan-specific prediction of peptide-MHC class II binding affinity with improved binding core identification", Immunogenetics, Nov. 2015, vol. 67, 641-650.
Jeannin, et al., "Outer membrane protein A (OmpA): a new pathogen-associated molecular pattern that interacts with antigen presenting cells-impact on vaccine strategies.", Vaccine 19, Dec. 2002, vol. 20 Suppl 4:A23-A27, 1 page.
Redmond, et al., "Single-cell TCRseq: paired recovery of entire T-cell alpha and beta chain transcripts in T-cell receptors from single-cell RNAseq", Genome Med Jul. 27, 2016 vol. 8 No. 80, pp. 1-12.
Sun, et al., "Listeriolysin O as a strong immunogenic molecule for the development of new anti-tumor vaccines", Human Vaccines & Immunotherapeutics, May 2013, 9:5, 1058-1068.
Young, "International Search Report and Written Opinion of PCT/US2018/039843", 18 pages.
Zhu, et al., "Crystal structure of MHC class II I-Ab in complex with a human CLIP peptide: prediction of an I-Ab peptide-binding motif", J Mot Biol Feb. 28, 2003 vol. 32G No. 4 pp. 1157-1174., 2 pages.
Alipanahi et al., "Predicting the sequence specificities of DNA- and RNA-binding proteins by deep learning," Nature Biotechnology, Aug. 2015, vol. 33, No. 8 (pp. 831-838).
Allison et al., "Immunological Adjuvants and Their Mode of Action, Developments in Biological Standardization," Vaccines, New Approaches to Immunological Problems, 1992, Chapter 19 (pp. 431-449).
Anders et al., "HTSeq—a Python framework to work with high-throughput sequencing data," Bioinformatics, 2015, vol. 31, No. 2 (pp. 166-169).
Appleby et al. "New technologies for ultra-high throughput genotyping in plants", Methods in Molecular Biology, Plant Genomics, vol. 513 (pp. 19-39).
Arunachalam et al., "Enzymatic reduction of disulfide bonds in lysosomes: characterization of a gamma-interferon-inducible lysosomal thiol reductase (GILT)," Proceedings of the National Academy of Sciences, USA, Jan. 18, 2000, vol. 97, No. 2 (pp. 745-750).
Aucouturier et al., "Adjuvants designed for veterinary and human vaccines," Vaccine, Mar. 21, 2001, vol. 19 (pp. 2666-2672).
Babbitt et al., "Binding of immunogenic peptides to Ia histocompatibility molecules," Nature, 1985, vol. 317 (359-361).
Bhardwaj et al., "TLR Agonists: Are They Good Adjuvants?" Cancer Journal, 2010. vol. 16, No. 4 (pp. 382-391).
Binder et al., "Compartments: unification and visualization of protein subcellular localization evidence," Database (Oxford), 2014, bau012 (9 pages).
Bland et al., "Statistical methods for assessing agreement between two methods of clinical measurement," The Lancet, Feb. 8, 1986, vol. 327, No. 8476 (pp. 307-310).
Calis et al., "Characterizing immune repertoires by high throughput sequencing: strategies and applications," Trends in Immunology, Dec. 2014, vol. 35, No. 12 (pp. 581-590).
Cao et al., "Comprehensive single cell transcriptional profiling of a multicellular organism by combinatorial indexing," bioRxiv preprint first posted online Feb. 2, 2017 (35 pages).
Cao et al., "Comprehensive single-cell transcriptional profiling of a multicellular organism," Science, Aug. 18, 2017, vol. 357, No. 6352 (pp. 661-667).
Carneiro et al., "Pacific biosciences sequencing technology for genotyping and variation discovery in human data," BMC Genomics, Aug. 5, 2012, vol. 13, No. 375 (7 pages).
Caskey et al., "Synthetic double-stranded RNA induces innate immune responses similar to a live viral vaccine in humans," The Journal of Experimental Medicine, Nov. 21, 2011, vol. 208, No. 12 (pp. 2357-2366).
Chatterjee et al., "Intracellular gene expression profile of Listeria monocytogenes," Infection and Immunity, Feb. 2006, vol. 74, No. 2 (pp. 1323-1338).
Christmann et al., "Human seroreactivity to gut microbiota antigens," Journal of Allergy and Clinical Immunology, Nov. 2015, vol. 136, No. 5 (pp. 1378-1386).
Conway et al., "ATG5 regulates plasma cell differentiation," Autophagy, Apr. 2013, vol. 9, No. 4 (pp. 528-537).
Conway et al., "Atg16l1 is required for autophagy in intestinal epithelial cells and protection of mice from Salmonella infection," Gastroenterology, Dec. 2013, vol. 145, No. 6 (pp. 1347-1357).
Corpet et al., "Multiple sequence alignment with hierarchical clustering," Nucleic Acids Res. Nov. 25, 1988, vol. 16, No. 22 (pp. 10881-10890).
Cresswell et al., "Thiol oxidation and reduction in MHC-restricted antigen processing and presentation," Immunologic Research, 1999, vol. 19 (pp. 191-200).
Crooks et al., "WebLogo: a sequence logo generator," Genome Research, Jun. 2004, vol. 14, No. 6 (pp. 1188-1190).
Dongre et al., "In vivo MHC Class II Presentation of Cytosolic Proteins Revealed by Rapid Automated Tandem Mass Spectrometry and Functional Analyses," European Journal of Immunology, May 2001, vol. 31, No. 5 (pp. 1485-1494).
Dupuis et al., "Dendritic Cells Internalize Vaccine Adjuvant after Intramuscular Injection," Cellular Immunology, May 25, 1998, vol. 186, No. 1 (pp. 18-27).
Eddy, S. R., "Accelerated Profile HMM Searches," PLoS Computational Biology, Oct. 2011, vol. 7, No. 10 (16 pages).
Erlich, H., "HLA typing using next generation sequencing: An overview," Human Immunology, Dec. 2015, vol. 76, No. 12 (pp. 887-890).
Finn et al., "The Pfam protein families database: towards a more sustainable future," Nucleic Acids Research, Jan. 2016, vol. 44, D279-285 (7 pages).
Gabrilovich et al., "IL-12 and mutant P53 peptide-pulsed dendritic cells for the specific immunotherapy of cancer," Journal of Immunotherapy with Emphasis on Tumor Immunology: Official Journal of the Society for Biological Therapy, Nov. 1, 1996, vol. 19, No. 6 (pp. 414-418).
Gierahn et al., "Seq-Well: Portable, Low-Cost RNA Sequencing of Single Cells at High Throughput," Nature Methods, Apr. 2017, vol. 14, No. 4 (8 pages).
Habib et al., "Div-Seq: Single-nucleus RNA-Seq reveals dynamics of rare adult newborn neurons," Science, Aug. 26, 2016, vol. 353, No. 6302 (pp. 925-928).
Habib et al., "Massively parallel single-nucleus RNA-seq with DroNc-seq," Nature Methods, Oct. 2017, vol. 14, No. 10 (pp. 955-958).

(56) References Cited

OTHER PUBLICATIONS

Hall et al., "Human genetic variation and the gut microbiome in disease," Nature Review Genetics, 2017, vol. 18 (pp. 690-699).
Hara et al., "Suppression of basal autophagy in neural cells causes neurodegenerative disease in mice," Nature, 2006, vol. 441 (pp. 885-889).
Hashimshony, et al., "CEL-Seq: Single-Cell RNA-Seq by Multiplexed Linear Amplification," Cell Reports, 2012, vol. 2, No., 3 (pp. 666-673).
Head et al., "Library construction for next-generation sequencing: Overviews and challenges," Biotechniques, 2014, vol. 56, No. 2 (pp. 61-77).
Heng et al., "The Immunological Genome Project: networks of gene expression in immune cells," Nature Immunology, Oct. 2008, vol. 9, No. 10 (pp. 1091-1094).
Hsieh et al., "A role for cathepsin L and cathepsin S in peptide generation for MHC class II presentation," The Journal of Immunology, 2002, vol. 168 (pp. 2618-2625).
Hsing et al., "The lysosomal cysteine proteases in MHC class II antigen presentation," Immunological Reviews, Sep. 23, 2005, vol. 207, No. 1 (pp. 229-241).
Imelfort et al., "De novo sequencing of plant genomes using second-generation technologies," Briefings in Bioinformatics, 2009, vol. 10, No. 6 (pp. 609-618).
Islam, et al., "Characterization of the single-cell transcriptional landscape by highly multiplex RNA-seq," Genome Research, 2011, vol. 21, No. 7 (pp. 1160-1167).
Janeway et al., "Monoclonal antibodies specific for Ia glycoproteins raised by immunization with activated T cells: possible role of T cellbound Ia antigens as targets of immunoregulatory T cells," Journal of Immunology, Feb. 1984, vol. 132, No. 2 (pp. 662-667).
Kalisky et al., "Genomic Analysis at the Single-Cell Level," Annual Review of Genetics, 2011, vol. 45 (pp. 431-445).
Kalisky et al., "Single-cell genomics," Nature Methods, Apr. 2011, vol. 8, No. 4 (pp. 311-314).
Kim et al., "TopHat2: accurate alignment of transcriptomes in the presence of insertions, deletions and gene fusions," Genome Biology, 2013, vol. 14, R36 (13 pages).
Klein et al., "Droplet barcoding for single-cell transcriptomics applied to embryonic stem cells," Cell, May 21, 2015, vol. 161 (pp. 1187-1201).
Krieg, A.M., "Therapeutic potential of Toll-like receptor 9 activation," Nature Reviews, Drug Discovery, Jun. 1, 2006, vol. 5, No. 6 (pp. 471-484).
Kronke et al., "Lenalidomide induces ubiquitination and degradation of CKIalpha in del(5q) MDS," Nature, Jul. 9, 2015, vol. 523 (pp. 183-188).
Lassen et al., "Atg16L1 T300A variant decreases selective autophagy resulting in altered cytokine signaling and decreased antibacterial defense," Proceedings of the National Academy of Sciences, USA, May 27, 2014, vol. 111, No. 21 (pp. 7741-7746).
Li et al., "Fast and accurate short read alignment with Burrows-Wheeler transform," Bioinformatics, 2009, vol. 25, No. 14 (pp. 1754-1760).
Liu et al., "Alternate interactions define the binding of peptides to the MHC molecule IA(b)," Proceedings of the National Academy of Sciences, USA, Jun. 25, 2002, vol. 99, No. 13 (pp. 8820-8825).
Macosko et al., "Highly Parallel Genome-wide Expression Profiling of Individual Cells Using Nanoliter Droplets," Cell, May 21, 2015, vol. 161 (pp. 1202-1214).
Mantere et al., "Targeted Next-Generation Sequencing Identifies a Recurrent Mutation in MCPH1 Associating with Hereditary Breast Cancer Susceptibility," PLOS Genetics, Jan. 28, 2016 (14 pages).
Marchler-Bauer et al., "CDD: NCBI's conserved domain database," Nucleic Acids Research, Jan. 2015, vol. 43, D222-6 (5 pages).
Margulies et al. "Genome sequencing in microfabricated high-density picolitre reactors", Nature, Jul. 31, 2005, vol. 437 (pp. 376-380).
Mathe et al., "Current methods of gene prediction, their strengths and weaknesses," Nucleic Acids Research, Oct. 1, 2002, vol. 30, No. 19 (pp. 4103-4117).
McDavid et al., "Modeling bi-modality improves characterization of cell cycle on gene expression in single cells," PLoS Computational Biology, Jul. 17, 2014, vol. 10, No. 7 (10 pages).
Melief et al., "Immunotherapy of established (pre)malignant disease by synthetic long peptide vaccines," Nature Reviews Cancer, May 2008 vol. 8, No. 5 (pp. 351-360).
Merrifield, "Solid Phase Peptide Synthesis. I. The synthesis of a Tetrapeptide," Journal of the American Chemical Society, 1963, vol. 85, No. 14 (pp. 2149-2154).
Mertins et al., "Ischemia in tumors induces early and sustained phosphorylation changes in stress kinase pathways but does not affect global protein levels," Molecular & Cellular Proteomics, Jul. 2014, vol. 13, No. 7 (pp. 1690-1704).
Miyazaki et al., "Mice lacking H2-M complexes, enigmatic elements of the MHC class II peptide-loading pathway," Cell, Feb. 23, 1996, vol. 84 (pp. 531-541).
Morozova et al., "Applications of next-generation sequencing technologies in functional genomics," Genomics, 2008. vol. 92 (pp. 255-264).
Ng et al., "Targeted capture and massively parallel sequencing of 12 human exomes", Nature, Sep. 10, 2009, vol. 461 (pp. 272-276).
Ormerod et al., "Genomic characterization of the 1 uncultured Bacteroidales family S24-7 inhabiting the guts of homeothermic animals," Microbiome, Jul. 7, 2016, vol. 4, No. 36 (17 pages).
Palm et al., "Immune-microbiota interactions in health and disease," Clinical Immunology, Aug. 2015, vol. 159, No. 2 (pp. 122-127).
Picelli et al. "Full-length RNA-seq from single cells using Smart-seq2," Nature Protocols, Jan. 2014, vol. 9, No. 1 (pp. 171-181).
Ramskold et al., "Full-length mRNA-Seq from single-cell levels of RNA and individual circulating tumor cells," Nature Biotechnology, Aug. 2012, vol. 30, No. 8 (777-782).
Rappsilber et al. "Protocol for micro-purification, enrichment, prefractionation and storage of peptides for proteomics using StageTips," Nature Protocols, 2007, vol. 2 No. 8 (pp. 1896-1906).
Robinson et al., "edgeR: A Bioconductor Package for Differential Expression Analysis of Digital Gene Expression Data," Bioinformatics, Jan. 1, 2010, vol. 26, No. 1 (pp. 139-140).
Ronaghi et al., "Real-time DNA sequencing using detection of pyrophosphate release," Analytical Biochemistry, 1996, vol. 242, Article 0432 (pp. 84-89).
Rosati et al., "Overview of methodologies for T-cell receptor repertoire analysis," BMC Biotechnoly, Jul. 10, 2017, vol. 17, No. 61 (1-16).
Rosenberg et al., "Scaling single cell transcriptomics through split pool barcoding," bioRxiv preprint first posted online Feb. 2, 2017 (13 pages).
Sabado et al., "Preparation of tumor antigen-loaded mature dendritic cells for immunotherapy," Journal of Visualized Experiments, Aug. 1, 2013, vol. 78 (8 pages).
Scallan et al., "Foodborne illness acquired in the United States—major pathogens," Emerging Infectious Diseases, Jan. 2011, vol. 17, No. 1 (pp. 7-15).
Schindelin, et al., "Fiji—an Open Source platform for biological image analysis," Nature Methods, 2012, vol. 9, No. 7 (pp. 676-682).
Schulze et al., "The mechanism of HLA-DM induced peptide exchange in the MHC class II antigen presentation pathway," Current Opinion in Immunology, Feb. 2012, vol. 24, No. 1 (pp. 105-111).
Shendure et al., "Accurate Multiplex Polony Sequencing of an Evolved Bacterial Genome," Science, Sep. 9, 2005, vol. 309 (pp. 1728-1732).
Smyth, "Linear models and empirical bayes methods for assessing differential expression in microarray experiments," Stat Appl Genet Mol Biol., 2004, vol. 3, Issue 1, Article 3 (28 pages).
Speiser et al., "Molecularly defined vaccines for cancer immunotherapy, and protective T cell immunity," Seminars in Immunology, Jun. 2010, vol. 22, No. 3 (pp. 144-154).
Stahl-Hennig et al., "Synthetic double-stranded RNAs are adjuvants for the induction of T helper 1 and humoral immune responses to

(56) References Cited

OTHER PUBLICATIONS human papillomavirus in rhesus macaques," PLoS Pathogens, Apr. 10, 2009, vol. 5, No. 4 (15 pages).
Stern et al., "Crystal structure of the human class II MHC protein HLA-DRI complexed with an influenza virus peptide," Nature, Mar. 17, 1994, vol. 368 (pp. 215-221).
Stoll et al., "Altered microbiota associated with abnormal humoral immune responses to commensal organisms in enthesitis-related arthritis," Arthritis Research & Therapy, Nov. 30, 2014, vol. 16 (10 pages).
Swiech et al., "In vivo interrogation of gene function in the mammalian brain using CRISPR-Cas9," Nature Biotechnology, 2014, vol. 33 (pp. 102-106) [Including Supplemental information, 4 pages].
Tang et al., "mRNA-Seq whole-transcriptome analysis of a single cell," Nature Methods, May 2009, vol. 6, No. 5 (pp. 377-382).
Tang et al., "RNA-Seq analysis to capture the transcriptome landscape of a single cell," Nature Protocols, Mar. 2010, vol. 5, No. 3 (pp. 516-535).
Thibodeau et al., "Targeting the MHC Class II antigen presentation pathway in cancer immunotherapy," Oncoimmunology, Sep. 1, 2012, vol. 1, No. 6 (pp. 908-916).
Tusnady et al., "Principles governing amino acid composition of integral membrane proteins: application to topology prediction," Journal of Molecular Biology, Oct. 23, 1998, vol. 283 (pp. 489-506).
Vitak et al., "Sequencing thousands of single-cell genomes with combinatorial indexing," Nature Methods, Jan. 2017, vol. 14, No. 3 (pp. 302-308).
Wang et al., "A systematic assessment of MHC class II peptide binding predictions and evaluation of a consensus approach," PLoS Computational Biology, Apr. 4, 2008, vol. 4, No. 4 (10 pages).
Weber et al., "Distinct CD4+ helper T cells involved in primary and secondary responses to infection," Proceedings of the National Academy of Sciences, USA, May 29, 2012, vol. 109, No. 24 (pp. 9511-9516).
Yu et al., "PSORTb 3.0: improved protein subcellular localization prediction with refined localization subcategories and predictive capabilities for all prokaryotes," Bioinformatics, Jul. 2010, vol. 26, No. 13 (pp. 1608-1615).
Zeng et al., "Gut Microbiota-Induced Immunoglobulin G Controls Systemic Infection by Symbiotic Bacteria and Pathogens," Immunity, Mar. 15, 2016, vol. 44, No. 33 (pp. 647-658).
Zheng et al. "Haplotyping germline and cancer genomes with high-throughput linked-read sequencing" Nature Biotechnology, Feb. 1, 2016, vol. 34, No. 3 (pp. 303-311) [with Supplemental Material].
Zheng et al., "Massively parallel digital transcriptional profiling of single cells," Nature Communications, Jan. 16, 2017, vol. 8, No. 14049 (12 pages).
Zilionis et al., "Single-cell barcoding and sequencing using droplet microfluidics," Nature Protocols, 2017, vol. 12, No. 1 (pp. 44-73).
Xu et al., "Identification of cell types from single-cell transcriptomes using a novel clustering method," Bioinformatics, Feb. 11, 2015, vol. 31, No. 12 (pp. 1974-1980).

\* cited by examiner

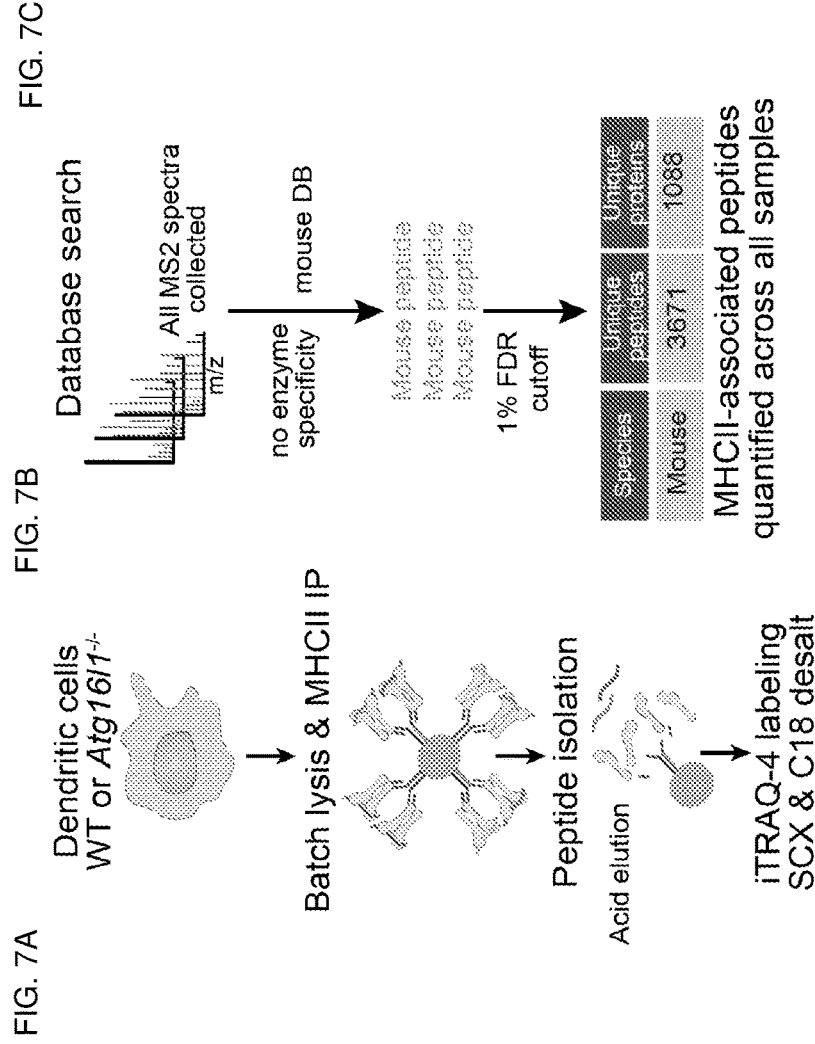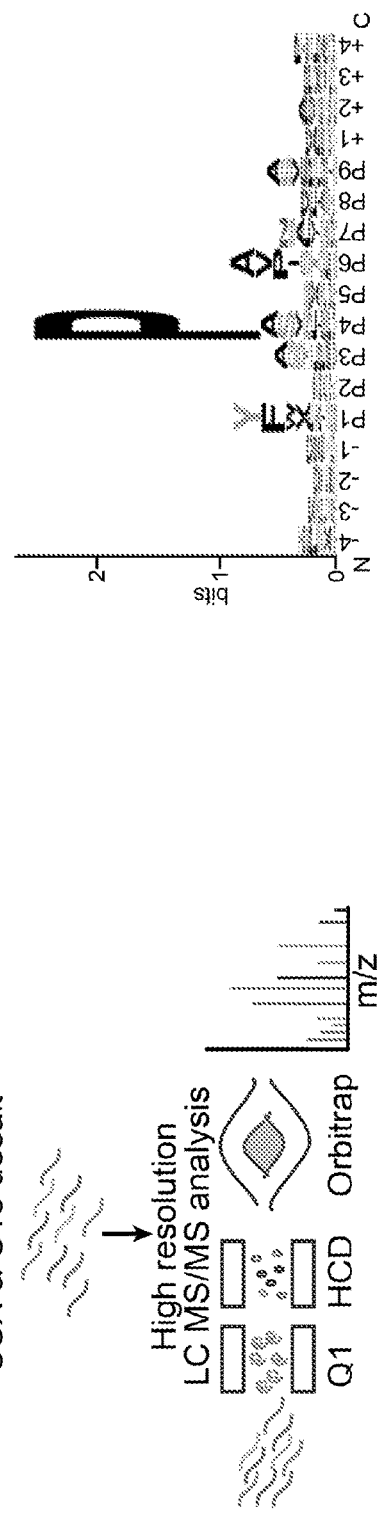

| | | |
|---|---|---|
| SEQ ID NO: 15069 | EDRRYNPPIIHQ | C-C motif chemokine 6 |
| SEQ ID NO: 15070 | GIKADKADKAAASGPASASAP | Integral membrane protein 2C |
| SEQ ID NO: 15071 | FVnYSNAVTLHLGNn | SLIT and NTRK-like protein 2 |
| SEQ ID NO: 15072 | EmEKEDRRYNPPIIHQGFQ | C-C motif chemokine 6 |
| SEQ ID NO: 15073 | EPRVLPYHPAQPGQAT | Chondroitin sulfate synthase 2 |
| SEQ ID NO: 15074 | GRRTDWEAPTGQPSAPGP | TBC1 domain family member 1 |
| SEQ ID NO: 15075 | DKNGNPLNSVFVAPAVTPVKGVL | Acid sphingomyelinase-like phosphodiesterase 3a |
| SEQ ID NO: 15076 | GDLEYQMSTTARAKR | Junction plakoglobin |
| SEQ ID NO: 15077 | ATPRDYYFALAHTVRDH | "Glycogen phosphorylase, liver form" |
| SEQ ID NO: 15078 | SSIASFKDPKISTSLPV | Plastin-2 |
| SEQ ID NO: 15079 | LPQDPTFHTPLDLYAYAR | Galectin-3-binding protein |
| SEQ ID NO: 15080 | DVDFDFAGPAIHGSAV | Voltage-dependent anion-selective channel protein 2 |
| SEQ ID NO: 15081 | GYPTAYPAAAPAYNPS | Protein FAM168A |
| SEQ ID NO: 15082 | DSPDVVYSPETIEARYE | Inositol-3-phosphate synthase 1 |
| SEQ ID NO: 15083 | TPDPNTAYASYPSASVEN | Synaptogyrin-2 |
| SEQ ID NO: 15084 | ESPDQWSSSSPHSASDW | Neurogenic locus notch homolog protein 2 |
| SEQ ID NO: 15085 | VDFDFAGPAIHGSAV | Voltage-dependent anion-selective channel protein 2 |
| SEQ ID NO: 15086 | DPTPDPNTAYASYPSASVEN | Synaptogyrin-2 |
| SEQ ID NO: 15087 | KLLEAKGPVTDVAYSHD | WD repeat-containing protein 1 |
| SEQ ID NO: 15088 | APVEGASPTSISAVDG | "Class II histocompatibility antigen, M alpha chain" |
| SEQ ID NO: 15089 | KKELEEQLGPVAEETR | Apolipoprotein E |
| SEQ ID NO: 15090 | LVEKIF | BPI fold-containing family B member 4 |
| SEQ ID NO: 15091 | SSVAFIKPGVNKAEVT | SLAM family member 5 |
| SEQ ID NO: 15092 | SPDQWSSSSPHSASDW | Neurogenic locus notch homolog protein 2 |
| SEQ ID NO: 15093 | APETRSQVTPSVPSEALDD | Low-density lipoprotein receptor-related protein 10 |
| SEQ ID NO: 15094 | YnIPFTEKnILYSAFLWRT | Protein Vmn2r60 |
| SEQ ID NO: 15095 | SPESPDQWSSSSPHSASDW | Neurogenic locus notch homolog protein 2 |
| SEQ ID NO: 15096 | TPSPESPDQWSSSSPHSASDW | Neurogenic locus notch homolog protein 2 |
| SEQ ID NO: 15097 | DGDSYRSPWSNKYDPP | F-actin-capping protein subunit beta |
| SEQ ID NO: 15098 | IGNERFRCPEAIFQPS | Beta-actin-like protein 2 |
| SEQ ID NO: 15099 | DGDSYRSPWSNKYDPPL | F-actin-capping protein subunit beta |
| SEQ ID NO: 15100 | RKIVYEGPELNHAFG | Prolow-density lipoprotein receptor-related protein 1 |

FIG. 8E (Cont.)

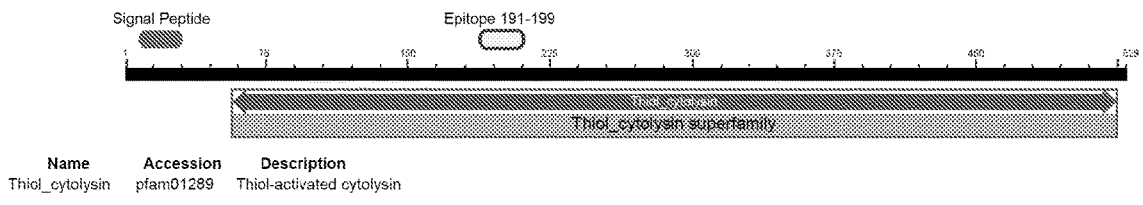
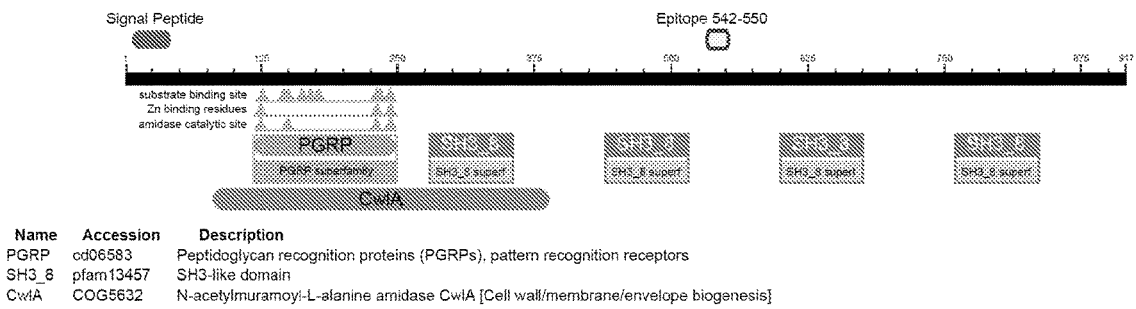
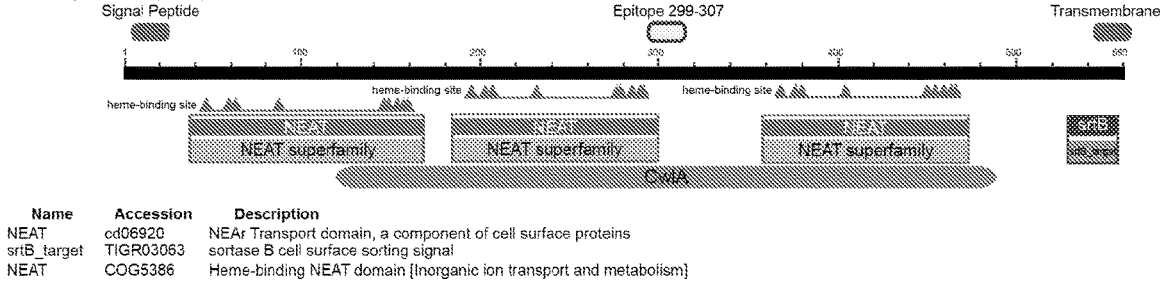
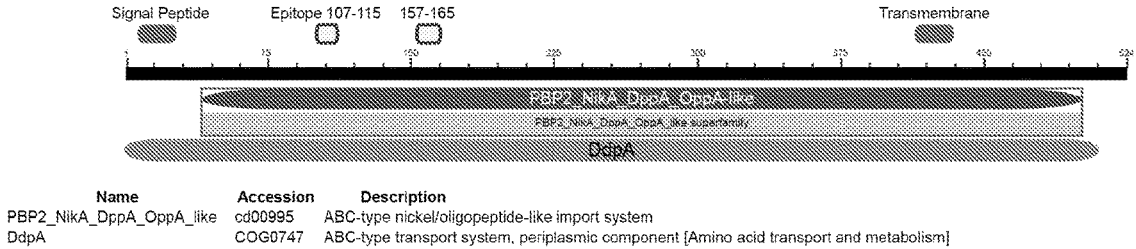
FIG. 10A

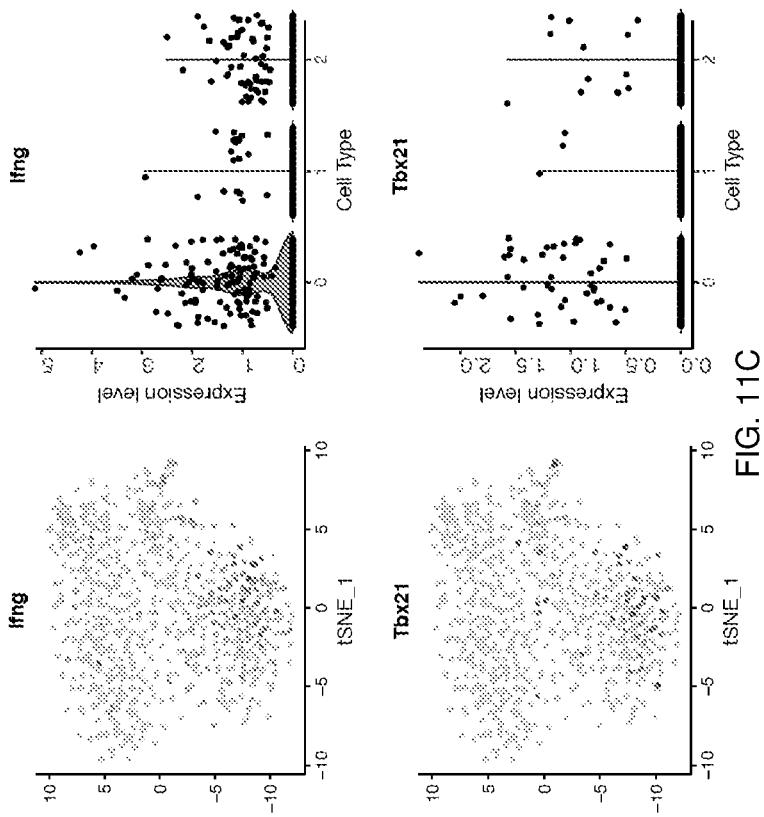
FIG. 11B
FIG. 11C
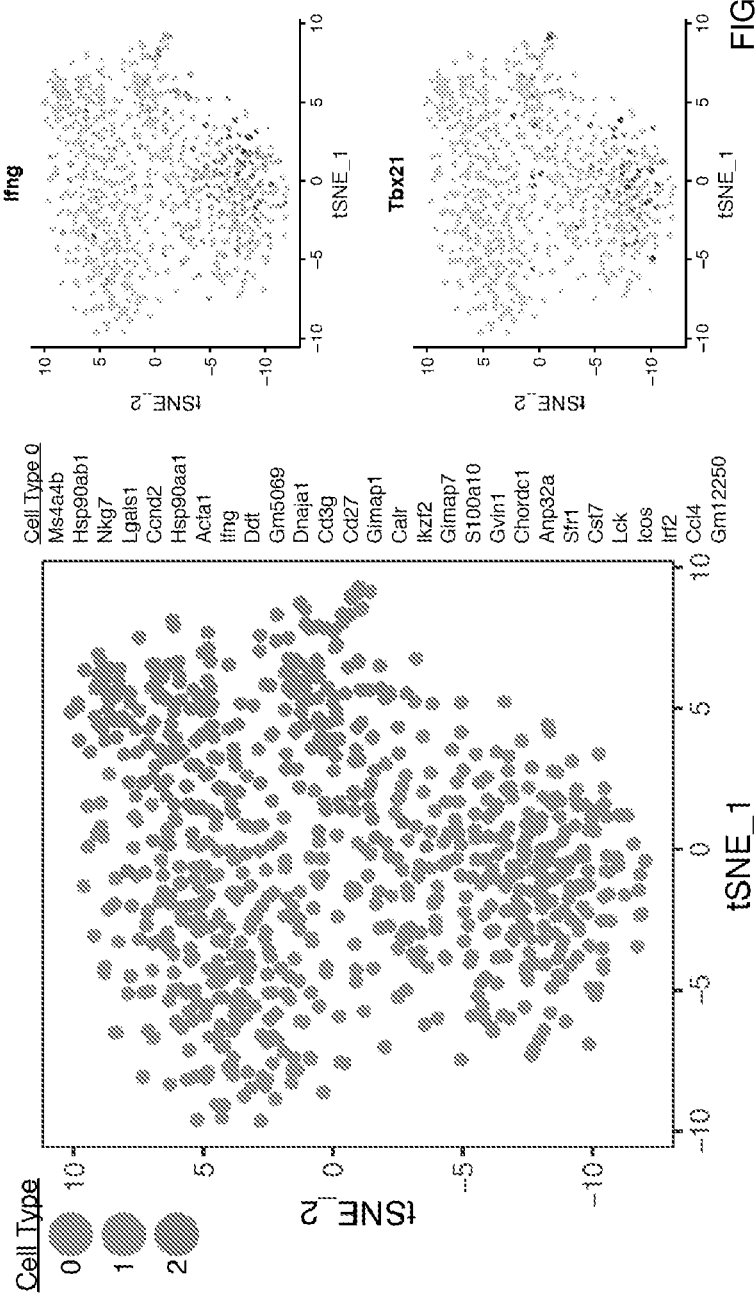
FIG. 11A

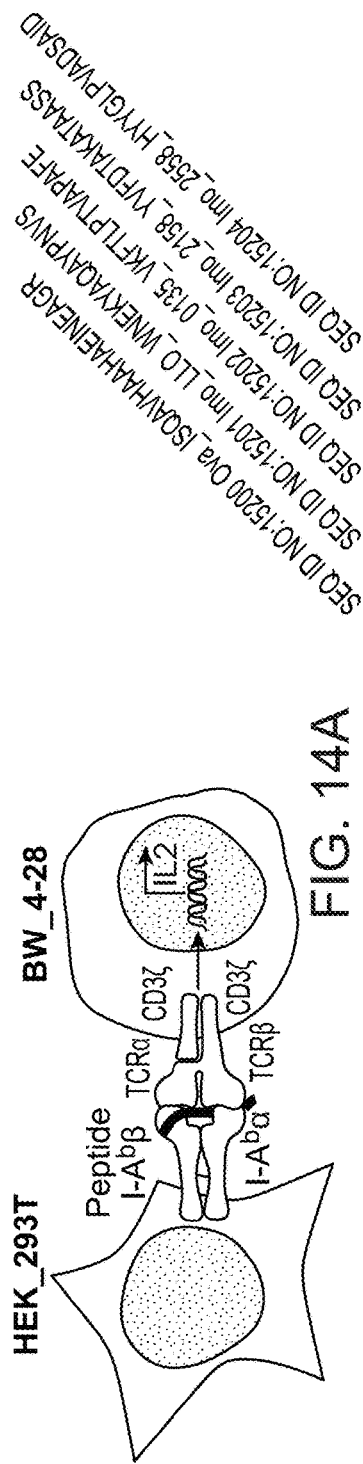
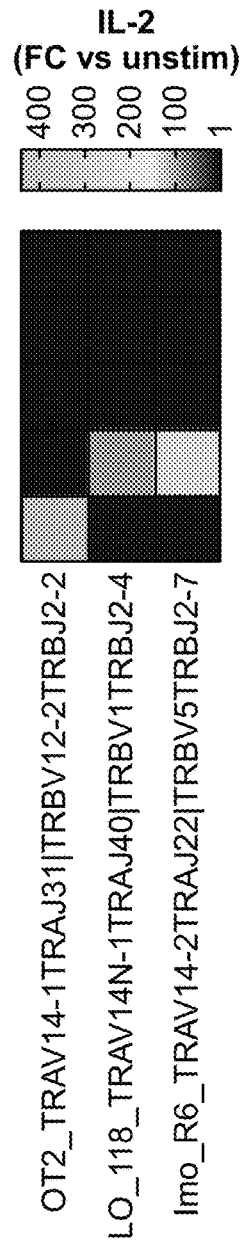
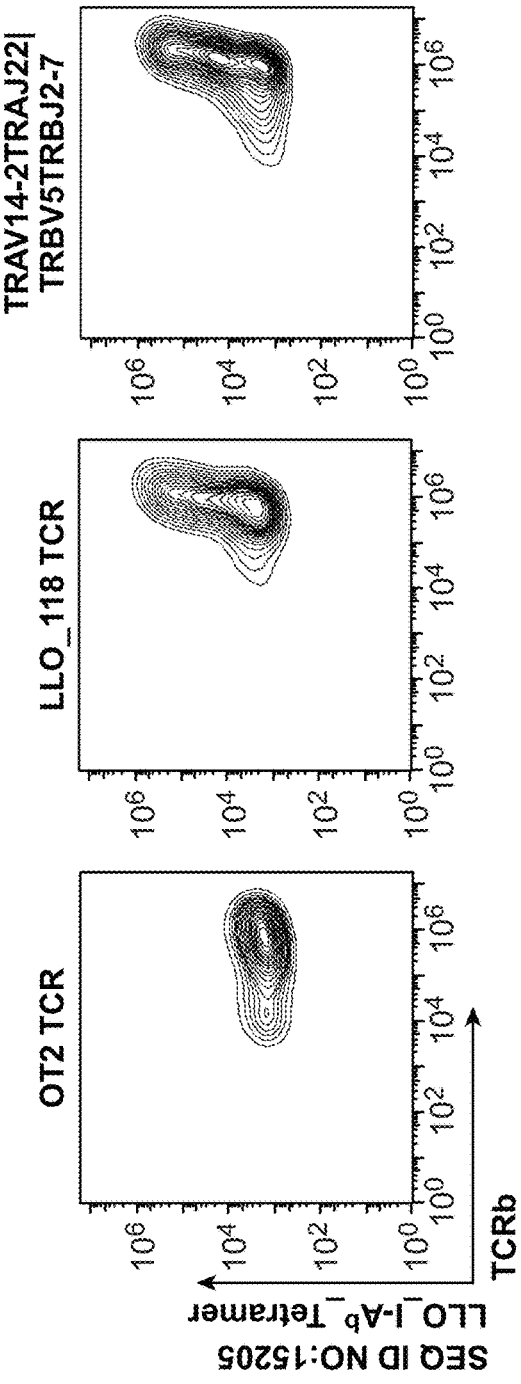
FIG. 14A
FIG. 14B
FIG. 14C
SEQ ID NO:15200 Ova_ISQAVHAAHAEINEAGR
SEQ ID NO:15201 lmo_0135_WNEKYAQAYPNVS
SEQ ID NO:15202 lmo_2158_VKFTLPTYAPAFE
SEQ ID NO:15203 lmo_15204 lmo_2558_HYFDTAKATAASS
SEQ ID NO:15204 YYFGLPVADSAID

**Many SusC-like genes in the *bacteroidales* genome (including human-associated strains)**

Muribaculum intestinale YL27
SusC/RagA TonB genes

Mouse I-A$^b$ (human orthologue HLA-DQ) epitopes in conserved region

*Hot Spot*

| gene | | 301 | | | | | | 350 351 | | | | 400 |
|------|---|-----|---|---|---|---|---|---------|---|---|---|-----|
| RS08305 | SEQ ID NO: 15219 | VDGVPITSGD | AGTGSGASFS | NSDAPIDFGN | GASEINPEDV | ESVTVLKGPA | ATALYGSRAA | NGAIVITTKS | GKA...... | EKGVGVTLNS | SITWEKAGYY |
| RS06325 | SEQ ID NO: 15220 | VDGIP..... | .......... | .......... | ......YDG | GLMSINPQDV | QSISVLKDAS | ATALYGSRAA | NGVILVTTKR | GQAGPAKVTL | EARWGANSRQ VSDYETVDDI |
| RS02245 | SEQ ID NO: 15221 | VDGVE..... | .......... | .......... | .......M. | NLARINANDI | ESVSLKDAS | AAAVYGAKAS | AGVMLVTTKS | GQE....... | DAAPKISFDL KAGWMQSTVS |
| RS04565 | SEQ ID NO: 15222 | CDGME..... | .......... | .......... | ........V. | SLGQINPNDI | ESTSVLKDAS | AAAIYGAKAS | SGVILVIITKS | GKDS...... | DGKVNVSYNG RFGWRKNTTS |
| RS07885 | SEQ ID NO: 15223 | IDGAE..... | .......... | .......... | .........G. | DLSRVNPNHV | ESISVLKDAS | AAAVYGARAA | FGVILVTTKS | GSEK...... | DGKATVRYSG RVGWEEPTTS |
| RS07765 | SEQ ID NO: 15224 | VDGIP..... | .......... | .......... | .......AE | SYPNINPSDI | ESIEVMLKDAS | AAATYGSRAN | SGVIIITTKS | GKS....... | .GMTKIDVSG RIGFGKLAKD |
| RS10090 | SEQ ID NO: 15225 | IDGVM..... | .......... | .......... | .....TREN | PGTILNSNDV | ESIQVLKDAA | SASIYGAQAA | NGVIIITTKR | .AK....... | KGECRVTFDA TLTLQTYQSG |
| RS05180 | SEQ ID NO: 15226 | VDGTP..... | .......... | .......... | ...VS | DLDNVNPDDV | ESIEVLKDAA | TASIYGARAA | AGVMILVTTK. | GAK....... | EGDLSITYNG EFSLMHASSY |
| RS03505 | SEQ ID NO: 15227 | IDSVE..... | .......... | .......... | ..CALS | QLSELPAADI | ESVSVLKDAA | SAAIYGVRAA | NGVILVTTKR | GQK....... | SEKVSVNYQG SYTLQTPGTL |
| RS02580 | SEQ ID NO: 15228 | VDGMT..... | .......... | .......GIA. | ..ISDVNPGDI | ENISILKDAS | AAAIYGSRAA | NGVIIITTKQ | GME....... | S.RPSVTYSG NISFETVAKR |
| RS05425 | SEQ ID NO: 15229 | VDGMPMR..S | GRS..TGDTG | A.FGSAGATE | PTADLNPEDI | ESLSVTTGAA | AAALYGSEAA | NGAIVITTKK | GEA....... | .GKTKITVGT NTEWNQAWIL |
| RS02610 | SEQ ID NO: 15230 | IDGIPMF..D | VNT..GEEKG | GTMAKQPGSS | SVADINPEDI | ESMSVLSGPS | AAALYGSAAA | SGVILVITTKK | GSE....... | .GRAKLTVSN TTQFHTANMT |
| RS03105 | SEQ ID NO: 15231 | VDGIPML..D | MSRAATQPEG | VVEGAAQTGD | PLSAINPEDI | ENISVLSGES | AAALYGSAAA | NGVMITTKK | GEE....... | .GQTRVITSN NTTFQRVAVM |
| RS09140 | SEQ ID NO: 15232 | IDGIPMP..N | LSDLLDQPED | NFSGMGQQSGD | GASMINPEDI | ESMSVLSGAA | ASALYGSQAS | NGVIIIITTKK | GNT....... | .NGLRVTVSN STQFYRAMAT |
| Consensus | SEQ ID NO: 15233 | IDG.p..... | .......... | .......... | ....lNp.Dl | EsisVlkdaa | aaa..YG.rAa | nGvIiiTTk. | G......... | g..vt.... |
| | SEQ ID NO: 15234 | | | | | | | | | | |

Motif score
☐ >1E−10
☐ >1E−11

Register overlap
☐ 1x
☐ 2x
☐ 3x
☐ 4x
☐ 5x

Tested Epitope: VLKDASAAAIYGSR
Associated with Treg reactivity in healthy mice

FIG. 22

SYSTEMS AND METHODS FOR MHC CLASS II EPITOPE PREDICTION

CROSS-REFERENCE TO RELATED APPLICATIONS

This application is a national stage application of International Application No. PCT/US2018/039843 filed Jun. 27, 2018, which claims the benefit of U.S. Provisional Application No. 62/525,673, filed Jun. 27, 2017. The entire contents of the above-identified applications are hereby fully incorporated herein by reference.

STATEMENT REGARDING FEDERALLY SPONSORED RESEARCH

This invention was made with government support under grant numbers DK043351 and AI109725 awarded by the National Institutes of Health. The government has certain rights in the invention.

REFERENCE TO AN ELECTRONIC SEQUENCE LISTING

The contents of the electronic sequence listing ("BROD-0671US_ST25.txt;" 3.2 MB and created on Mar. 24, 2020) is herein incorporated by reference in its entirety.

REFERENCE TO AN ELECTRONIC SEQUENCE LISTING

The contents of the electronic sequence listing ("BROD-0671US_ST25.txt;" 3.2 MB and created on Mar. 24, 2020) is herein incorporated by reference in its entirety.

TECHNICAL FIELD

This disclosure relates generally to methods and systems for the prediction of MHCII immunodominant epitopes requiring only an annotated genome sequence as an input and methods of using the predicted epitopes.

BACKGROUND

Canonical CD4 T cell responses are restricted to cognate peptide antigen presented by MHCII, which is in turn dictated by sequence-specific interactions between the peptide backbone and MHCII binding groove (Babbitt et al., 1985; Stern et al., 1994). Degeneracy in this interaction allows for presentation of a broad spectrum of peptide antigens and promotes diverse responses to potential antigens. However, CD4 T cell responses tend to be constrained to a limited set of immunodominant epitopes even when the pool of available peptide epitopes is not limiting. Thus, the T cell response must be balanced with respect to the magnitude of the response against any given epitope (to maximize efficacy) and diversity towards multiple epitopes (to combat epitope escape). Despite intensive investigation, the factors controlling immunodominance and antigenicity are incompletely understood.

At the level of antigen presenting cells, several lysosomal pathways contribute to antigen processing and epitope selection (Kim and Sadegh-Nasseri, 2015). In this context, numerous thiol reductases (Arunachalam et al., 2000; Cresswell et al., 1999) and proteases (Hsieh et al., 2002; Hsing and Rudensky, 2005) perform redundant functions in converting native proteins into MHCII ligands. Sequence- and structure-specific preferences of these enzymes for their substrates can bias which peptides are ultimately processed and loaded onto MHCII. Furthermore, kinetic parameters of the peptide-MHCII interaction impact the stability of the complex such that weak-binding peptides are replaced by means of HLA-DM editing (Miyazaki et al., 1996; Schulze and Wucherpfennig, 2012). Taken together, the complexity of antigen processing and limited availability of model immunodominant antigens has posed a barrier to understanding the biochemical features of antigenicity.

Historically, defining immunodominant CD4 T cell epitopes has been empirical. More recently, unbiased approaches for epitope discovery have been introduced. In this context, autologous self-epitopes have been identified by immunoaffinity purification of MHCII-associated peptides followed by Edman degradation sequencing or mass spectrometry (Chicz et al., 1993; Chicz et al., 1992; Hunt et al., 1992; Lippolis et al., 2002; Mommen et al., 2016; Rudensky et al., 1991; Sette et al., 1992; Sofron et al., 2016). Later advancements in mass spectrometry allowed for identification of tumor antigens (Depontieu et al., 2009) and autoantigens (Seamons et al., 2003; Suri et al., 2008). While detection of MHCII-associated peptides derived from exogenous proteins has been achieved (Nelson et al., 1992), identifying epitopes from complex microorganisms remains challenging. Moreover, quantitative assessment of T cell responses to novel epitopes faces technical limitations.

Citation or identification of any document in this application is not an admission that such document is available as prior art to the present invention.

SUMMARY

It is an objective of the present invention to provide novel methods and computer-implemented systems to predict MHCII binding peptides using only a genome sequence of a target cell type or target pathogen (Bacteria originated T cell antigen (BOTA)). It is another objective of the present invention to provide novel methods and systems for identifying immunodominant epitopes for any target cell type or target pathogen and for any MHCII allele. In certain example embodiments, Applicants developed methods and systems that utilize a deep neural network that is trained using peptidomic data obtained by isolating MHC II complexes from antigen presenting cells (e.g., dendritic cells). In certain example embodiments, provided is a broadly applicable technology platform for antigen discovery and specification of immunodominance hierarchies.

In one aspect, the present invention provides for a method of preparing one or more peptides for an immunological composition comprising: identifying MHCII antigenic epitopes for a pathogen, commensal microorganism or diseased cell; and formulating an immunological composition comprising one or more of the identified epitopes, wherein identifying MHCII antigenic epitopes comprises generating, by a processor, a set of candidate antigens from one or more input genome sequences derived from a target pathogen, commensal microorganism or diseased cell, and generating, by the processor, a ranked set of antigenic epitopes from the candidate antigens using a deep neural network. The method may further comprise sequencing a biological sample to generate one or more input genome sequences. The deep neural network may be trained using a set of MHCII-presented peptides bound to antigen presenting cells. The antigen presenting cells may be dendritic cells.

In certain embodiments, generating a set of candidate antigens from one or more input genome sequences comprises: predicting, by the processor, genes from an input genome sequence; and defining, by the processor, a set of candidate antigens from the set of predicted genes based on one or more of protein cellular location, transmembrane structure, and domain distribution. Defining, by the processor, a set of candidate antigens from the set of predicted genes, may comprise: selecting surface and secreted proteins; masking intracellular regions and transmembrane domains of the surface and extracellular proteins; excluding regions that are within domains of less than 30 amino acids; excluding regions between a series of inaccessible domains; and excluding inter-domain regions between a series of adjacent domains wherein the inter-domain regions are less than or equal to 20 amino acids. The method may further comprise masking up to 20 amino acids flanking the intracellular regions and transmembrane domains. In certain embodiments, 8 amino acids flanking the intracellular regions and transmembrane domains are masked. The surface protein may be a cell wall protein. The surface protein may be an outer membrane protein. The antigenic epitopes may be derived from candidate antigens more than 20 amino acids away from a transmembrane domain. The candidate antigens may comprise a tertiary structure required for proteolytic enzyme accessibility. The candidate antigens may comprise a defined MHCII-binding motif in the primary amino acid sequence of the predicted genes. The defined MHCII-binding motif may be the I-A$^b$-binding motif. The antigenic epitopes may comprise a tertiary structure required for accessibility to a MHCII binding groove.

In certain embodiments, generating, by the processor, a ranked set of antigenic epitopes from the candidate antigens using a deep neural network comprises: encoding each amino acid of an input candidate antigen into a p-dimensional binary vector; converting the binary vector to a descriptor matrix S; convoluting the descriptor matrix S to a scoring matrix X; and transforming the scoring matrix X into a d-dimensional vector Z, wherein vector Z is input for a neural network.

In certain embodiments, the antigenic epitopes are specific for an HLA type.

In certain embodiments, the method further comprises: isolating MHCII-peptide complexes from antigen presenting cells; identifying bound peptides from the MHCII-peptide complexes; and training the deep neural network using the set of identified peptides. The antigen presenting cells may be exposed to a target pathogen, commensal microorganism or diseased cell. The antigen presenting cells may be dendritic cells.

In certain embodiments, the candidate antigens are expressed in the pathogen, commensal microorganism or diseased cell.

In certain embodiments, the pathogen is selected from the group consisting of a bacterium, a virus, a protozoon, and an allergen.

In certain embodiments, the diseased cell is a cancer cell. The cancer cell may be obtained from a subject. The method may further comprise identifying non-silent tumor specific somatic mutations from the subject specific cancer cell, wherein the ranked set of antigenic epitopes are generated from said mutations.

In certain embodiments, the diseased cell is associated with an autoimmune disease.

In certain embodiments, the pathogen comprises a bacteria belonging to a family selected from the group consisting of *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia*.

In certain embodiments, the commensal microorganism comprises a bacterium belonging to a genus selected from the group consisting of *Bacteroides, Clostridium, Faecalibacterium, Eubacterium, Ruminococcus, Peptococcus, Peptostreptococcus, Bifidobacterium, Lactobacillus* and *Akkermansia*; or a fungus selected from the group consisting of *Candida, Saccharomyces, Aspergillus, Penicillium, Rhodotorula, Trametes, Pleospora, Sclerotinia, Bullera,* and *Galactomyces*.

In certain embodiments, the antigen presenting cell comprises a subject specific MHCII allele. The antigen presenting cell may comprise a human MHCII allele.

In certain embodiments, the one or more input genome sequences is obtained by whole genome or whole exome sequencing.

In certain embodiments, the method further comprises detecting whether one or more of the antigenic epitopes is present in a sample from a subject suffering from an infection, autoimmune disease, allergy, or cancer.

In certain embodiments, the antigenic epitopes are about 9 to 20 amino acids in length.

In certain embodiments, the deep neural network is trained using a set of MHCII-presented peptides comprising one or more of SEQ ID NOs: 1-14979. The deep neural network may be trained using a set of MHCII-presented peptides comprising one or more of SEQ ID NOs: 14980-15027.

In certain embodiments, the immunological composition is a protective vaccine or tolerizing vaccine composition comprising one or more of the antigenic epitopes. The vaccine composition may be directed to a bacterium, a virus or a protozoon. The vaccine composition may be directed to a cancer. The vaccine composition may be directed to an autoimmune disease or allergy, whereby administration of the vaccine induces tolerance to the one or more antigenic epitopes.

In certain embodiments, the vaccine composition is directed to *Listeria*. The vaccine composition may comprise one or more *Listeria* peptides selected from the peptides listed in Table 1. The one or more *Listeria* peptides may be derived from lmo0202, lmo2558, lmo2185, or lmo0135. The one or more *Listeria* peptides may be selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT).

In certain embodiments, the vaccine composition comprises autologous dendritic cells or antigen presenting cells pulsed with the one or more epitopes.

In another aspect, the present invention provides for a method of identifying one or more immunodominant epitopes comprising: expressing in a first population of immune cells one or more peptides for an immunological composition prepared according to claim 1, wherein the first population of immune cells comprise a detectable reporter gene; expressing in a second population of CD4+ immune cells a TCRαβ library expressing TCRαβ pairs identified in a subject suffering from an infectious disease, autoimmunity, cancer or allergy; incubating the first population of immune cells with the second population of immune cells; sorting immune cells positive for the detectable reporter gene; and identifying peptides bound to MHCII in immune cells positive for the detectable reporter gene. The TCRαβ pairs may be identified by T cell profiling. The TCRαβ pairs may be determined by targeted single cell RNA-seq (TCRseq). The T cells may be analyzed by RNA-seq to determine single cells having a specific cell state and TCRαβ pairs are identified in the T cells having the specific cell state. The specific cell state may be a protective phenotype or a pathogenic phenotype. The reporter may be an inducible fluorescent marker protein, wherein the marker protein is induced when a TCRαβ pair detects an MHCII epitope. The fluorescent marker may be under control of the IL-2 promoter. The method may further comprise formulating a vaccine composition comprising one or more of the immunodominant epitopes. The vaccine may be a protective vaccine or a tolerizing vaccine. The vaccine may comprise autologous dendritic cells or antigen presenting cells pulsed with one or more of the immunodominant epitopes.

In another aspect, the present invention provides for a method of identifying peptide antigens from a live bacterial pathogen comprising: isolating MHCII-peptide complexes from dendritic cells exposed to a bacterial pathogen; isolating the peptides from the MHCII-peptide complexes; and sequencing the isolated peptides.

In another aspect, the present invention provides for a method of determining immune related health status in a subject comprising: preparing one or more peptides for an immunological composition according to any embodiment herein; exposing the one or more peptides to immune cells obtained from the subject; and measuring cytokine secretion. The cytokines measured may comprise IL-2, IFN-γ, IL-17, and/or IL-10. The method may further comprise measuring immune cell types reactive to the epitopes in the subject. The immune cell types may comprise Treg, Th1, Th17 and/or Th2 cells. The immune cells may be measured using MHCII tetramers.

In another aspect, the present invention provides for a method of determining immune related health status in a subject comprising: preparing one or more peptides for an immunological composition according any embodiment herein; and measuring immune cell types reactive to the epitopes in the subject. The immune cell types may comprise Treg, Th1, Th17 and/or Th2 cells. The immune cells may be measured using MHCII tetramers.

In another aspect, the present invention provides for a method of constructing a deep neural network for identifying MHCII antigenic epitopes comprising: isolating MHCII-peptide complexes from antigen presenting cells expressing a MHCII type; isolating peptides from the MHCII-peptide complexes; sequencing the isolated peptides; and training a deep neural network for predicting antigenic epitopes for the MHCII type using the set of isolated peptides. The deep neural network may be trained by testing randomly initialized parameters for the peptides. The parameters may be tested in a three-fold cross validation scheme. The parameters may comprise cellular localization, inter-domain structure, domain size and/or tertiary structure. The cellular localization may comprise peptides derived from extracellular, intracellular or transmembrane proteins.

In another aspect, the present invention provides for a method for identifying MHCII antigenic epitopes comprising: generating, by a processor, a set of candidate antigens from one or more input genome sequences; and generating, by the processor, a ranked set of antigenic epitopes from the candidate antigens using a deep neural network, wherein the deep neural network is trained using a set of MHCII-presented peptides isolated from antigen presenting cells. The antigen presenting cells may be dendritic cells.

In certain example embodiments, generating, by the processor, a set of candidate antigens from one or more input genome sequences may comprise: predicting, by the processor, genes from an input genome sequence; and defining, by the processor, a set of candidate antigens from the set of predicted genes based on one or more of protein cellular location, transmembrane structure, and domain distribution.

In certain example embodiments, defining, by the processor, a set of candidate antigens from the set of predicted genes, may comprise: selecting surface and secreted proteins; masking intracellular regions and transmembrane domains of the surface proteins; excluding regions that are within domains of less than 30 amino acids; excluding inter-domain regions between transmembrane domains or domains of less than 30 amino acids; and/or excluding inter-domain regions between a series of adjacent domains wherein the inter-domain regions are less than or equal to 20 amino acids. The method may further comprise masking up to 20 amino acids flanking the intracellular regions and transmembrane domains. In certain embodiments, 8 amino acids flanking the intracellular regions and transmembrane domains are masked. In other embodiments, regions located in or between inaccessible domains are excluded. The term "inaccessible domains" as used herein refers to domains that are (1) intracellular, (2) within a transmembrane domain plus 8 amino acids flanking each end, or (3) any domain identified by PFAM that is less than 30 amino acids in length. These criteria were informed by the training dataset (endogenous mouse peptides bound to MHCII). The metric used for domain mapping may be based on other features, such as the distance to the upstream and downstream domains, the density of flanking domains and the size of the domain. MHCII epitopes may be present between small domains, but not present in small domains.

The surface protein may be a cell wall protein. The surface protein may be an outer membrane protein. The antigenic epitopes may be derived from candidate antigens more than 20 amino acids away from a transmembrane domain. The candidate antigens may comprise a tertiary structure required for proteolytic enzyme accessibility (e.g., solvent exposed epitopes rather than buried epitopes). In certain embodiments, protein regions predicted to be accessible by proteases are prioritized. The candidate antigens may comprise a defined MHCII-binding motif in the primary amino acid sequence of the predicted genes. This parameter may be used before, during or after the candidate antigens are provided to the neural network. The defined MHCII-binding motif may be the I-$A^b$-binding motif. The antigenic epitopes may comprise a tertiary structure required for accessibility to a MHCII binding groove.

Generating, by the processor, a ranked set of antigenic epitopes from the candidate antigens using a deep neural network may comprise: encoding each amino acid of an input candidate antigen into a p-dimensional binary vector; converting the binary vector to a descriptor matrix S; convoluting the descriptor matrix S to a scoring matrix X; and transforming the scoring matrix X into a d-dimensional vector Z, wherein vector Z is input for a neural network.

The method of any embodiment described herein may further comprise: isolating MHCII-peptide complexes from antigen presenting cells; isolating the peptides from the MHCII-peptide complexes; sequencing the isolated peptides; and training the deep neural network using the set of isolated peptides. The antigen presenting cells may be exposed to a target cell type or target pathogen. The antigen presenting cells may be dendritic cells.

The input genome sequence may be derived from a target cell type or target pathogen. The candidate antigens may be expressed in the target cell type or target pathogen. The target cell type or target pathogen of any embodiment herein may be selected from the group consisting of a bacterium, a virus, a protozoa, an allergen and a diseased cell.

The diseased cell may be a cancer cell. The cancer cell may be obtained from a subject in need thereof. The method may further comprise identifying non-silent tumor specific somatic mutations from the subject specific cancer cell, wherein the ranked set of antigenic epitopes are generated from said mutations.

The diseased cell may be associated with an autoimmune disease.

The target pathogen may comprise a bacteria belonging to a family selected from the group consisting of *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia.*

The antigen presenting cell may comprise a subject specific MHCII allele. The antigen presenting cell may comprise a human MHCII allele. The one or more input genome sequences may be obtained by whole genome or whole exome sequencing. The method may further comprise detecting whether one or more of the antigenic epitopes is present in a sample from a subject suffering from an infection, autoimmune disease, allergy, or cancer. In certain embodiments, such as when identifying immunodominant epitopes for personalized medicine, epitopes that are expressed in a subject in need thereof are selected for an immunogenic composition.

The deep neural network may be trained using a set of MHCII-presented peptides comprising one or more of SEQ ID NOs: 1-14979. The deep neural network may be trained using a set of MHCII-presented peptides comprising one or more of SEQ ID Nos: 14980-15027.

In certain embodiments, the deep neural network trained using a set of MHCII-presented peptides isolated from a dendritic cell can be used to predict antigenic epitopes from any input genome sequence, such as from a pathogen or a different organism. Not being bound by a theory, training the neural network with MHCII-presented peptides provides the neural network with antigenic determinants for generally predicting MHCII binders. The present invention thus provides novel determinants of antigenicity previously not known.

The method may further comprise preparing a vaccine composition comprising one or more antigenic epitopes from the set of antigenic epitopes generated by the processor. The antigenic epitopes may be about 9 to 20 amino acids in length. The vaccine composition may be directed to a bacterium, a virus or a protozoa. The vaccine composition may be directed to a cancer. The vaccine composition may be directed to an autoimmune disease, whereby administration of the vaccine induces tolerance to the antigenic epitope. The vaccine composition may be directed to *Listeria*. The vaccine composition may comprise one or more *Listeria* peptides selected from the peptides listed in Table 1. The one or more *Listeria* peptides may be derived from lmo0202, lmo2558, lmo2185, or lmo0135. The one or more *Listeria* peptides may be selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT). Not being bound by a theory, the vaccine may be directed to (1) any microbial pathogen, (2) any commensal microorganism, (3) any food allergen, (4) any tumor/malignancy, (5) any host tissue that is targeted by adaptive immune system in autoimmune disease. The method may be used to prepare tolerizing vaccines or protective vaccines. The vaccine may comprise autologous dendritic cells or antigen presenting cells pulsed with the one or more peptides.

In another aspect, the present invention provides for a method of identifying immunodominant epitopes comprising: expressing in a first population of immune cells a peptide MHCII library comprising antigenic epitopes identified according to the method of any embodiment herein, wherein the first population of immune cells comprise a detectable reporter gene; expressing in a second population of CD4+ immune cells a TCRab library expressing TCRab pairs identified in a subject suffering from an infectious disease, autoimmunity, cancer or allergy; incubating the first population of immune cells with the second population of immune cells; sorting immune cells positive for the detectable reporter gene; and identifying peptides bound to MHCII in immune cells positive for the detectable reporter gene. The TCRab pairs may be identified by single cell profiling. The TCRab pairs may be determined by targeted single cell RNA-seq (TCRseq). The T cells may be analyzed by RNA-seq to determine single cells that are activated and TCRab pairs are identified in the activated T cells. The reporter may be an inducible fluorescent marker protein, wherein the marker protein is induced when a TCRab pair detects a MHCII epitope. The fluorescent marker may be under control of the IL-2 promoter. The method may further comprise administering to the subject a vaccine comprising one or more of the immunodominant epitopes. The vaccine may be a protective vaccine or a tolerizing vaccine. The vaccine may comprise autologous dendritic cells or antigen presenting cells pulsed with one or more of the immunodominant epitopes.

In another aspect, the present invention provides for a method of identifying peptide antigens from a live bacterial pathogen comprising: isolating MHCII-peptide complexes from dendritic cells exposed to a bacterial pathogen; isolating the peptides from the MHCII-peptide complexes; and sequencing the isolated peptides.

In another aspect, the present invention provides for a peptide set for training a MHCII neural network comprising one or more of SEQ ID NOs: 1-14979.

In another aspect, the present invention provides for a peptide set for training a MHCII neural network comprising one or more of SEQ ID NOs: 14980-15027.

In another aspect, the present invention provides for a *Listeria* vaccine comprising one or more peptides selected from the peptides listed in Table 1. The one or more peptides may be derived from lmo0202, lmo2558, lmo2185, or lmo0135. The one or more *Listeria* peptides may be selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT). The vaccine may comprise autologous dendritic cells or antigen presenting cells pulsed with the one or more peptides.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 7—MHCII peptidomics in primary murine dendritic cells results in more than 3,700 distinct peptide identifications and defines the I-A$^b$-binding motif. FIG. 7A is an example experimental workflow for immunopurification and sequencing of MHCII-associated peptides from murine dendritic cells. MHCII-peptide complexes were immunopurified from WT and Atg16l1$^{-/-}$ cells. Associated peptides were then acid-eluted, labeled with iTRAQ4 reagents, desalted with SCX and C18, and analyzed using high resolution LC-MS/MS. FIG. 7B is an example database search strategy for MHCII-peptide sequencing. All MS/MS spectra were searched against a database containing mouse proteins using Spectrum Mill software with a "no enzyme" specificity. Mouse peptides were validated using a 1% FDR cutoff, and the total numbers of peptides quantified across all samples were reported. FIG. 7C is the I-Ab-binding motif was derived from endogenous mouse peptides bound to MHCII. Heatmap shading represents the frequencies of each amino acid at each respective position.

FIG. 8—Antigen processing pathways and epitope features revealed by MHCII peptidomics.

FIG. 9—Validation of BOTA epitope predictions with MHCII peptidomics.

FIGS. 10 C, D and E show that immunodominance in vivo correlates with fold change (FC) of Listeria peptides quantified by MHCII peptidomics, and to a lesser extent, with mRNA expression (normalized microarray probe intensity) of the corresponding peptide-encoding genes.

FIG. 11—Single cell TCR sequencing defines the clonal architecture of the anti-Listeria response. Mice were inoculated with Listeria by i.p. injection. Six days later, CD4+ CD25+CD69+ T cells were FACS-sorted from spleens for single cell RNA-seq and TCRseq. FIG. 11A shows a tSNE plot derived from T cell transcriptomes identifies 3 distinct cell states that cluster according to unique signatures. Each dot represents a single cell that is color coded according to gene signature. FIG. 11B shows that TCRseq defines the CD4 T cell response to *Listeria*. Each dot represents a single cell that is shaded according to expression of Ifng. FIG. 11C shows that each dot represents a single cell that is shaded according to expression of Tbx21.

FIG. 12—Single cell RNA-seq integrates T cell phenotype with TCR repertoire in the *Listeria* response. Mice were inoculated with *Listeria* by i.p. injection on days 0 and 11. On day 18, FSC$^{HI}$CD4$^+$CD8$^-$B220$^-$MHCII$^-$ T cells were FACS-sorted from spleens for single cell RNA-seq and TCRseq. Sorted T cells were derived from 2 mice, sequenced separately, and combined for analysis.

FIG. 13—Specifying immunodominance by screening TCRs for reactivity with *Listeria* epitopes predicted by BOTA.

FIG. 14—Specifying antigen-reactivity by screening TCRs for reactivity with *Listeria* epitopes predicted by BOTA. FIG. 14A shows the screen overview. HEK 293T cells were transfected to express peptide epitopes fused in-frame with the I-A$^b$β chain bearing CD3ζ cytoplasmic domains. BW5147_CD4-28 cells were transduced to express chimeric single chain TCRs bearing the transmembrane and cytoplasmic domains of CD3ζ. In this coculture system, cognate antigen recognition results in T cell activation characterized by production of IL-2. FIG. 14B shows that the most abundant TCR identified in mice infected with *Listeria* (lmo_R6) was screened for reactivity against *Listeria* epitopes as described above. IL-2 was detected in culture supernatant by cytometric bead array. As controls, OT2 TCR (reactive with Ova) and LLO_118 TCR (reactive with LLO) were included. Shown are SEQ ID NOs: 15200-15204, from left to right. FIG. 14C shows that HEK 293T cells were transfected with constructs encoding single chain TCRs. Cells were analyzed by FACS for expression of TCRb and binding to LLO I-A$^b$ tetramers (NEKYAQAYPNVS I-A$^b$) (SEQ ID NOs: 15205).

FIG. 15—Computational prediction and validation of a dominant commensal antigen.

FIG. 19—TCR Finger-Printing.

TCRζ construct. Upon engagement of the OT2 TCR with cognate Ova(323-339) presented by MHCIIζζ, responder cells express the activation marker 41bb. Activated MHCII+ 41bb+ cells were FACS-sorted, and sequencing libraries were constructed by PCR amplification of the Ova-encoding region of lentiviral integrants.

FIG. 22—Illustrates features of immunogenicity for SusC epitopes associated with Treg reactivity in healthy mice. Shown are SEQ ID NOs: 15219-15234, starting with the top sequence.

DETAILED DESCRIPTION OF THE EXAMPLE EMBODIMENTS

General Definitions

Figure 1:
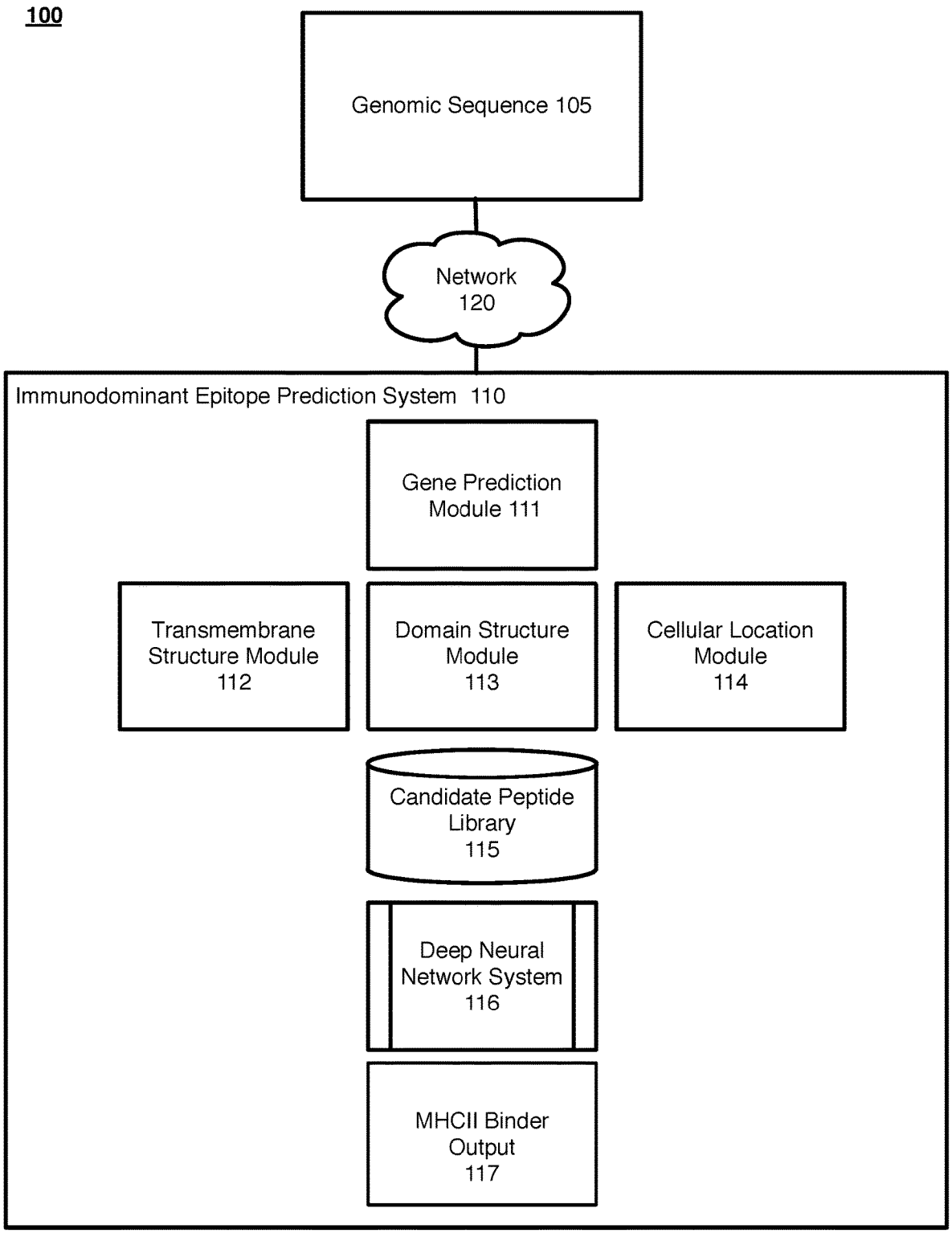
FIG. 1—block diagram depicting a system for identifying MHCII antigenic epitopes.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, $2^{nd}$ edition 2013 (E. A. Greenfield ed.); Animal Cell Culture (1987) (R. I. Freshney, ed.); Benjamin Lewin, Genes IX, published by Jones and Bartlett, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, $2^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

All publications, published patent documents, and patent applications cited in this application are indicative of the level of skill in the art(s) to which the application pertains. All publications, published patent documents, and patent applications cited herein are hereby incorporated by reference to the same extent as though each individual publication, published patent document, or patent application was specifically and individually indicated as being incorporated by reference.

Overview

Defining the immunodominance hierarchy of T cell epitopes remains a significant challenge in the context of infectious disease, commensal immunity, autoimmunity, and immune oncology. Even for some of the most widespread bacterial pathogens, little is known about which antigens drive protective CD4 T cell responses. In one aspect, embodiments herein provide computer-implemented techniques for predicting MHCII binding epitopes using sequencing data. In certain example embodiments, the sequencing data is whole genome data, whole exome sequencing data (WES), RNA-seq data, targeted exome sequencing data, or any form of sequencing data that allows gene prediction at either the exome, genome, or RNA levels. In certain example embodiments, it is not necessary to have a complete genome to identify all useful epitopes. For ease of reference, the sequencing data as described above may be used interchangeably. In certain embodiments, only 90% of a genome or 90% of an exome is required to predict MHCII binding epitopes. In certain embodiments, predictions can be made from metagenomics (i.e., genomic sequencing from a complex mixture of microbes in stool) in which coverage of any given microbe's genome may be as low as 1%. In certain embodiments, de novo predictions can be made from sequencing reads directly from metagenomics or transcriptomics without mapping to a genome (e.g., essentially 0% known genome).

As a consequence of deep profiling of the MHC II immunopeptidome, a rich dataset was generated for identifying key features of antigenicity and derivation of the computer-implemented methods disclosed herein. Accordingly, the computer-implemented methods disclosed herein incorporate several important attributes of immunodominant epitopes revealed by proteomics.

The improvement on predication accuracy of the computer-implemented methods disclosed herein also signifies the successful application of deep neural network solving to a complex biomedical problem. Previous efforts using traditional networks or hidden Markov Models were limited by their ability to extract highly abstract features, thus leading to insufficient insights into epitope prediction. The computer-implemented methods disclosed herein can be used to predict CD4 T cell epitopes for virtually any MHC II allele and any antigen source, including commensal microbes, pathogens, autoantigens, and tumor antigens. The embodiments disclosed herein demonstrate the utility of MHCII peptidomics for training a deep neural network that specifically identifies epitopes with key features associated with immunodominance. Furthermore, the embodiments disclosed herein serve as a powerful tool for unbiased discovery of complex pathogen and for interrogation of host pathways underlying human disease.

In certain embodiments, MHCII binding epitopes may be predicted using known MHCII binding motifs. The known binding motifs may be incorporated into the described systems and methods. Candidate antigens with a known binding motif may be used as input to the deep neural network system 116. In one embodiment, human HLA class II binding motifs may be used (see e.g., Andreatta and Nielsen, "Characterizing the binding motifs of 11 common human HLA-DP and HLA-DQ molecules using NNAlign" Immunology. 2012 July; 136(3): 306-311).

Turning now to FIGS. 1-6, in which like numerals represent like (but not necessarily identical) elements throughout the figures, example embodiments are described in detail.

Example Epitope Prediction System Architectures

FIG. 1 is a block diagram depicting an epitope prediction system 100 for predicting MHCII binding antigens using nucleic acid sequencing data (e.g., BOTA). As depicted in FIG. 1, the operating environment 100 includes network devices 105 and 110 that are configured to communicate with one another via one or more networks 120. In some embodiments, the genomic sequencing device 105 may provide sequencing data directly from real time sequencing reads. In other example embodiments, the genomic sequencing device comprises a storage device 106. The storage device 106 may comprise a database or be linked to a database comprising sequencing files 107. In some embodiments, a user associated with a device must install an application and/or make a feature selection to obtain the benefits of the techniques described herein. The epitope prediction system 110 receives genomic data and outputs a set of identified ranked epitopes from the sequencing data. BOTA scoring reflects the likelihood of a given epitope being immunodominant.

In certain embodiments, sequencing comprises high-throughput (formerly "next-generation") technologies to generate sequencing reads. In DNA sequencing, a read is an inferred sequence of base pairs (or base pair probabilities) corresponding to all or part of a single DNA fragment. A typical sequencing experiment involves fragmentation of the genome into millions of molecules or generating complementary DNA (cDNA) fragments, which are size-selected and ligated to adapters. The set of fragments is referred to as a sequencing library, which is sequenced to produce a set of reads. Methods for constructing sequencing libraries are known in the art (see, e.g., Head et al., Library construction for next-generation sequencing: Overviews and challenges. Biotechniques. 2014; 56(2): 61-77). In certain embodiments, the library members (e.g., genomic DNA, cDNA) may include sequencing adaptors that are compatible with use in, e.g., Illumina's reversible terminator method, Roche's pyrosequencing method (454), Life Technologies' sequencing by ligation (the SOLID platform) or Life Technologies' Ion Torrent platform. Examples of such methods are described in the following references: Margulies et al (Nature 2005 437:376-80); Ronaghi et al (Analytical Biochemistry 1996 242:84-9); Shendure et al (Science 2005 309:1728-32); Imelfort et al (Brief Bioinform. 2009 10:609-18); Fox et al (Methods Mol. Biol. 2009; 553:79-108); Appleby et al (Methods Mol. Biol. 2009; 513:19-39); and Morozova et al (Genomics. 2008 92:255-64), which are incorporated by reference for the general descriptions of the methods and the particular steps of the methods, including all starting products, reagents, and final products for each of the steps.

In certain embodiments, the present invention includes whole genome sequencing. Whole genome sequencing (also known as WGS, full genome sequencing, complete genome sequencing, or entire genome sequencing) is the process of determining the complete DNA sequence of an organism's genome at a single time. This entails sequencing all of an organism's chromosomal DNA as well as DNA contained in the mitochondria and, for plants, in the chloroplast.

In certain embodiments, the present invention includes whole exome sequencing. Exome sequencing, also known as whole exome sequencing (WES), is a genomic technique for sequencing all of the protein-coding genes in a genome (known as the exome) (see, e.g., Ng et al., 2009, Nature volume 461, pages 272-276). It consists of two steps: the first step is to select only the subset of DNA that encodes proteins. These regions are known as exons—humans have about 180,000 exons, constituting about 1% of the human genome, or approximately 30 million base pairs. The second step is to sequence the exonic DNA using any high-throughput DNA sequencing technology.

In certain embodiments, targeted sequencing is used in the present invention (see, e.g., Mantere et al., PLOS Genet 12 e1005816 2016; and Carneiro et al. BMC Genomics, 2012 13:375). Targeted gene sequencing panels are useful tools for analyzing specific mutations in a given sample. Focused panels contain a select set of genes or gene regions that have known or suspected associations with the disease or phenotype under study.

Each network device 105 and 110 includes a device having a communication module capable of transmitting and receiving data over the network 120. For example, each network device 105 and 110 can include a server, desktop computer, laptop computer, tablet computer, a television with one or more processors embedded therein and/or coupled thereto, smart phone, handheld computer, personal digital assistant ("PDA"), or any other wired or wireless, processor-driven device.

The genomic sequencing device 105 may generate sequence data files 107 comprising information on the coding regions of genes within a given biological sample. In one example embodiment, the sequencing device may directly communicate the data file to the epitope prediction system 110 across the network 120 and the epitope prediction and ranking is conducted in line with the sequencing analysis. In another example embodiment, the sequencing data file may be stored on a data storage medium and later uploaded to the epitope prediction system 110 for further analysis.

The epitope prediction system 110 may comprise a peptide prediction module 111, a epitope ranking module 113, a candidate peptide library index 112, and a candidate epitope module 114. The peptide prediction module 111 predicts protein coding genes from the input genomic sequencing data file 107 and generates a list of candidate peptides based on various selection criteria described below. In certain example embodiments, the peptide prediction module 111 stores the candidate peptides in the candidate peptide library index 112.

It will be appreciated that the network connections shown are examples and other means of establishing a communications link between the computers and devices can be used. Moreover, those having ordinary skill in the art having the benefit of the present disclosure will appreciate that the Epitope Prediction System 110, can have any of several other suitable computer system configurations.

Example Processes

Figure 2:
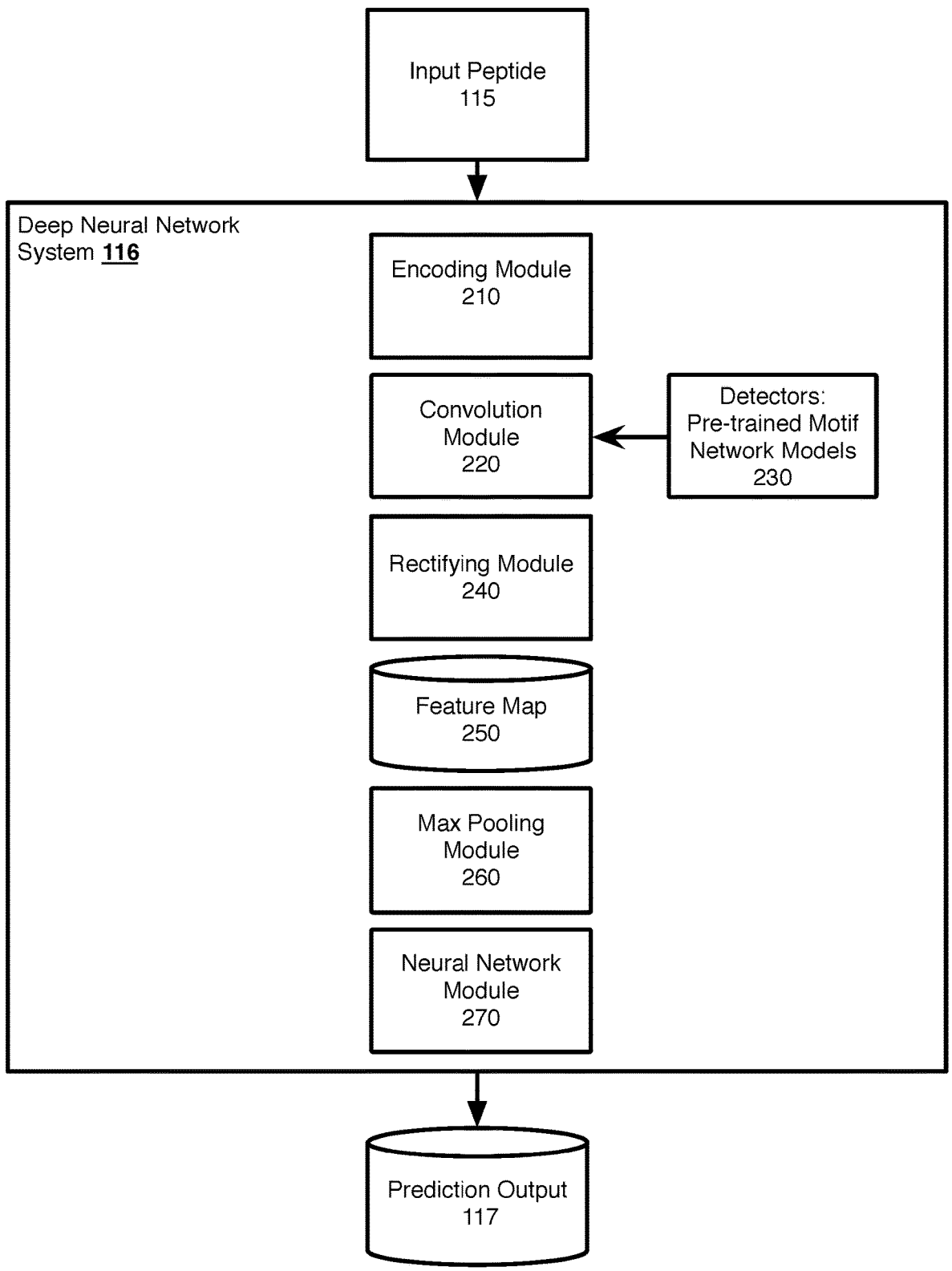
FIG. 2—block diagram depicting a system for a deep neural network for predicting binding of peptides to MHCII molecules.
Figure 3:
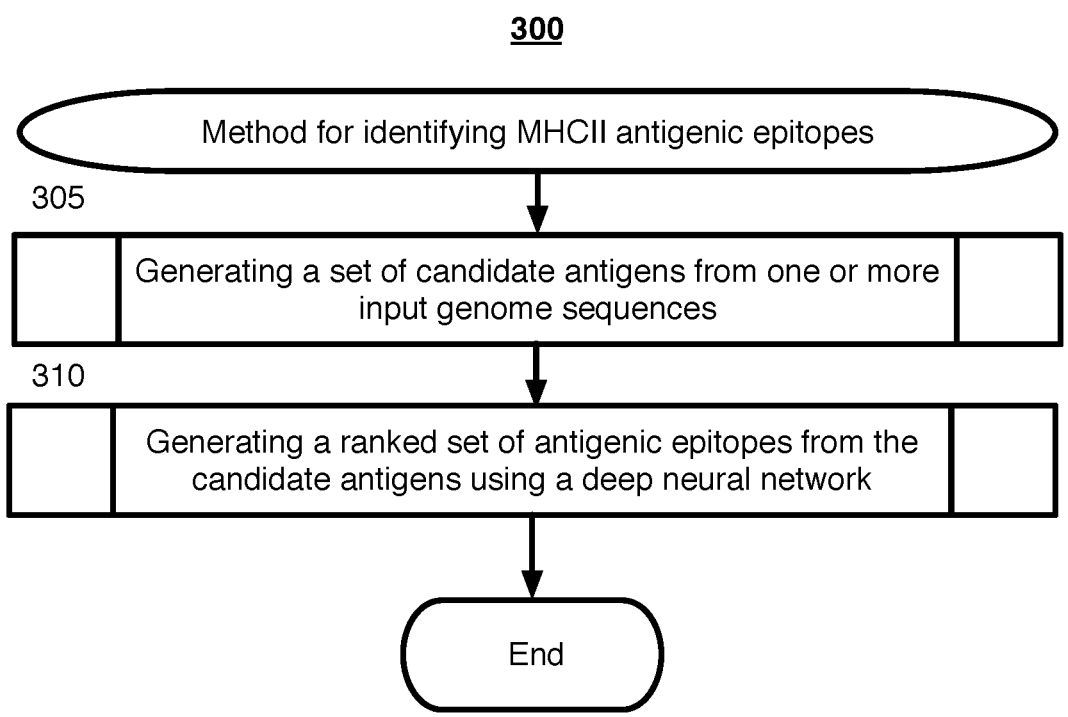
FIG. 3—block diagram depicting a method for identifying MHCII antigenic epitopes.
Figure 4:
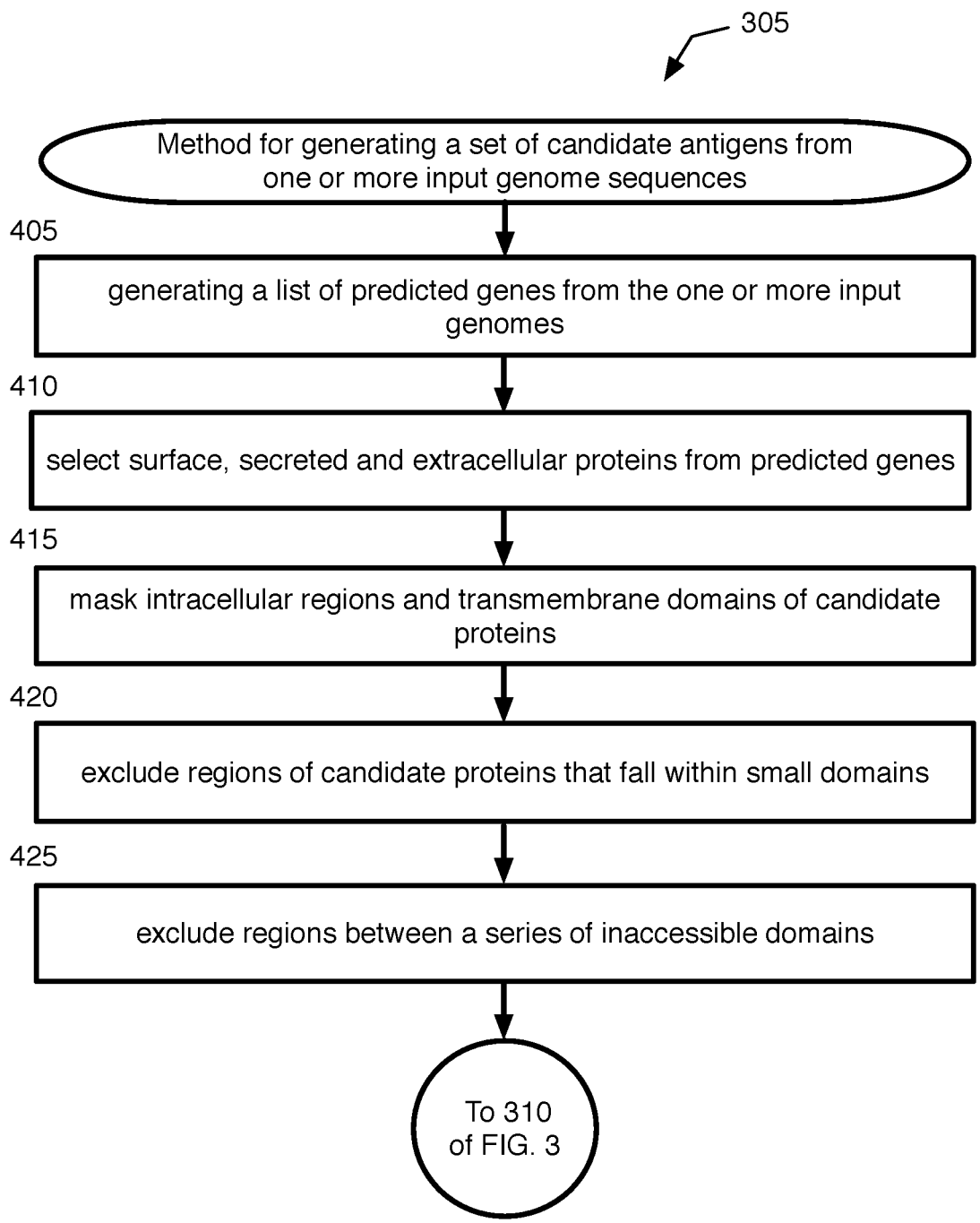
FIG. 4—block diagram depicting a method for generating a set of candidate antigens from one or more input genome sequences.

The example methods illustrated in FIGS. 2-4 are described hereinafter with respect to the components of the example operating environment 100. The example methods of FIGS. 2-4 may also be performed with other systems and in other environments.

FIG. 2 is a block flow diagram depicting a method 300 for identifying MHCII antigenic epitopes an input genome sequence, in accordance with certain example embodiments.

The input genome sequence according to any embodiment described herein may be derived from any target cell type or target pathogen. In certain embodiments, the input genome sequence may be derived from the target cell type or target pathogen exposed to a dendritic cell in any embodiment described herein. The target cell type or target pathogen may be selected from the group consisting of a bacterium, virus, protozoa, and diseased cell. The diseased cell may be a cancer cell. The cancer cell may be obtained from a subject in need thereof. The method may further comprise identifying non-silent tumor specific somatic mutations from the input genome sequence, wherein the antigenic epitopes are derived from said mutations. Not being bound by a theory, a cancer obtains non-inherited mutations that can produce non-self tumor specific mutations. The tumor specific mutations can produce tumor specific antigens that are ideal for targeting by the immune system. Identifying non-silent tumor specific somatic mutations from the input genome sequence may be determined by sequencing tumor tissue from a subject and comparing the sequence to that of non-tumor tissue from the same subject or from germline tissue from the same subject. The diseased cell may be associated with an autoimmune disease.

In certain example embodiments, the target pathogen is a bacterium. Examples of pathogenic bacteria that can be detected in accordance with the disclosed methods include without limitation any one or more of (or any combination of) *Acinetobacter baumannii*, *Actinobacillus* sp., *Actinomy-cetes*, *Actinomyces* sp. (such as *Actinomyces israelii* and *Actinomyces naeslundii*), *Aeromonas* sp. (such as *Aeromonas hydrophila*, *Aeromonas veronii* biovar *sobria* (*Aeromonas sobria*), and *Aeromonas caviae*), *Anaplasma phagocytophilum*, *Anaplasma marginale*, *Alcaligenes xylosoxidans*, *Acinetobacter baumannii*, *Actinobacillus actinomycetemcomitans*, *Bacillus* sp. (such as *Bacillus anthracis*, *Bacillus cereus*, *Bacillus subtilis*, *Bacillus thuringiensis*, and *Bacillus stearothermophilus*), *Bacteroides* sp. (such as *Bacteroides fragilis*), *Bartonella* sp. (such as *Bartonella bacilliformis*) and *Bartonella henselae*, *Bifidobacterium* sp., *Bordetella* sp. (such as *Bordetella pertussis*, *Bordetella parapertussis*, and *Bordetella bronchiseptica*), *Borrelia* sp. (such as *Borrelia recurrentis*, and *Borrelia burgdorferi*), *Brucella* sp. (such as *Brucella abortus*, *Brucella canis*, *Brucella melitensis* and *Brucella suis*), *Burkholderia* sp. (such as *Burkholderia pseudomallei* and *Burkholderia cepacia*), *Campylobacter* sp. (such as *Campylobacter jejuni*, *Campylobacter coli*, *Campylobacter lari* and *Campylobacter fetus*), *Capnocytophaga* sp., *Cardiobacterium hominis*, *Chlamydia trachomatis*, *Chlamydophila pneumoniae*, *Chlamydophila psittaci*, *Citrobacter* sp. *Coxiella burnetii*, *Corynebacterium* sp. (such as, *Corynebacterium diphtheriae*, *Corynebacterium jeikeium* and *Corynebacterium*), *Clostridium* sp. (such as *Clostridium perfringens*, *Clostridium difficile*, *Clostridium botulinum* and *Clostridium tetani*), *Eikenella corrodens*, *Enterobacter* sp. (such as *Enterobacter aerogenes*, *Enterobacter agglomerans*, *Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chaffeensis* and *Ehrlichia canis*), *Erysipelothrix rhusiopathiae*, *Eubacterium* sp., *Francisella tularensis*, *Fusobacterium nucleatum*, *Gardnerella vaginalis*, *Gemella morbillorum*, *Haemophilus* sp. (such as *Haemophilus influenzae*, *Haemophilus ducreyi*, *Haemophilus aegyptius*, *Haemophilus parainfluenzae*, *Haemophilus haemolyticus* and *Haemophilus parahaemolyticus*), *Helicobacter* sp. (such as *Helicobacter pylori*, *Helicobacter cinaedi* and *Helicobacter fennelliae*), *Kingella kingae*, *Klebsiella* sp. (such as *Klebsiella pneumoniae*, *Klebsiella granulomatis* and *Klebsiella oxytoca*), *Lactobacillus* sp., *Listeria monocytogenes*, *Leptospira interrogans*, *Legionella pneumophila*, *Leptospira interrogans*, *Peptostreptococcus* sp., *Mannheimia haemolytica*, *Moraxella catarrhalis*, *Morganella* sp., *Mobiluncus* sp., *Micrococcus* sp., *Mycobacterium* sp. (such as *Mycobacterium leprae*, *Mycobacterium tuberculosis*, *Mycobacterium paratuberculosis*, *Mycobacterium intracellulare*, *Mycobacterium avium*, *Mycobacterium bovis*, and *Mycobacterium marinum*), *Mycoplasma* sp. (such as *Mycoplasma pneumoniae*, *Mycoplasma hominis*, and *Mycoplasma genitalium*), *Nocardia* sp. (such as *Nocardia asteroides*, *Nocardia cyriacigeorgica* and *Nocardia brasiliensis*), *Neisseria* sp. (such as *Neisseria gonorrhoeae* and *Neisseria meningitidis*), *Pasteurella multocida*, *Plesiomonas shigelloides*. *Prevotella* sp., *Porphyromonas* sp., *Prevotella melaninogenica*, *Proteus* sp. (such as *Proteus vulgaris* and *Proteus mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp.

(such as *Salmonella enterica, Salmonella typhi, Salmonella paratyphi, Salmonella enteritidis, Salmonella choleraesuis* and *Salmonella typhimurium*), *Serratia* sp. (such as *Serratia marcescens* and *Serratia liquefaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus haemolyticus Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes*, Group A streptococci, *Streptococcus pyogenes*, Group B streptococci, *Streptococcus agalactiae*, Group C streptococci, *Streptococcus anginosus, Streptococcus equisimilis*, Group D streptococci, *Streptococcus bovis*, Group F streptococci, and *Streptococcus anginosus* Group G streptococci), Spirillum minus, *Streptobacillus moniliformis, Treponema* sp. (such as *Treponema carateum, Treponema pertenue, Treponema pallidum* and *Treponema endemicum, Tropheryma whippelii, Ureaplasma urealyticum, Veillonella* sp., *Vibrio* sp. (such as *Vibrio cholerae, Vibrio vulnificus, Vibrio parahaemolyticus, Vibrio vulnificus, Vibrio alginolyticus, Vibrio mimicus, Vibrio hollisae, Vibrio fluvialis, Vibrio metschnikovii, Vibrio damsela* and *Vibrio furnissii*), *Yersinia* sp. (such as *Yersinia enterocolitica, Yersinia pestis*, and *Yersinia pseudotuberculosis*) and *Xanthomonas maltophilia* among others.

In certain example embodiments, the target pathogen is a fungus. Examples of fungi that can be detected in accordance with the disclosed methods include without limitation any one or more of (or any combination of), *Aspergillus, Blastomyces, Candidiasis, Coccidioidomycosis, Cryptococcus neoformans, Cryptococcus gattii, Histoplasma, Mucormycosis, Pneumocystis, Sporothrix*, fungal eye infections ringwork, *Exserohilum*, and *Cladosporium*.

In certain example embodiments, the fungus is a yeast. Examples of yeast that can be detected in accordance with disclosed methods include without limitation one or more of (or any combination of), *Aspergillus* species, a *Geotrichum* species, a *Saccharomyces* species, a *Hansenula* species, a *Candida* species, a *Kluyveromyces* species, a *Debaryomyces* species, a *Pichia* species, or combination thereof. In certain example embodiments, the fungus is a mold. Example molds include, but are not limited to, a *Penicillium* species, a *Cladosporium* species, a *Byssochlamys* species, or a combination thereof.

In certain example embodiments, the target pathogen may be a virus. The virus may be a DNA virus, a RNA virus, or a retrovirus. Example of RNA viruses that may be detected include one or more of (or any combination of) Coronaviridae virus, a Picornaviridae virus, a Caliciviridae virus, a Flaviviridae virus, a Togaviridae virus, a Bornaviridae, a Filoviridae, a Paramyxoviridae, a Pneumoviridae, a Rhabdoviridae, an Arenaviridae, a Bunyaviridae, an Orthomyxoviridae, or a Deltavirus. In certain example embodiments, the virus is Coronavirus, SARS, Poliovirus, Rhinovirus, Hepatitis A, Norwalk virus, Yellow fever virus, West Nile virus, Hepatitis C virus, Dengue fever virus, Zika virus, Rubella virus, Ross River virus, Sindbis virus, Chikungunya virus, Borna disease virus, Ebola virus, Marburg virus, Measles virus, Mumps virus, Nipah virus, Hendra virus, Newcastle disease virus, Human respiratory syncytial virus, Rabies virus, Lassa virus, Hantavirus, Crimean-Congo hemorrhagic fever virus, Influenza, or Hepatitis D virus.

In certain example embodiments, the virus may be a retrovirus. Example retroviruses that may be detected using the embodiments disclosed herein include one or more of or any combination of viruses of the Genus Alpharetrovirus, Betaretrovirus, Gammaretrovirus, Deltaretrovirus, Epsilonretrovirus, Lentivirus, Spumavirus, or the Family Metaviridae, Pseudoviridae, and Retroviridae (including HIV), Hepadnaviridae (including Hepatitis B virus), and Caulimoviridae (including Cauliflower mosaic virus).

In certain example embodiments, the virus is a DNA virus. Example DNA viruses that may be detected using the embodiments disclosed herein include one or more of (or any combination of) viruses from the Family Myoviridae, Podoviridae, Siphoviridae, Alloherpesviridae, Herpesviridae (including human herpes virus, and Varicella Zoster virus), Malocoherpesviridae, Lipothrixviridae, Rudiviridae, Adenoviridae, Ampullaviridae, Ascoviridae, Asfarviridae (including African swine fever virus), Baculoviridae, Cicaudaviridae, Clavaviridae, Corticoviridae, Fuselloviridae, Globuloviridae, Guttaviridae, Hytrosaviridae, Iridoviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae (including Simian virus 40, JC virus, BK virus), Poxviridae (including Cowpox and smallpox), Sphaerolipoviridae, Tectiviridae, Turriviridae, Dinodnavirus, Salterprovirus, Rhizidovirus, among others.

In certain example embodiments, the target pathogen may be a protozoon. Examples of protozoa include without limitation any one or more of (or any combination of), Euglenozoa, Heterolobosea, Diplomonadida, Amoebozoa, *Blastocystis*, and Apicomplexa. Example Euglenozoa include, but are not limited to, *Trypanosoma cruzi* (Chagas disease), *T. brucei* gambiense, *T. brucei* rhodesiense, *Leishmania braziliensis, L. infantum, L. mexicana, L. major, L. tropica*, and *L. donovani*. Example Heterolobosea include, but are not limited to, *Naegleria fowleri*. Example Diplomonadid include, but are not limited to, Giardia intestinalis (*G. lamblia, G. duodenalis*). Example Amoebozoa include, but are not limited to, *Acanthamoeba castellanii, Balamuthia mandrillaris, Entamoeba histolytica*. Example *Blastocystis* include, but are not limited to, *Blastocystis hominis*. Example Apicomplexa include, but are not limited to, *Babesia microti, Cryptosporidium parvum, Cyclospora cayetanensis, Plasmodium falciparum, P. vivax, P. ovale, P. malariae*, and *Toxoplasma gondii*.

In certain example embodiments, the target epitopes are present on a commensal microorganism. The Human Microbiome Project sequenced the genome of the human microbiota, focusing particularly on the microbiota that normally inhabit the skin, mouth, nose, digestive tract, and vagina (see, e.g., hmpdacc.org/hmp/). MHCII epitopes may be predicted any of the microorganisms described.

The four dominant bacterial phyla in the human gut are Firmicutes, Bacteroidetes, Actinobacteria, and Proteobacteria. Most bacteria belong to the genera *Bacteroides, Clostridium, Faecalibacterium, Eubacterium, Ruminococcus, Peptococcus, Peptostreptococcus*, and *Bifidobacterium*. Other genera, such as *Escherichia* and *Lactobacillus*, are present to a lesser extent. Species from the genus *Bacteroides* alone constitute about 30% of all bacteria in the gut, suggesting that this genus is especially important in the functioning of the host.

Fungal genera that have been detected in the gut include *Candida, Saccharomyces, Aspergillus, Penicillium, Rhodotorula, Trametes, Pleospora, Sclerotinia, Bullera*, and *Galactomyces*, among others. *Rhodotorula* is most frequently found in individuals with inflammatory bowel disease while *Candida* is most frequently found in individuals with hepatitis B cirrhosis and chronic hepatitis B.

Archaea constitute another large class of gut flora which are important in the metabolism of the bacterial products of fermentation.

A number of types of bacteria, such as *Actinomyces viscosus* and *A. naeslundii*, live in the mouth.

The vaginal microflora consists mostly of various *lactobacillus* species (e.g., *Lactobacillus acidophilus, L. iners, L. crispatus, L. jensenii, L. delbrueckii* and *L. gasseri*).

In certain example embodiments, the target epitopes are present on an allergen. As used herein the term "allergen" may refer to an antigen, microorganism, plant, or product thereof that produces an abnormal immune response in which the immune system fights off a perceived threat that would otherwise be harmless to the body. Allergens can be found in a variety of sources (e.g., animal products, foods, insects, mold spores, plants and chemicals). Allergens can include, but are not limited to dust mite, pollen, spores, poison ivy, poison oak, pet dander, royal jelly, peanuts (a legume), nuts, insect bites or stings, seafood and shellfish.

Method 200 begins at block 205, wherein a set of candidate antigens are generated from an input genome sequence. Turning to FIG. 3, the process of generating a set of candidate peptides from one or more input genome sequences is described in more detail.

Method 205 begin at block 305, where a set of predicted gens is generated from one or more genome input sequences, such as from genomic sequence input files 107. Predicted genes may be identified using various gene prediction methodologies. The gene prediction may be ab initio including both signal-based and content-based approaches. In certain example embodiments, the gene prediction methodology is a hidden Markov model (HMM)-based method, or machine learning based, including neural network based approaches. Example gene prediction algorithms that may be used include, but are not limited to, GLIMMER, GeneMark, GENSCAN, geneid, SNAP, mSplicer, CONTRAST, or GENE. Methods that combine pattern recognition and machine learning such as Maker and Augustus may also be used. Other methods may include comparative genomic approaches, such as those employed by TWINSCAN, N-SCAN, and CONTRAST, may be used. Additional example gene prediction methods are disclosed in Mathe et al. Nucleic Acids Research (2002) 30(19):4103-4117.

At block 310, the gene prediction module 111 then reduces the predicted gene set by selecting only those genes that are identified as producing protein products that are located on the cell surface or are secreted as extracellular proteins. An example method for predicting subcellular localization include PSORTb 3.0 as described in Yu et al. Bioinformatics 26, 1608-1615 (2010). Other similar and known computer-based subcellular localization prediction methods may also be used.

At block 315, the peptide prediction module 111 then takes the sub-set of identified cell-surface and extracellular proteins and mask any intracellular regions and transmembrane domains in the identified subset. Methods for protein topology recognition that may be applied included those described in Tusnady et al. Journal of Molecular Biology 283:489-506 (1998). Similar and other known topology prediction methods may be used. In certain example embodiments, the masked region may be expanded to include a flanking buffer region around the identify intracellular and transmembrane domains. The flanking region may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid in either or both of the N- or C-terminal directions from the intracellular region or transmembrane domain. Not being bound by a theory, the flanking region may be differentially accessible based on specific antigens (e.g., antigens in the training set) and the flanking regions either increased or decreased.

At block 320, the peptide prediction module 111, then excludes from further analysis, regions of the candidate proteins that fall within small domains or between a series of domains. The metric used for domain mapping may include the distance to the upstream/downstream domains, the density of flanking domains and the size of the domain. In certain example embodiments, a small domain is a domain of 30 or fewer amino acids. In certain other example embodiments, a region of a candidate protein is excluded if it falls within 8 amino acids of a small domain. In other example embodiments, a region of a candidate protein is excluded if it falls within a series of domains. In certain embodiments, a region of a candidate protein is excluded if it falls within an interdomain region of 20 amino acids or less. Regions of the candidate proteins may be excluded based on one or more of the above criteria. The final result is a data file comprising a list of candidate antigens from each candidate protein. The candidate antigens are those portions of the candidate proteins that remain after all of the exclusion and masking steps above are completed. The candidate antigen data file may be stored in the candidate antigen library 112. The method then returns to block 210 of FIG. 2.

At block 210 of FIG. 2, the epitope ranking module 113 then takes the candidate antigens as input and proceeds to generate a list of ranked candidate epitopes. Many factors contribute to the score for ranking (e.g., MHC binding, cellular localization, protein topology, domain architecture). The process is described in more detail with reference to FIG. 4.

Method 210 begins at block 405 of FIG. 4, wherein the epitope ranking module 113 encodes each amino acid of each candidate antigen into a p-dimensional binary vector b with half of the vector elements being 1 and the rest being 0, chosen at random.

At block 410, the epitope ranking module 113 coverts each a p-dimensional binary vector b into a descriptor matrix S. Therefore, given a peptide with length l longer than k, it is first converted to an l×b descriptor matrix S, in which $S_{ij}=1$ if the i-th amino acid's l-valued indices overlap with j, otherwise $S_{ij}=0$. The matrix S is then normalized by row sum to become S' such that $$S_{ij}'=S_{ij}/\Sigma_{j=1}^{b}S_{ij}$$

At block 415, the epitope ranking module 113 then convolutes S' into a (1−k+1)×d matrix X, where d is the number of pre-trained motif network models within the overall model and k is the length of such binding cores. $X_{ij}$ represents the score of motif network model j aligned to position i. The cohort of motif network models is arranged in a d×k×b array H with $H_{ijk}$ being the d-th motif network model aligned to the k-th position of the b-th set of amino acids. This sequence conversion and convolution setup is similar to model developed by Alipanahi et al. (Alipanahi et al., 2015). Methods for generating pre-trained motif network models are described in further detail below.

At block 420, the epitope ranking module 113 then transforms the scoring matrix X into a d-dimensional vector Z, wherein vector Z is input for neural network analysis and ranking of epitopes. The output of the neural network is a list of scored epitopes. In certain example embodiments, the epitopes may be ranked by immunodominance. In certain example embodiments, the convoluted matrix X, it is filtered with a max-rectified linear unit (ReLU) layer, and the rectified matrix Y is then fed into a max pooling stage to be transformed into d-dimensional vector Z, in which, $$z_j = \max(Y_{1j}, Y_{2j}, \ldots, Y_{nj})$$

This d-dimensional vector Z is then used as input for a neural network with a Maxout dropout model. Z is then used as the input for a standard output layer for final prediction calculation. While not being bound by the following theory, the method minimizes the prediction error as measured 1 by 1-norm distance of all the peptides. In one embodiment, the back propagation with stochastic gradient descent (SGD) method using mini batch size at 64 may be used to reach optimal weights. To train the weights, mouse epitope peptides may be used as a training set of true positive peptides. In silico true negative peptides may also be used as a training set by surveying an equal number of peptides that are not part of the peptidomics data readout at random.

Figure 6:
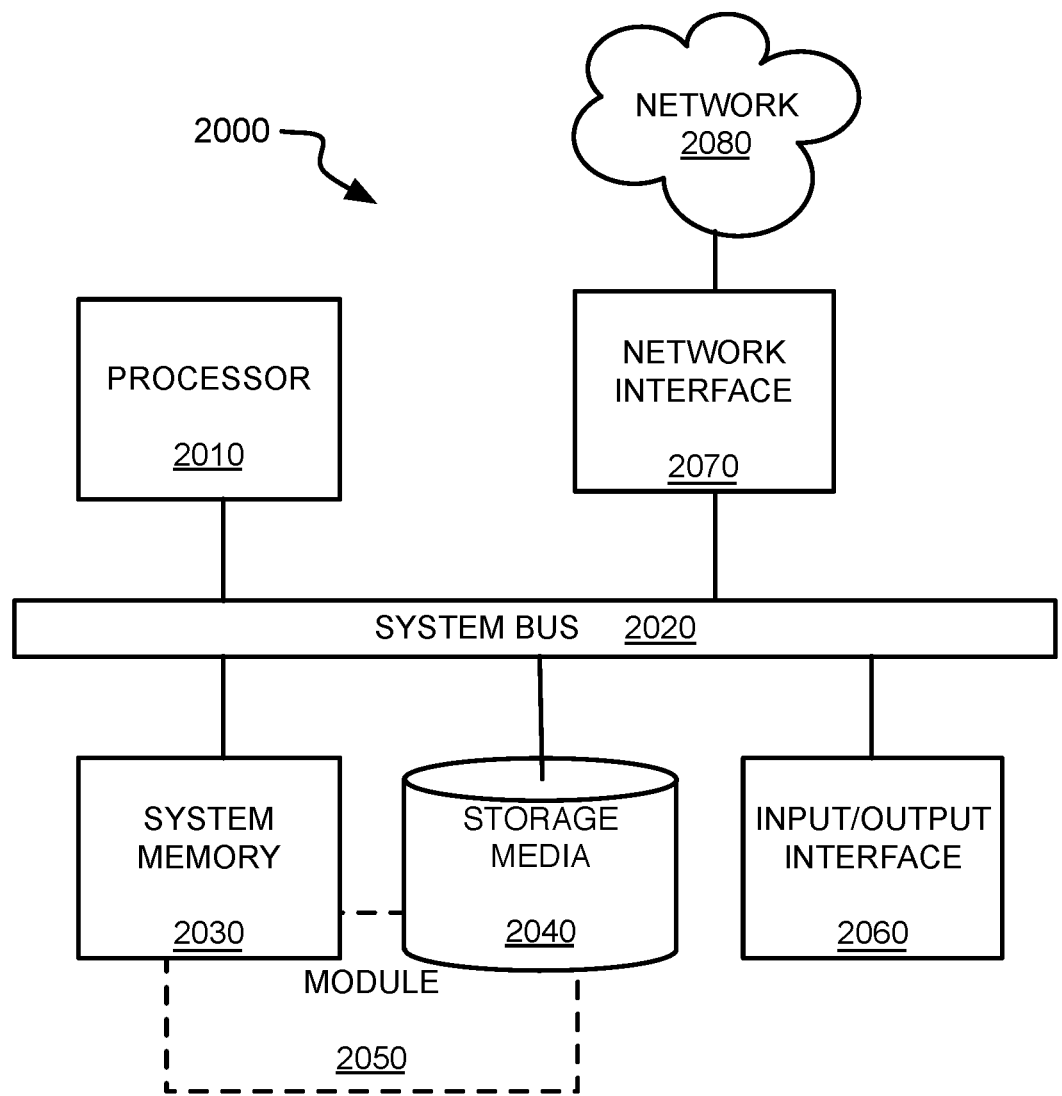
FIG. 6—block diagram depicting a computing machine and a module, in accordance with certain example embodiments.

In one embodiment, a neural network is trained by a method comprising exposing dendritic or antigen presenting cells to a pool of potential binding antigens. In certain embodiments, the pool includes non-self-antigens. In preferred embodiments, the pool of potential antigens is derived from a target pathogen or cell type. Not being bound by a theory, exposure of the dendritic or antigen presenting cells to the target pathogen or cell type allows for the determination of improved binding parameters for MHCII molecules because non-self-binding peptides may bind with higher affinity. The dendritic cells may be lysed and MHCII-peptide complexes may be isolated using an affinity reagent specific for the MHCII molecule. In preferred embodiments, antibodies are used. The antibodies may be bound to a solid support, such as, but not limited to magnetic beads or protein A or G beads. Upon isolation of the MHCII-peptide complexes, the bound peptides may be determined by protein sequencing, such as, but not limited to mass spectrometry or Edman degradation. The peptides may include peptides originating from the target pathogen or cell type and may also include peptides originating from the dendritic cell or antigen presenting host organism. The dendritic cells or antigen presenting cells may originate from a mammalian host organism, such as, but not limited to a human or mouse host organism. The bound peptides may be used for generating detectors in block 230 by testing randomly initialized parameters for the peptides. Such parameters may include, but are not limited to, amino acid sequence or net charge of peptide. The parameters may be tested in a three-fold cross validation scheme. Sets of randomly selected parameters may be tested and the best performing set provided to the deep neural network. In certain embodiments, more than 10, 20, 30, or 40, preferably about 30 parameter sets are constructed. The sets may include more than 10, 20, 30, or 40, preferably about 30 parameters. Based on the parameters most consistent with the identified peptides a set is selected. The optimal parameters may be identified by having the optimal ROC AUC score. The selected training parameters are provided to the deep neural network 116 for predicting unknown binding peptides from a genome sequence. FIG. 6 provides an example experimental work flow for identifying peptides which may then be used to train neural networks in accordance with the embodiments disclosed herein. The experimental work flow is described in greater detail in the Examples below.

Other Example Computer Embodiments

Figure 5:
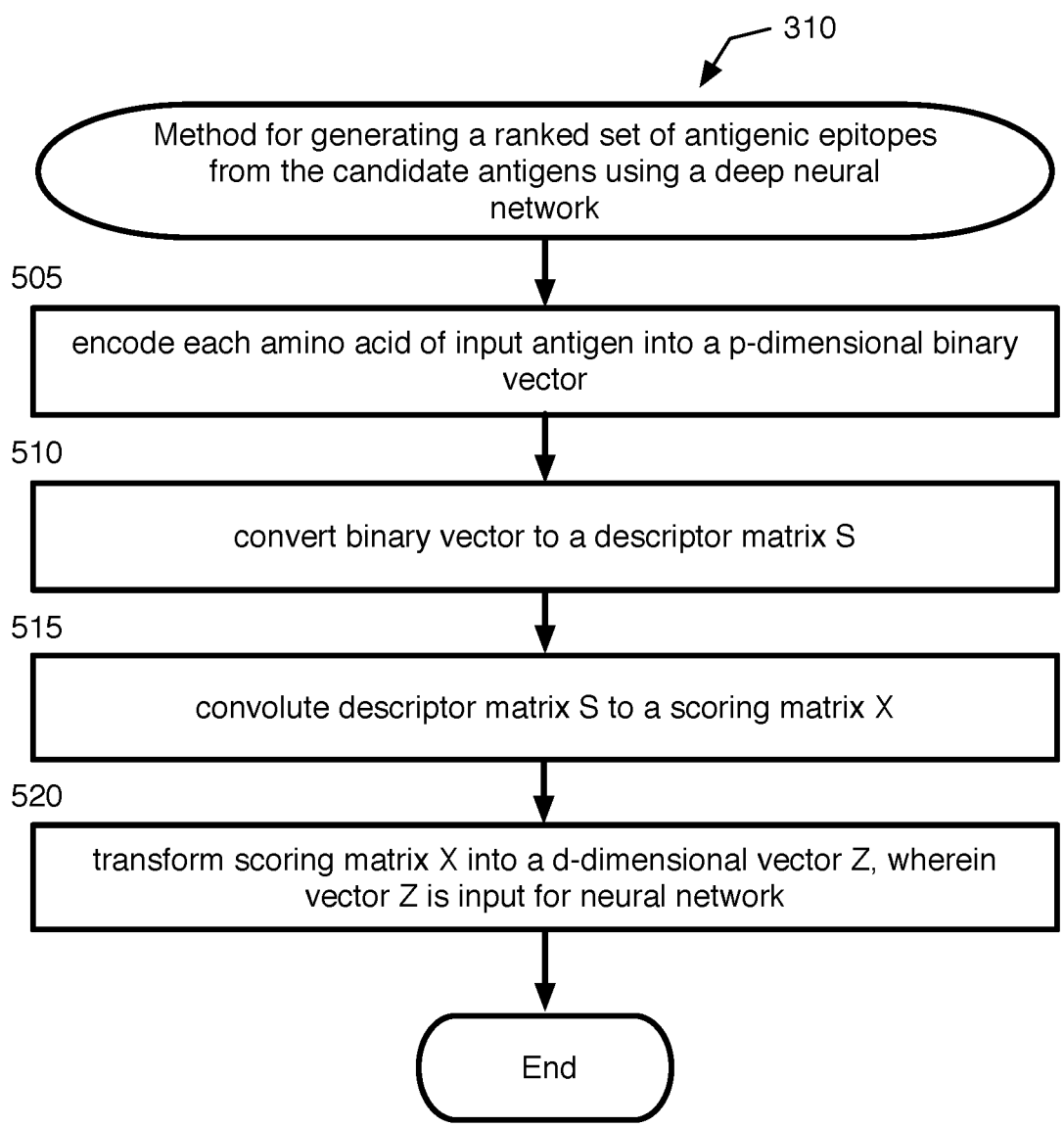
FIG. 5—block diagram depicting a method for generating a ranked set of antigenic epitopes from the candidate antigens using a deep neural network.

FIG. 5 depicts a computing machine 2000 and a module 2050 in accordance with certain example embodiments. The computing machine 2000 may correspond to any of the various computers, servers, mobile devices, embedded systems, or computing systems presented herein. The module 2050 may comprise one or more hardware or software elements configured to facilitate the computing machine 2000 in performing the various methods and processing functions presented herein. The computing machine 2000 may include various internal or attached components such as a processor 2010, system bus 2020, system memory 2030, storage media 2040, input/output interface 2060, and a network interface 2070 for communicating with a network 2080.

The computing machine 2000 may be implemented as a conventional computer system, an embedded controller, a laptop, a server, a mobile device, a smartphone, a set-top box, a kiosk, a vehicular information system, one more processors associated with a television, a customized machine, any other hardware platform, or any combination or multiplicity thereof. The computing machine 2000 may be a distributed system configured to function using multiple computing machines interconnected via a data network or bus system.

The processor 2010 may be configured to execute code or instructions to perform the operations and functionality described herein, manage request flow and address mappings, and to perform calculations and generate commands. The processor 2010 may be configured to monitor and control the operation of the components in the computing machine 2000. The processor 2010 may be a general purpose processor, a processor core, a multiprocessor, a reconfigurable processor, a microcontroller, a digital signal processor ("DSP"), an application specific integrated circuit ("ASIC"), a graphics processing unit ("GPU"), a field programmable gate array ("FPGA"), a programmable logic device ("PLD"), a controller, a state machine, gated logic, discrete hardware components, any other processing unit, or any combination or multiplicity thereof. The processor 2010 may be a single processing unit, multiple processing units, a single processing core, multiple processing cores, special purpose processing cores, co-processors, or any combination thereof. According to certain embodiments, the processor 2010 along with other components of the computing machine 2000 may be a virtualized computing machine executing within one or more other computing machines.

The system memory 2030 may include non-volatile memories such as read-only memory ("ROM"), programmable read-only memory ("PROM"), erasable programmable read-only memory ("EPROM"), flash memory, or any other device capable of storing program instructions or data with or without applied power. The system memory 2030 may also include volatile memories such as random access memory ("RAM"), static random access memory ("SRAM"), dynamic random access memory ("DRAM"), and synchronous dynamic random access memory ("SDRAM"). Other types of RAM also may be used to implement the system memory 2030. The system memory 2030 may be implemented using a single memory module or multiple memory modules. While the system memory 2030 is depicted as being part of the computing machine 2000, one skilled in the art will recognize that the system memory 2030 may be separate from the computing machine 2000 without departing from the scope of the subject technology. It should also be appreciated that the system memory 2030 may include, or operate in conjunction with, a non-volatile storage device such as the storage media 2040.

The storage media 2040 may include a hard disk, a floppy disk, a compact disc read only memory ("CD-ROM"), a digital versatile disc ("DVD"), a Blu-ray disc, a magnetic tape, a flash memory, other non-volatile memory device, a solid state drive ("SSD"), any magnetic storage device, any optical storage device, any electrical storage device, any semiconductor storage device, any physical-based storage device, any other data storage device, or any combination or multiplicity thereof. The storage media 2040 may store one or more operating systems, application programs and program modules such as module 2050, data, or any other information. The storage media 2040 may be part of, or connected to, the computing machine 2000. The storage media 2040 may also be part of one or more other computing machines that are in communication with the computing machine 2000 such as servers, database servers, cloud storage, network attached storage, and so forth.

The module 2050 may comprise one or more hardware or software elements configured to facilitate the computing machine 2000 with performing the various methods and processing functions presented herein. The module 2050 may include one or more sequences of instructions stored as software or firmware in association with the system memory 2030, the storage media 2040, or both. The storage media 2040 may therefore represent examples of machine or computer readable media on which instructions or code may be stored for execution by the processor 2010. Machine or computer readable media may generally refer to any medium or media used to provide instructions to the processor 2010. Such machine or computer readable media associated with the module 2050 may comprise a computer software product. It should be appreciated that a computer software product comprising the module 2050 may also be associated with one or more processes or methods for delivering the module 2050 to the computing machine 2000 via the network 2080, any signal-bearing medium, or any other communication or delivery technology. The module 2050 may also comprise hardware circuits or information for configuring hardware circuits such as microcode or configuration information for an FPGA or other PLD.

The input/output ("I/O") interface 2060 may be configured to couple to one or more external devices, to receive data from the one or more external devices, and to send data to the one or more external devices. Such external devices along with the various internal devices may also be known as peripheral devices. The I/O interface 2060 may include both electrical and physical connections for operably coupling the various peripheral devices to the computing machine 2000 or the processor 2010. The I/O interface 2060 may be configured to communicate data, addresses, and control signals between the peripheral devices, the computing machine 2000, or the processor 2010. The I/O interface 2060 may be configured to implement any standard interface, such as small computer system interface ("SCSI"), serial-attached SCSI ("SAS"), fiber channel, peripheral component interconnect ("PCI"), PCI express (PCIe), serial bus, parallel bus, advanced technology attached ("ATA"), serial ATA ("SATA"), universal serial bus ("USB"), Thunderbolt, FireWire, various video buses, and the like. The I/O interface 2060 may be configured to implement only one interface or bus technology. Alternatively, the I/O interface 2060 may be configured to implement multiple interfaces or bus technologies. The I/O interface 2060 may be configured as part of, all of, or to operate in conjunction with, the system bus 2020. The I/O interface 2060 may include one or more buffers for buffering transmissions between one or more external devices, internal devices, the computing machine 2000, or the processor 2010.

The I/O interface 2060 may couple the computing machine 2000 to various input devices including mice, touch-screens, scanners, biometric readers, electronic digitizers, sensors, receivers, touchpads, trackballs, cameras, microphones, keyboards, any other pointing devices, or any combinations thereof. The I/O interface 2060 may couple the computing machine 2000 to various output devices including video displays, speakers, printers, projectors, tactile feedback devices, automation control, robotic components, actuators, motors, fans, solenoids, valves, pumps, transmitters, signal emitters, lights, and so forth.

The computing machine 2000 may operate in a networked environment using logical connections through the network interface 2070 to one or more other systems or computing machines across the network 2080. The network 2080 may include wide area networks (WAN), local area networks (LAN), intranets, the Internet, wireless access networks, wired networks, mobile networks, telephone networks, optical networks, or combinations thereof. The network 2080 may be packet switched, circuit switched, of any topology, and may use any communication protocol. Communication links within the network 2080 may involve various digital or an analog communication media such as fiber optic cables, free-space optics, waveguides, electrical conductors, wireless links, antennas, radio-frequency communications, and so forth.

The processor 2010 may be connected to the other elements of the computing machine 2000 or the various peripherals discussed herein through the system bus 2020. It should be appreciated that the system bus 2020 may be within the processor 2010, outside the processor 2010, or both. According to some embodiments, any of the processor 2010, the other elements of the computing machine 2000, or the various peripherals discussed herein may be integrated into a single device such as a system on chip ("SOC"), system on package ("SOP"), or ASIC device.

Embodiments may comprise a computer program that embodies the functions described and illustrated herein, wherein the computer program is implemented in a computer system that comprises instructions stored in a machine-readable medium and a processor that executes the instructions. However, it should be apparent that there could be many different ways of implementing embodiments in computer programming, and the embodiments should not be construed as limited to any one set of computer program instructions. Further, a skilled programmer would be able to write such a computer program to implement an embodiment of the disclosed embodiments based on the appended flow charts and associated description in the application text. Therefore, disclosure of a particular set of program code instructions is not considered necessary for an adequate understanding of how to make and use embodiments. Further, those skilled in the art will appreciate that one or more aspects of embodiments described herein may be performed by hardware, software, or a combination thereof, as may be embodied in one or more computing systems. Moreover, any reference to an act being performed by a computer should not be construed as being performed by a single computer as more than one computer may perform the act.

The example embodiments described herein can be used with computer hardware and software that perform the methods and processing functions described herein. The systems, methods, and procedures described herein can be embodied in a programmable computer, computer-executable software, or digital circuitry. The software can be stored on computer-readable media. For example, computer-readable media can include a floppy disk, RAM, ROM, hard disk, removable media, flash memory, memory stick, optical media, magneto-optical media, CD-ROM, etc. Digital circuitry can include integrated circuits, gate arrays, building block logic, field programmable gate arrays (FPGA), etc.

Immunogenic Compositions

The present invention provides for predicting MHCII binding epitopes useful in formulating an immunogenic composition. The immunogenic composition may be used in the treatment of a patient in need thereof. The immunogenic composition may be a protective or tolerizing vaccine. In preferred embodiments, the immunogenic composition activates CD4+ T cells to generate a humoral immune response. In certain embodiments, the peptides enhance a CD8+ CTL response. A tolerizing vaccine may be formulated with antigenic epitopes specific for an allergen or for an autoimmunity antigen. A protective vaccine may be formulated with antigenic epitopes specific for a pathogen or for a cancer cell.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The immune system can be classified into two functional subsystems: the innate and the acquired immune system. The innate immune system is the first line of defense against infections, and most potential pathogens are rapidly neutralized by this system before they can cause, for example, a noticeable infection. The acquired immune system reacts to molecular structures, referred to as antigens, of the intruding organism. There are two types of acquired immune reactions, which include the humoral immune reaction and the cell-mediated immune reaction. In the humoral immune reaction, antibodies secreted by B cells into bodily fluids bind to pathogen-derived antigens, leading to the elimination of the pathogen through a variety of mechanisms, e.g. complement-mediated lysis. In the cell-mediated immune reaction, T-cells capable of destroying other cells are activated. For example, if proteins associated with a disease are present in a cell, they are fragmented proteolytically to peptides within the cell. Specific cell proteins then attach themselves to the antigen or peptide formed in this manner and transport them to the surface of the cell, where they are presented to the molecular defense mechanisms, in particular T-cells, of the body. Cytotoxic T cells recognize these antigens and kill the cells that harbor the antigens.

The molecules that transport and present peptides on the cell surface are referred to as proteins of the major histocompatibility complex (MHC). MHC proteins are classified into two types, referred to as MHC class I and MHC class II. The structures of the proteins of the two MHC classes are very similar; however, they have very different functions. Proteins of MHC class I are present on the surface of almost all cells of the body, including most tumor cells. MHC class I proteins are loaded with antigens that usually originate from endogenous proteins or from pathogens present inside cells, and are then presented to naïve or cytotoxic T-lymphocytes (CTLs). MHC class II proteins are present on dendritic cells (DC), B-lymphocytes, macrophages and other antigen-presenting cells (APC). They mainly present peptides, which are processed from external antigen sources, i.e. outside of the cells, to T-helper (Th) cells.

Most of the peptides bound by the MHC class I proteins originate from cytoplasmic proteins produced in the healthy host cells of an organism itself, and do not normally stimulate an immune reaction. Accordingly, cytotoxic T-lymphocytes that recognize such self-peptide-presenting MHC molecules of class I are deleted in the thymus (central tolerance) or, after their release from the thymus, are deleted or inactivated, i.e. tolerized (peripheral tolerance). MHC molecules are capable of stimulating an immune reaction when they present peptides to non-tolerized T-lymphocytes. Cytotoxic T-lymphocytes have both T-cell receptors (TCR) and CD8 molecules on their surface. T-Cell receptors are capable of recognizing and binding peptides complexed with the molecules of MHC class I. Each cytotoxic T-lymphocyte expresses a unique T-cell receptor which is capable of binding specific MHC/peptide complexes.

MHC Class II molecules are required for the activation of CD4+ T cells. CD4+ T cells depend mainly on infiltrating APCs that either pick up available antigens or engulf tumor cells or pathogens. The MHC Class II antigen presentation pathway can be targeted in an immunotherapy (see e.g., Thibodeau, et al., Targeting the MHC Class II antigen presentation pathway in cancer immunotherapy. Oncoimmunology. 2012 Sep. 1; 1(6):908-916). Antigens can gain access to MHC Class II-loading compartments by multiple distinct means. For example, transmembrane proteins from the plasma membrane can be endocytosed and sent to lysosomes for degradation. Phagocytosis is also a mechanism antigens can gain access to MHC Class II loading compartments. For example, when a macrophage ingests a pathogenic microorganism, or cancer cell the pathogen or cancer cell becomes trapped in a phagosome which then fuses with a lysosome to form a phagolysosome. Within the phagolysosome, enzymes and toxic peroxides digest the pathogen or cancer cell. Cytoplasmic and nuclear antigens can also be engulfed by autophagy.

In certain embodiments, a subject is administered an immunogenic composition comprising the antigenic epitopes of the present invention. In one embodiment, the peptides of the present invention are administered to a subject in need thereof.

In one embodiment, the immunogenic composition comprises natural or artificial APCs that have been manipulated in vitro to display the antigens of the present invention. DCs are potent antigen-presenting cells that initiate T cell immunity and can be used as vaccines when loaded with one or more peptides of interest, for example, by direct peptide injection. The dendritic cells may be isolated from peripheral blood by means of leukapheresis. They may be cultured in vitro with the cytokines GM-CSF and interleukin-4, loaded with antigen, and matured ex vivo to enhance antigen presentation and costimulation of T-cells before being injected into patients. Antigen may be delivered to DCs as peptide, protein, or RNA. B cells may also serve as efficient APCs for the expansion of antigen specific CD4+ T cells. B cells can present MHC Class II epitopes when pulsed exogenously and can also promote MHC Class I cross-presentation. Antigenic epitopes may also be presented by acellular artificial APCs that consist of microbeads, liposomes or exosomes.

It is contemplated within the scope of the invention that antigen loaded DCs may be prepared using the synthetic TLR 3 agonist Polyinosinic-Polycytidylic Acid-poly-L-lysine Carboxymethylcellulose (Poly-ICLC) to stimulate the DCs. Poly-ICLC is a potent individual maturation stimulus for human DCs as assessed by an upregulation of CD83 and CD86, induction of interleukin-12 (IL-12), tumor necrosis factor (TNF), interferon gamma-induced protein 10 (IP-10), interleukin 1 (IL-1), and type I interferons (IFN), and minimal interleukin 10 (IL-10) production. DCs may be differentiated from frozen peripheral blood mononuclear cells (PBMCs) obtained by leukapheresis, while PBMCs may be isolated by Ficoll gradient centrifugation and frozen in aliquots.

Illustratively, the following 7 day activation protocol may be used. Day 1-PBMCs are thawed and plated onto tissue culture flasks to select for monocytes which adhere to the plastic surface after 1-2 hr incubation at 37° C. in the tissue culture incubator. After incubation, the lymphocytes are washed off and the adherent monocytes are cultured for 5 days in the presence of interleukin-4 (IL-4) and granulocyte macrophage-colony stimulating factor (GM-CSF) to differentiate to immature DCs. On Day 6, immature DCs are pulsed with the keyhole limpet hemocyanin (KLH) protein which serves as a control for the quality of the vaccine and may boost the immunogenicity of the vaccine. The DCs are stimulated to mature, loaded with peptide antigens, and incubated overnight. On Day 7, the cells are washed, and frozen in 1 ml aliquots containing $4$-$20 \times 10^6$ cells using a controlled-rate freezer. Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

Thus, in one embodiment of the present invention the vaccine or immunogenic composition containing at least one antigen presenting cell is pulsed or loaded with one or more peptides of the present invention. Alternatively, peripheral blood mononuclear cells (PBMCs) isolated from a patient may be loaded with peptides ex vivo and injected back into the patient. As an alternative the antigen presenting cell comprises an expression construct encoding a peptide of the present invention. The polynucleotide may be any suitable polynucleotide and it is preferred that it is capable of transducing the dendritic cell, thus resulting in the presentation of a peptide and induction of immunity.

In another embodiment, the immunogenic composition comprises recombinant antigens coupled to monoclonal antibodies directed against DC surface receptors.

Amounts effective for an immunogenic composition can depend on, e.g., the peptide composition, the manner of administration, the stage and severity of the disease being treated, the weight and general state of health of the patient, and the judgment of the prescribing physician, but generally range for the initial immunization (that is for therapeutic or prophylactic administration) from about 1.0 μg to about 50,000 μg of peptide for a 70 kg patient, followed by boosting dosages or from about 1.0 μg to about 10,000 μg of peptide pursuant to a boosting regimen over weeks to months depending upon the patient's response and condition.

The pharmaceutical compositions (e.g., vaccine compositions) for therapeutic treatment are intended for parenteral, topical, nasal, oral or local administration. Preferably, the pharmaceutical compositions are administered parenterally, e.g., intravenously, subcutaneously, intradermally, or intramuscularly. The compositions may be administered at the site of surgical excision to induce a local immune response to the tumor. The invention provides compositions for parenteral administration which comprise a solution of the peptides and vaccine or immunogenic compositions are dissolved or suspended in an acceptable carrier, preferably an aqueous carrier. A variety of aqueous carriers may be used, e.g., water, buffered water, 0.9% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

A liposome suspension containing a peptide may be administered intravenously, locally, topically, etc. in a dose which varies according to, inter alia, the manner of administration, the peptide being delivered, and the stage of the disease being treated. For targeting to the immune cells, a ligand, such as, e.g., antibodies or fragments thereof specific for cell surface determinants of the desired immune system cells, can be incorporated into the liposome.

For solid compositions, conventional or nanoparticle nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more peptides of the invention, and more preferably at a concentration of 25%-75%.

For aerosol administration, the immunogenic peptides are preferably supplied in finely divided form along with a surfactant and propellant. Typical percentages of peptides are 0.01%-20% by weight, preferably 1%-10%. The surfactant can, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, cholesteric and oleic acids with an aliphatic polyhydric alcohol or its cyclic anhydride. Mixed esters, such as mixed or natural glycerides may be employed. The surfactant may constitute 0.1%-20% by weight of the composition, preferably 0.25-5%. The balance of the composition is ordinarily propellant. A carrier can also be included as desired, as with, e.g., lecithin for intranasal delivery.

As described in further detail herein, in vitro production of antigenic peptides may occur by a variety of methods known to one of skill in the art such as, for example, peptide synthesis or expression of a peptide/polypeptide from a DNA or RNA molecule in any of a variety of bacterial, eukaryotic, or viral recombinant expression systems, followed by purification of the expressed peptide/polypeptide. Alternatively, antigenic peptides may be produced in vivo by introducing molecules (e.g., DNA, RNA, viral expression systems, and the like) that encode antigenic peptides into a subject, whereupon the encoded antigenic peptides are expressed.

Peptides can be readily synthesized chemically utilizing reagents that are free of contaminating bacterial or animal substances (Merrifield R B: Solid phase peptide synthesis. I. The synthesis of a tetrapeptide. J. Am. Chem. Soc. 85:2149-54, 1963). In certain embodiments, antigenic peptides are prepared by (1) parallel solid-phase synthesis on multichannel instruments using uniform synthesis and cleavage conditions; (2) purification over a RP-HPLC column with column stripping; and re-washing, but not replacement, between peptides; followed by (3) analysis with a limited set of the most informative assays. Synthetic peptides provide a particularly useful means to prepare multiple immunogens efficiently and to rapidly translate identification of mutant epitopes to an effective vaccine or immunogenic composition. Peptides can be readily synthesized chemically and easily purified utilizing reagents free of contaminating bacteria or animal substances. The small size allows a clear focus on the mutated region of the protein and also reduces irrelevant antigenic competition from other components (unmutated protein or viral vector antigens).

In one embodiment, the drug formulation is a multi-epitope vaccine or immunogenic composition of long peptides. Such "long" peptides undergo efficient internalization, processing and cross-presentation in professional antigen-presenting cells such as dendritic cells, and have been shown to induce CTLs in humans (Melief and van der Burg, Immunotherapy of established (pre) malignant disease by synthetic long peptide vaccines Nature Rev Cancer 8:351 (2008)). In one embodiment, at least 1 peptide is prepared for immunization. In a preferred embodiment 20 or more peptides are prepared for immunization. In one embodiment, the neoantigenic peptide ranges from about 5 to about 50 amino acids in length. In another embodiment peptides from about 15 to about 35 amino acids in length is synthesized. In preferred embodiments, the peptide ranges from about 20 to about 35 amino acids in length.

The vaccine or immunogenic composition can further comprise an adjuvant and/or a carrier. Examples of useful adjuvants and carriers are given herein. The peptides and/or polypeptides in the composition can be associated with a carrier such as, e.g., a protein or an antigen-presenting cell such as e.g. a dendritic cell (DC) capable of presenting the peptide to a T-cell.

Vaccine or Immunogenic Composition Adjuvant

Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Effective vaccine or immunogenic compositions advantageously include a strong adjuvant to initiate an immune response. As described herein, poly-ICLC, an agonist of TLR3 and the RNA helicase-domains of MDA5 and RIG3, has shown several desirable properties for a vaccine or immunogenic composition adjuvant. These properties include the induction of local and systemic activation of immune cells in vivo, production of stimulatory chemokines and cytokines, and stimulation of antigen-presentation by DCs. Furthermore, poly-ICLC can induce durable CD4+ and CD8+ responses in humans. Importantly, striking similarities in the up regulation of transcriptional and signal transduction pathways were seen in subjects vaccinated with poly-ICLC and in volunteers who had received the highly effective, replication-competent yellow fever vaccine. Furthermore, >90% of ovarian carcinoma patients immunized with poly-ICLC in combination with a NY-ESO-1 peptide vaccine (in addition to Montanide) showed induction of CD4+ and CD8+ T cell, as well as antibody responses to the peptide in a recent phase 1 study. At the same time, poly-ICLC has been extensively tested in more than 25 clinical trials to date and exhibited a relatively benign toxicity profile. In addition to a powerful and specific immunogen the neoantigen peptides may be combined with an adjuvant (e.g., poly-ICLC) or another anti-neoplastic agent. Without being bound by theory, these neoantigens are expected to bypass central thymic tolerance (thus allowing stronger antitumor T cell response), while reducing the potential for autoimmunity (e.g., by avoiding targeting of normal self-antigens). An effective immune response advantageously includes a strong adjuvant to activate the immune system (Speiser and Romero, Molecularly defined vaccines for cancer immunotherapy, and protective T cell immunity Seminars in Immunol 22:144 (2010)). For example, Toll-like receptors (TLRs) have emerged as powerful sensors of microbial and viral pathogen "danger signals", effectively inducing the innate immune system, and in turn, the adaptive immune system (Bhardwaj and Gnjatic, TLR AGONISTS: Are They Good Adjuvants? Cancer J. 16:382-391 (2010)). Among the TLR agonists, poly-ICLC (a synthetic double-stranded RNA mimic) is one of the most potent activators of myeloid-derived dendritic cells. In a human volunteer study, poly-ICLC has been shown to be safe and to induce a gene expression profile in peripheral blood cells comparable to that induced by one of the most potent live attenuated viral vaccines, the yellow fever vaccine YF-17D (Caskey et al, Synthetic double-stranded RNA induces innate immune responses similar to a live viral vaccine in humans J Exp Med 208:2357 (2011)). In a preferred embodiment Hiltonol®, a GMP preparation of poly-ICLC prepared by Oncovir, Inc, is utilized as the adjuvant. In other embodiments, other adjuvants described herein are envisioned. For instance oil-in-water, water-in-oil or multiphasic W/O/W; see, e.g., U.S. Pat. No. 7,608,279 and Aucouturier et al, Vaccine 19 (2001), 2666-2672, and documents cited therein.

Adjuvants are any substance whose admixture into the vaccine or immunogenic composition increases or otherwise modifies the immune response to the mutant peptide. Carriers are scaffold structures, for example a polypeptide or a polysaccharide, to which the neoantigenic peptides, is capable of being associated. Optionally, adjuvants are conjugated covalently or non-covalently to the peptides or polypeptides of the invention.

The ability of an adjuvant to increase the immune response to an antigen is typically manifested by a significant increase in immune-mediated reaction, or reduction in disease symptoms. For example, an increase in humoral immunity is typically manifested by a significant increase in the titer of antibodies raised to the antigen, and an increase in T-cell activity is typically manifested in increased cell proliferation, or cellular cytotoxicity, or cytokine secretion. An adjuvant may also alter an immune response, for example, by changing a primarily humoral or Th2 response into a primarily cellular, or Th1 response.

Suitable adjuvants include, but are not limited to 1018 ISS, aluminum salts, Amplivax, AS15, BCG, CP-870,893, CpG7909, CyaA, dSLIM, GM-CSF, IC30, IC31, Imiquimod, ImuFact IMP321, IS Patch, ISS, ISCOMATRIX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL. vector system, PLG microparticles, resiquimod, SRL172, Virosomes and other Virus-like particles, YF-17D, VEGF trap, R848, beta-glucan, Pam3Cys, Aquila's QS21 stimulon (Aquila Biotech, Worcester, Mass., USA) which is derived from saponin, mycobacterial extracts and synthetic bacterial cell wall mimics, and other proprietary adjuvants such as Ribi's Detox, Quil or Superfos. Several immunological adjuvants (e.g., MF59) specific for dendritic cells and their preparation have been described previously (Dupuis M, et al., Cell Immunol. 1998; 186 (1): 18-27; Allison A C; Dev Biol Stand. 1998; 92:3-11). Also cytokines may be used. Several cytokines have been directly linked to influencing dendritic cell migration to lymphoid tissues (e.g., TNF-alpha), accelerating the maturation of dendritic cells into efficient antigen-presenting cells for T-lymphocytes (e.g., GM-CSF, IL-1 and IL-4) (U.S. Pat. No. 5,849,589, specifically incorporated herein by reference in its entirety) and acting as immunoadjuvants (e.g., IL-12) (Gabrilovich D I, et al., J Immunother Emphasis Tumor Immunol. 1996 (6):414-418).

Toll like receptors (TLRs) may also be used as adjuvants, and are important members of the family of pattern recognition receptors (PRRs) which recognize conserved motifs shared by many micro-organisms, termed "pathogen-associated molecular patterns" (PAMPS). Recognition of these "danger signals" activates multiple elements of the innate and adaptive immune system. TLRs are expressed by cells of the innate and adaptive immune systems such as dendritic cells (DCs), macrophages, T and B cells, mast cells, and granulocytes and are localized in different cellular compartments, such as the plasma membrane, lysosomes, endosomes, and endolysosomes. Different TLRs recognize distinct PAMPS. For example, TLR4 is activated by LPS contained in bacterial cell walls, TLR9 is activated by unmethylated bacterial or viral CpG DNA, and TLR3 is activated by double stranded RNA. TLR ligand binding leads to the activation of one or more intracellular signaling pathways, ultimately resulting in the production of many key molecules associated with inflammation and immunity (particularly the transcription factor NF-κB and the Type-I interferons). TLR mediated DC activation leads to enhanced DC activation, phagocytosis, upregulation of activation and costimulation markers such as CD80, CD83, and CD86, expression of CCR7 allowing migration of DC to draining lymph nodes and facilitating antigen presentation to T cells, as well as increased secretion of cytokines such as type I interferons, IL-12, and IL-6. All of these downstream events are critical for the induction of an adaptive immune response.

Among the most promising cancer vaccine or immunogenic composition adjuvants currently in clinical development are the TLR9 agonist CpG and the synthetic double-stranded RNA (dsRNA) TLR3 ligand poly-ICLC. In preclinical studies poly-ICLC appears to be the most potent TLR adjuvant when compared to LPS and CpG due to its induction of pro-inflammatory cytokines and lack of stimulation of IL-10, as well as maintenance of high levels of co-stimulatory molecules in DCs1. Furthermore, poly-ICLC was recently directly compared to CpG in non-human primates (rhesus macaques) as adjuvant for a protein vaccine or immunogenic composition consisting of human papillomavirus (HPV) 16 capsomeres (Stahl-Hennig C, Eisenblatter M, Jasny E, et al. Synthetic double-stranded RNAs are adjuvants for the induction of T helper 1 and humoral immune responses to human papillomavirus in rhesus macaques. PLOS pathogens. April 2009; 5 (4)).

CpG immuno stimulatory oligonucleotides have also been reported to enhance the effects of adjuvants in a vaccine or immunogenic composition setting. Without being bound by theory, CpG oligonucleotides act by activating the innate (non-adaptive) immune system via Toll-like receptors (TLR), mainly TLR9. CpG triggered TLR9 activation enhances antigen-specific humoral and cellular responses to a wide variety of antigens, including peptide or protein antigens, live or killed viruses, dendritic cell vaccines, autologous cellular vaccines and polysaccharide conjugates in both prophylactic and therapeutic vaccines. More importantly, it enhances dendritic cell maturation and differentiation, resulting in enhanced activation of Th1 cells and strong cytotoxic T-lymphocyte (CTL) generation, even in the absence of CD4 T-cell help. The Th1 bias induced by TLR9 stimulation is maintained even in the presence of vaccine adjuvants such as alum or incomplete Freund's adjuvant (IFA) that normally promote a Th2 bias. CpG oligonucleotides show even greater adjuvant activity when formulated or co-administered with other adjuvants or in formulations such as microparticles, nano particles, lipid emulsions or similar formulations, which are especially necessary for inducing a strong response when the antigen is relatively weak. They also accelerate the immune response and enabled the antigen doses to be reduced by approximately two orders of magnitude, with comparable antibody responses to the full-dose vaccine without CpG in some experiments (Arthur M. Krieg, Nature Reviews, Drug Discovery, 5, June 2006, 471-484). U.S. Pat. No. 6,406,705 B1 describes the combined use of CpG oligonucleotides, non-nucleic acid adjuvants and an antigen to induce an antigen-specific immune response. A commercially available CpG TLR9 antagonist is dSLIM (double Stem Loop Immunomodulator) by Mologen (Berlin, GERMANY), which is a preferred component of the pharmaceutical composition of the present invention. Other TLR binding molecules such as RNA binding TLR 7, TLR 8 and/or TLR 9 may also be used.

Other examples of useful adjuvants include, but are not limited to, chemically modified CpGs (e.g. CpR, Idera), Poly(I:C) (e.g. polyi:CI2U), non-CpG bacterial DNA or RNA as well as immunoactive small molecules and antibodies such as cyclophosphamide, sunitinib, bevacizumab, celebrex, NCX-4016, sildenafil, tadalafil, vardenafil, sorafenib, XL-999, CP-547632, pazopanib, ZD2171, AZD2171, ipilimumab, tremelimumab, and SC58175, which may act therapeutically and/or as an adjuvant. The amounts and concentrations of adjuvants and additives useful in the context of the present invention can readily be determined by the skilled artisan without undue experimentation. Additional adjuvants include colony-stimulating factors, such as Granulocyte Macrophage Colony Stimulating Factor (GM-CSF, sargramostim).

Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and production of a "natural mix" of type I interferons, cytokines, and chemokines. Furthermore, poly-ICLC exerts a more direct, broad host-targeted anti-infectious and possibly antitumor effect mediated by the two IFN-inducible nuclear enzyme systems, the 2'5'-OAS and the P1/eIF2a kinase, also known as the PKR (4-6), as well as RIG-I helicase and MDA5.

In rodents and non-human primates, poly-ICLC was shown to enhance T cell responses to viral antigens, cross-priming, and the induction of tumor-, virus-, and autoantigen-specific CD8+ T-cells. In a recent study in non-human primates, poly-ICLC was found to be essential for the generation of antibody responses and T-cell immunity to DC targeted or non-targeted HIV Gag p24 protein, emphasizing its effectiveness as a vaccine adjuvant.

In human subjects, transcriptional analysis of serial whole blood samples revealed similar gene expression profiles among the 8 healthy human volunteers receiving one single s.c. administration of poly-ICLC and differential expression of up to 212 genes between these 8 subjects versus 4 subjects receiving placebo. Remarkably, comparison of the poly-ICLC gene expression data to previous data from volunteers immunized with the highly effective yellow fever vaccine YF17D showed that a large number of transcriptional and signal transduction canonical pathways, including those of the innate immune system, were similarly upregulated at peak time points.

More recently, an immunologic analysis was reported on patients with ovarian, fallopian tube, and primary peritoneal cancer in second or third complete clinical remission who were treated on a phase 1 study of subcutaneous vaccination with synthetic overlapping long peptides (OLP) from the cancer testis antigen NY-ESO-1 alone or with Montanide-ISA-51, or with 1.4 mg poly-ICLC and Montanide. The generation of NY-ESO-1-specific CD4+ and CD8+ T-cell and antibody responses were markedly enhanced with the addition of poly-ICLC and Montanide compared to OLP alone or OLP and Montanide.

Lot release testing for the batches of DCs may be performed to meet minimum specifications before the DCs are injected into patients (see e.g., Sabado et al. (2013) Preparation of tumor antigen-loaded mature dendritic cells for immunotherapy, J. Vis Exp. August 1; (78). doi: 10.3791/50085).

Indications

In one embodiment, the subject is suffering from a neoplasia selected from the group consisting of: Non-Hodgkin's Lymphoma (NHL), clear cell Renal Cell Carcinoma (ccRCC), melanoma, sarcoma, leukemia or a cancer of the bladder, colon, brain, breast, head and neck, endometrium, lung, ovary, pancreas and prostate.

In one embodiment, the subject is suffering from an autoimmune disease selected from the group consisting of: celiac disease, diabetes mellitus type 1, Graves' disease, inflammatory bowel disease, multiple sclerosis, psoriasis, rheumatoid arthritis, and systemic lupus erythematosus.

In one embodiment, the subject is suffering from a bacterial disease or is at risk of contracting a bacterial disease selected from the group consisting of the genus's: *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia.*

In one embodiment, the subject is suffering from a viral disease or is at risk of contracting a viral disease selected from the group consisting of the families: Adenoviridae, Picornaviridae, Herpesviridae, Hepadnaviridae, Flaviviridae, Retroviridae, Orthomyxoviridae, Paramyxoviridae, Papovaviridae, Polyomavirus, Rhabdoviridae, and Togaviridae.

In one embodiment, the subject is suffering from a protozoan disease or is at risk of contracting a protozoan disease, such as, but not limited to malaria.

Epitope Prediction Coupled with TCR Profiling

In certain example embodiments, the epitope identification methods disclosed herein may be coupled with TCR profiling to derive antigen-specific therapeutics tailored to the immunodominance of a particular epitope. For example, the methods disclosed herein may be used to derive protective vaccines as well as tolerizing vaccines that induce or more limited immune response than a protective vaccine. A sample to be analyzed is obtained. The sample may originate from a patient to be treated or may be representative of a condition to be treated. The sample may be derived from a biological sample or a biopsy sample depending on the nature of the disease to be addressed. The sample may be an infectious disease sample, a cancer tumor sample, or may be derived from inflamed tissues associated with inflammatory disease, autoimmunity, or allergies. A portion of the sample may be used to derive an input genomic sequence for epitope identification in accordance with the methods described above. In addition, the sample may be used for tissue profiling analysis, such as tissue transcriptome, metatranscriptome, or tumor transcriptome analysis to identify the cell types and/or cell states present in the sample.

Transcriptome analysis may be carried out using known methods in the art. For example, the transcriptome analysis may involve high-throughput single-cell RNA-seq and/or targeted nucleic acid profiling (for example, sequencing, quantitative reverse transcription polymerase chain reaction, and the like).

In certain embodiments, the invention involves single cell RNA sequencing (see, e.g., Kalisky, T., Blainey, P. & Quake, S. R. Genomic Analysis at the Single-Cell Level. Annual review of genetics 45, 431-445, (2011); Kalisky, T. & Quake, S. R. Single-cell genomics. Nature Methods 8, 311-314 (2011); Islam, S. et al. Characterization of the single-cell transcriptional landscape by highly multiplex RNA-seq. Genome Research, (2011); Tang, F. et al. RNA-Seq analysis to capture the transcriptome landscape of a single cell. Nature Protocols 5, 516-535, (2010); Tang, F. et al. mRNA-Seq whole-transcriptome analysis of a single cell. Nature Methods 6, 377-382, (2009); Ramskold, D. et al. Full-length mRNA-Seq from single-cell levels of RNA and individual circulating tumor cells. Nature Biotechnology 30, 777-782, (2012); and Hashimshony, T., Wagner, F., Sher, N. & Yanai, I. CEL-Seq:Single-Cell RNA-Seq by Multiplexed Linear Amplification. Cell Reports, Volume 2, Issue 3, p 666-673, 2012).

In certain embodiments, the invention involves plate based single cell RNA sequencing (see, e.g., Picelli, S. et al., 2014, "Full-length RNA-seq from single cells using Smart-seq2" Nature protocols 9, 171-181, doi: 10.1038/nprot.2014.006).

In certain embodiments, the invention involves high-throughput single-cell RNA-seq and/or targeted nucleic acid profiling (for example, sequencing, quantitative reverse transcription polymerase chain reaction, and the like) where the RNAs from different cells are tagged individually, allowing a single library to be created while retaining the cell identity of each read. In this regard reference is made to Macosko et al., 2015, "Highly Parallel Genome-wide Expression Profiling of Individual Cells Using Nanoliter Droplets" Cell 161, 1202-1214; International patent application number PCT/US2015/049178, published as WO2016/040476 on Mar. 17, 2016; Klein et al., 2015, "Droplet Barcoding for Single-Cell Transcriptomics Applied to Embryonic Stem Cells" Cell 161, 1187-1201; International patent application number PCT/US2016/027734, published as WO2016168584A1 on Oct. 20, 2016; Zheng, et al., 2016, "Haplotyping germline and cancer genomes with high-throughput linked-read sequencing" Nature Biotechnology 34, 303-311; Zheng, et al., 2017, "Massively parallel digital transcriptional profiling of single cells" Nat. Commun. 8, 14049 doi: 10.1038/ncomms14049; International patent publication number WO2014210353A2; Zilionis, et al., 2017, "Single-cell barcoding and sequencing using droplet microfluidics" Nat Protoc. January; 12(1):44-73; Cao et al., 2017, "Comprehensive single cell transcriptional profiling of a multicellular organism by combinatorial indexing" bioRxiv preprint first posted online Feb. 2, 2017, doi: dx.doi.org/10.1101/104844; Rosenberg et al., 2017, "Scaling single cell transcriptomics through split pool barcoding" bioRxiv preprint first posted online Feb. 2, 2017, doi: dx.doi.org/10.1101/105163; Vitak, et al., "Sequencing thousands of single-cell genomes with combinatorial indexing" Nature Methods, 14(3):302-308, 2017; Cao, et al., Comprehensive single-cell transcriptional profiling of a multicellular organism. Science, 357(6352):661-667, 2017; and Gierahn et al., "Seq-Well: portable, low-cost RNA sequencing of single cells at high throughput" Nature Methods 14, 395-398 (2017), all the contents and disclosure of each of which are herein incorporated by reference in their entirety.

In certain embodiments, the invention involves single nucleus RNA sequencing. In this regard reference is made to Swiech et al., 2014, "In vivo interrogation of gene function in the mammalian brain using CRISPR-Cas9" Nature Biotechnology Vol. 33, pp. 102-106; Habib et al., 2016, "Div-Seq: Single-nucleus RNA-Seq reveals dynamics of rare adult newborn neurons" Science, Vol. 353, Issue 6302, pp. 925-928; Habib et al., 2017, "Massively parallel single-nucleus RNA-seq with DroNc-seq" Nat Methods. 2017 October; 14(10):955-958; and International patent application number PCT/US2016/059239, published as WO2017164936 on Sep. 28, 2017, which are herein incorporated by reference in their entirety.

Any method of HLA typing known in the art may be used for the present invention (see, e.g., Erlich, HLA typing using next generation sequencing: An overview, Human Immunology 76 (2015) 887-890).

A second portion from the same sample may be used for T-cell profiling. In certain embodiments, the invention involves identifying T cell receptors (TCR) specific for activation by an immunodominant epitope of the present invention. Identifying, cloning and expressing TCRs according to the present invention may be performed according to any methods known in the art. CD4+ T cells may be isolated by sorting for CD4+ cells. Regarding TCR sequencing, single cell TCR sequencing and expression of TCRs on an immune cell, reference is made to International patent application, "Methods of isolating T cell receptors," serial number PCT/US2015/067154 and published as WO2016100977A1; Rosati et al., Overview of methodologies for T-cell receptor repertoire analysis BMC Biotechnol. 2017, 17:61; and Calis and Rosenberg, Characterizing immune repertoires by high throughput sequencing: strategies and applications Trends Immunol. 35(12): 581-590, incorporated herein in its entirety. T cells may be profiled, for example using single cell RNA-seq to differentiate between T cells of a pathogenic and protective phenotype. The sample may be further analyzed using single cell TCR-seq to identify pathogenic TCRs and protective TCRs. Single cell RNA-seq targeted for TCRs (TCRseq) is described further in materials and methods.

Epitopes identified using the methods disclosed herein may be cloned into a first peptide library, such as a lentiviral peptide MHCII$\zeta\zeta$ library using known methods in the art. Likewise, the identified TCRs may be cloned into a second library, such as a lentiviral TCR$\zeta\zeta$ library. The first and second libraries may then be transfected into appropriate cell types to allow expression of the peptide-MHCII and TCR complexes on localization on the cell membrane respectively. For example, the peptide-MHCII library may be clone into a BW5147 cell line, and the TCR library may be cloned into a BW5147-CD4.2 cell line. One cell line may further be modified to include a reporter system that generates a detectable signal upon binding of the TCR and peptide-MHC complexes. For example, the cell line comprising the MHCII library may further include a reporter construct. In certain example embodiments, the reporter construct may comprise a GFP under control of an inducible promoter. The inducible promoter may be under the control of or responsive to a signal generated by an activated TCR or MHCII complex. For example, the reporter construct may the inducible promoter may activate expression of GFP in response to IL-2 production. While GFP is provided by way of example, other detectable signals that facilitate sorting and/or isolation of the peptide-MHCII expressing cells may also be used. The TCR expressing and peptide-MHCII expressing cells are brought into contact with one another under conditions to allow binding between complementary TCR and MHCII complexes. Activated MHCII expressing cells are then sort or otherwise isolated based on expression of the detectable signal. The MHC peptides are subsequently isolated and sequenced using known methods in the art. The number of peptide sequencing reads per peptide provides a measure of each epitopes immunodominance. The present invention may use any known method of peptide sequencing known in the art (see, e.g., U.S. Pat. No. 6,379,970).

In certain example embodiments, peptides with the requisite or desired degree of immunodominance are then isolated and further used to prepare immunogenic compositions as described above. Said peptides may also be used for Ag-specific expansion of endogenous T-cells and/or Ag-specific depletion of endogenous T cells using known methods in the art.

Probing the Host-Commensal Relationship to Reveal "Health Status" of the Immune System The human microbiota is the aggregate of microorganisms that resides on or within any of a number of human tissues and biofluids, including the skin, mammary glands, placenta, seminal fluid, uterus, ovarian follicles, lung, saliva, oral mucosa, conjunctiva, biliary and gastrointestinal tracts. They include bacteria, archaea, fungi, protists and viruses. Some microorganisms that colonize humans are commensal, meaning they co-exist without harming humans.

Figure 20:
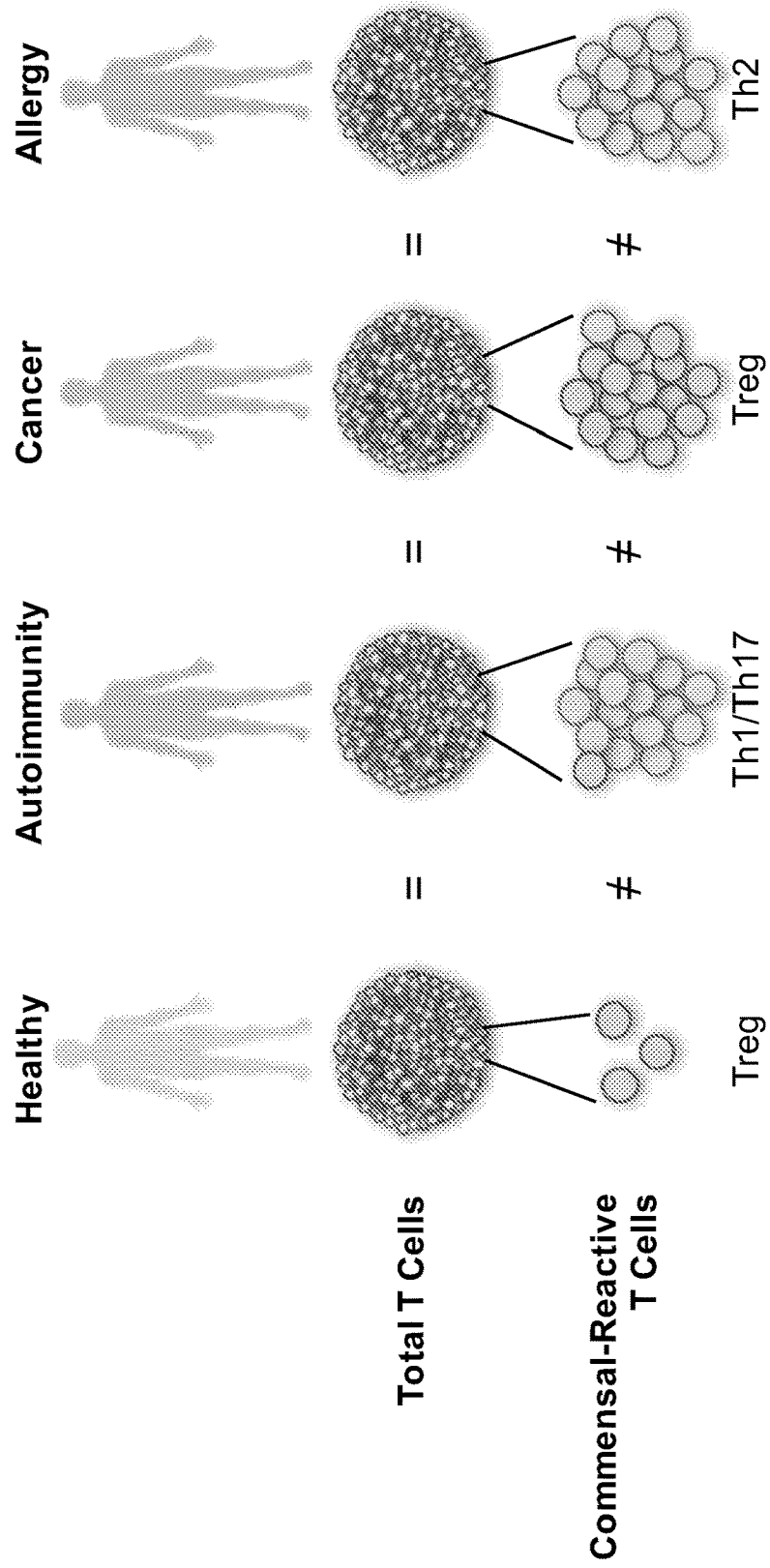
FIG. 20—Illustrates immune cell type reactivity and health status.
Figure 21:
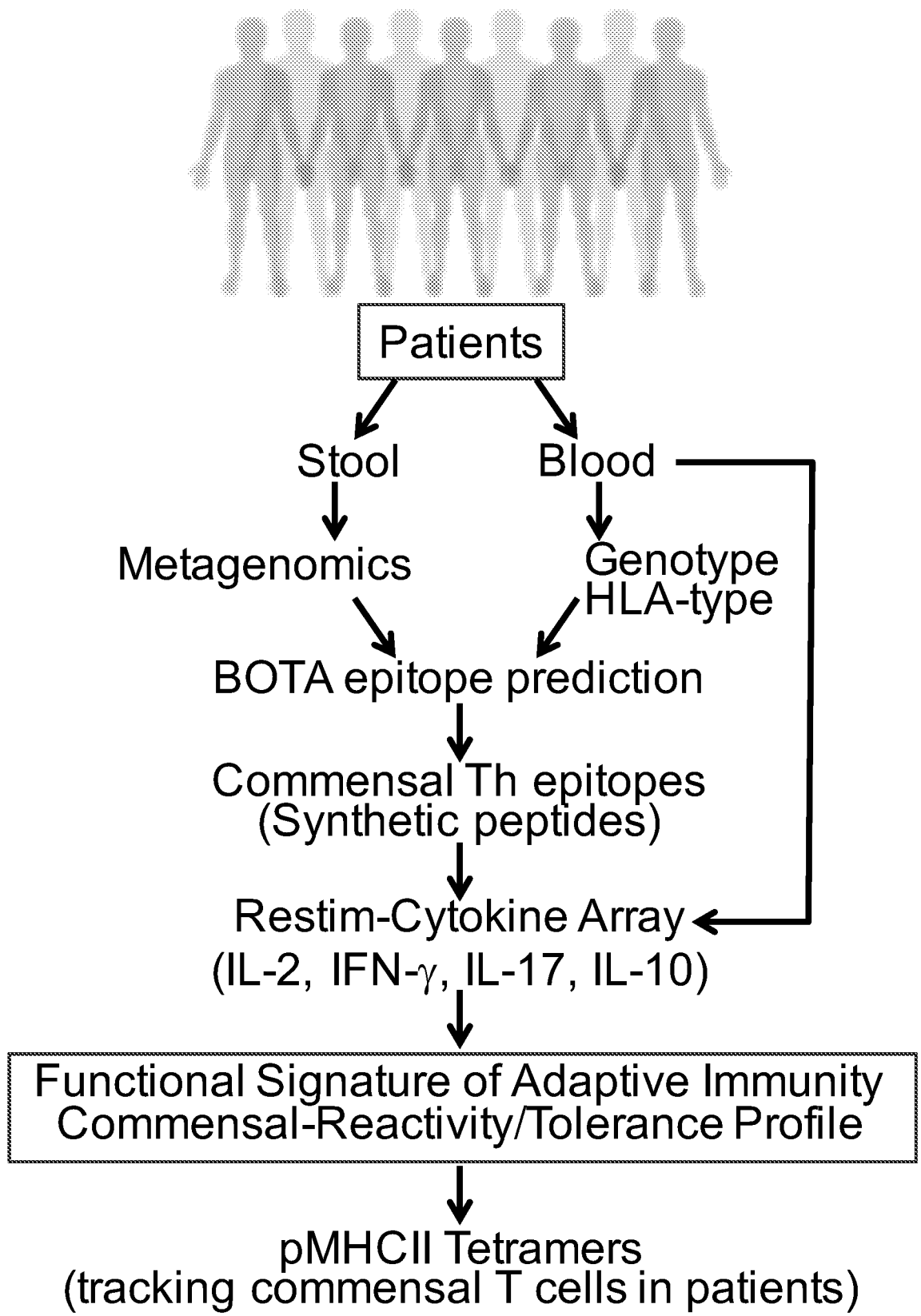
FIG. 21—Illustrates a clinical immunology pipeline for identifying HLA specific epitopes for use in measuring commensal-reactivity/tolerance profiles and for tracking commensal T cells in patients using the epitopes.

In certain embodiments, monitoring the magnitude and nature of the T cell response to specific commensal antigens can reveal the health status of the immune system. For example, having Tregs reactive to commensal epitopes may indicate health, having Th1/Th17 cells reactive to commensal epitopes may indicate autoimmunity, having Tregs reactive to tumor antigen epitopes may indicate cancer status (e.g., a suppressed immune response to the tumor), and having Th2 cells reactive to allergen epitopes may indicate allergy (see, FIG. 20). In certain embodiments, pMHCII tetramers are used to track commensal T cells in a subject (see, FIG. 21).

In the state of health, the adaptive immune system maintains tolerance to local gut antigen exposure and protection from systemic infection. The sheer number of bacterial species and diversity of protein-coding elements in the microbiome represents an enormous search space. Towards identifying immunogenic commensals, Applicants developed "serum immunoglobulin commensal capture and sequencing" (SICC-seq). In certain embodiments, commensal epitopes are predicted from sequencing data obtained from a biological sample. For example, a sample may be taken from a subject (e.g., stool) and the microbiota may be identified. Genomes of organisms in the microbiota may be identified and MHCII epitopes predicted according to the present invention (e.g., according to HLA-type of the subject). In certain embodiments, the HLA type of the subject is determined using a blood sample (e.g., serum). In certain embodiments, the epitopes are used to detect cytokine production in immune cells (e.g., T cells) obtained from the subject (e.g., IL-2, IFN-γ, IL-17, IL-10) (see, FIG. 21). Cytokine assays (e.g., cytokine arrays) are well known in the art. In certain embodiments, IL-10 secretion in response to an epitope indicates health (e.g., secretion from Tregs). In certain embodiments, secretion of IL-17 (e.g., Th17 cells) indicates autoimmunity. In certain embodiments, pMHCII tetramers are used to track commensal T cells secreting the cytokines in the subject (see, FIG. 21).

The present invention has advantageously used MHCII peptidomics to identify novel bacterial antigens. Additionally, Applicants have determined novel features of antigenicity from immunopeptidome generally applicable to the prediction of any MHCII binding peptide. Moreover, Applicants have advantageously provided a deep neural network algorithm, BOTA, that predicts immunodominant epitopes. Finally, Applicants have determined that host autophagy pathways differentially control epitope selection.

Although specific embodiments have been described above in detail, the description is merely for purposes of illustration. It should be appreciated, therefore, that many aspects described above are not intended as required or essential elements unless explicitly stated otherwise. Modifications of, and equivalent components or acts corresponding to, the disclosed aspects of the example embodiments, in addition to those described above, can be made by a person of ordinary skill in the art, having the benefit of the present disclosure, without departing from the spirit and scope of embodiments defined in the following claims, the scope of which is to be accorded the broadest interpretation so as to encompass such modifications and equivalent structures.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1—MHCII Peptidomics in Primary Murine Dendritic Cells Defines Biochemical Features of Antigenicity Defining the immunodominance hierarchy of T cell epitopes remains a significant challenge in the context of infectious disease, autoimmunity, and immune oncology. Even for some of the most widespread bacterial pathogens, little is known about which antigens drive protective CD4 T cell responses. Towards the aim of defining features of antigenicity, Applicants developed a proteomics-based approach to identify MHCII-associated peptides in murine bone marrow-derived dendritic cells (BMDCs) from C57BL/6J mice expressing I-A$^b$. In these experiments, mature peptide-MHCII complexes were immunoprecipitated from primary BMDCs with monoclonal Y3P antibody (Janeway et al., 1984). Associated peptides from biological replicates were acid-eluted, chemically labeled with iTRAQ isobaric mass tags for relative quantification, mixed, and analyzed using high resolution, accurate mass liquid chromatography-tandem mass spectrometry (LC-MS/MS) (FIG. 7A). This approach identified 3,671 unique peptides derived from 1,088 autologous murine proteins (FIG. 7B and SEQ ID NOs: 1-14979). The sensitivity afforded by Orbitrap detection methods in combination with differential mass tagging by iTRAQ enabled relative quantitation of significantly more peptides than previously reported approaches.

Having generated an expansive catalogue of the MHCII immunopeptidome in murine BMDCs, Applicants sought to identify key biochemical features of antigenicity. Initially, Applicants derived the optimal I-A$^b$-binding motif from primary sequence features in autologous murine peptides (FIG. 7C). The resulting 9mer core peptide sequence resembles previous predictions based on in vitro binding kinetics between synthetic peptide libraries and purified I-A$^b$ (Andreatta et al., 2011). In contrast, Applicants detected a strong preference for proline in the P4 position.

Example 2—Autophagy Shapes the MHCII Immunopeptidome

Figure 8A:
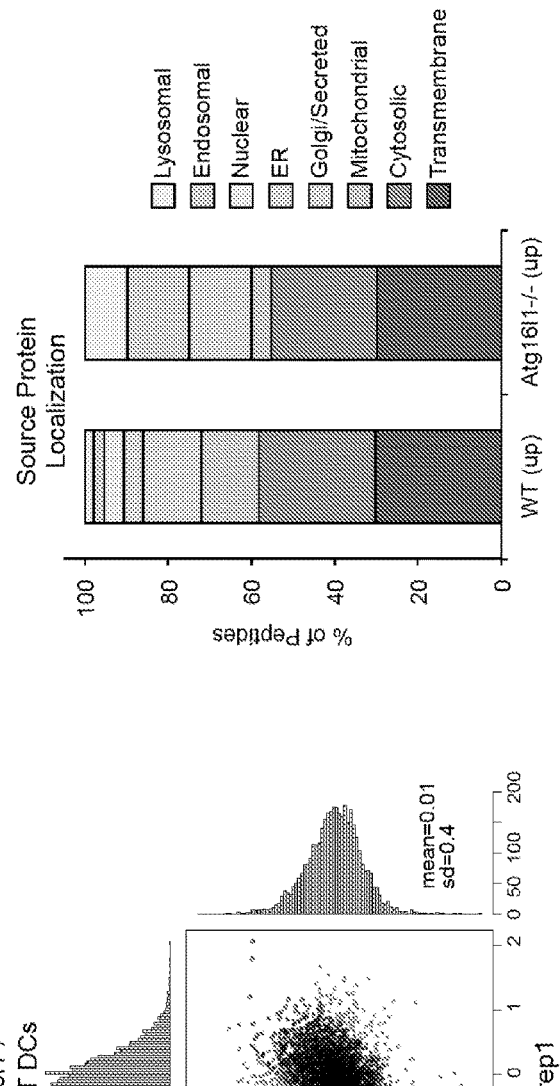
FIG. 8A shows that deficiency in the autophagy protein Atg16l1 dramatically skews the spectrum of MHCII-associated peptides. MHCII-bound peptides quantified in Atg6l1$^{-/-}$ dendritic cells relative to wild type (WT). Replicate (rep) samples were compared based on log 2 fold change (FC) between mouse strains. Each dot represents a unique peptide sequence. Peptides that were observed to be significantly upregulated or downregulated are shown, while peptide measurements that were not reproducible across both biological replicates are also shown. Dot plot axes: Log 2 FC. Histogram axes: number of distinct peptides.
Figure 8B:
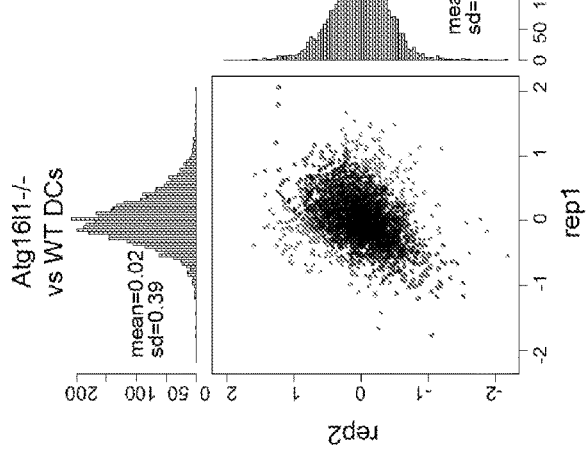
FIG. 8B shows the abundance and subcellular sources of MHCII-associated peptides derived from Atg16l1$^{-/-}$ and WT dendritic cells.
Figure 8C:
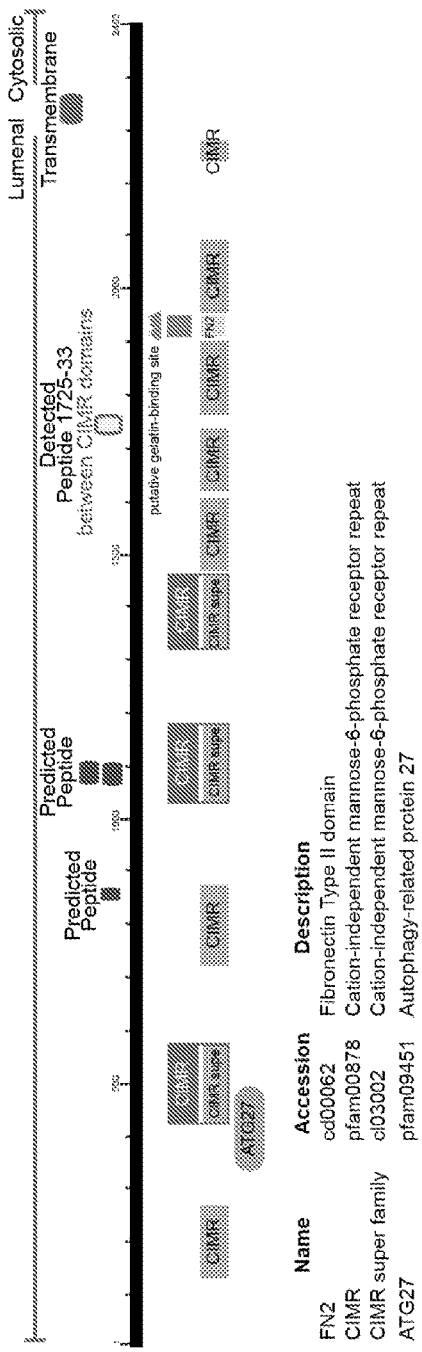
FIG. 8C shows epitope mapping relative to domain structure of endogenous antigens indicates preferential presentation of epitopes derived from the lumenal/extracellular domains of transmembrane proteins and epitopes positioned between structurally-defined domains.

The primary sequence of antigenic peptides confers binding to MHCII but does not represent the only factor governing antigenicity. The nature of how host pathways shape the immunopeptidome remains incompletely understood. Given that lysosomal pathways contribute to antigen processing and epitope selection, Applicants hypothesized that autophagy shapes the immunopeptidome by dictating which antigens gain access to the lysosomal compartment. Applicants aimed to shed light on the subject by leveraging MHCII peptidomics. The core autophagy protein ATG16L1 is required for macroautophagy and xenophagy, which divert cytosolic cargo to lysosomes for disposal. To selectively perturb autophagy in antigen-presenting cells, Applicants generated Atg16l1$^{f/f}$×CD11c-Cre mice (Atg16l1$^{-/-}$). MHCII peptidomics experiments demonstrated that Atg16l1$^{-/-}$BMDCs were severely impaired in their ability to present peptides derived from organelle-derived and cytosolic proteins (FIGS. 8A and 8B). In contrast, Atg16l1$^{-/-}$ cells displayed elevated levels of lysosome- and endosome-derived peptides compared to WT BMDCs (FIGS. 8B and 8E). These findings are consistent with the known role for Atg16l1 in macroautophagy and highlight the degree to which lysosomal trafficking impacts the spectrum of peptides presented by MHCII.

Figure 16:
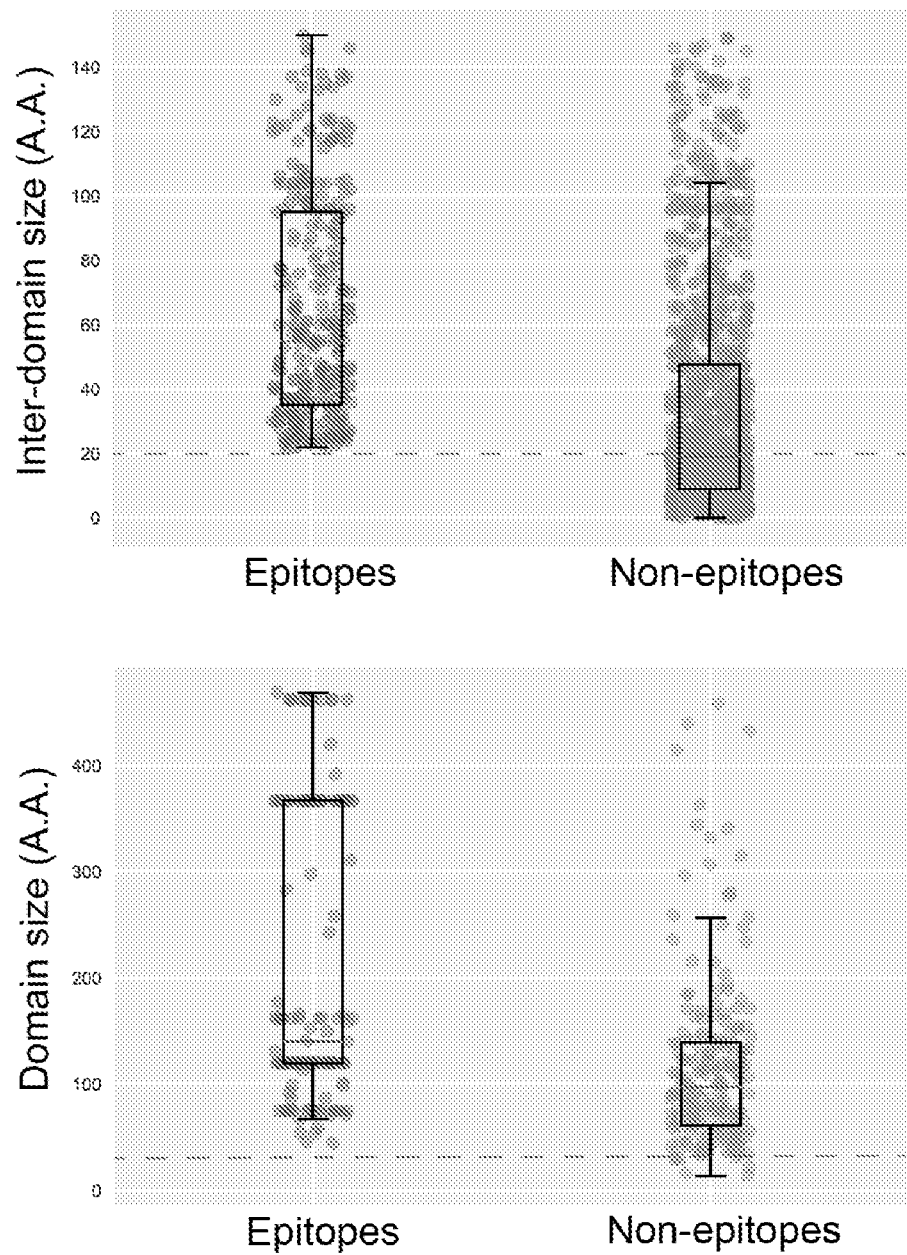
FIG. 16—Features of antigenicity. Epitopes from MHCII peptidomics experiments were mapped back to the endogenous murine proteins from which they derived. If epitopes localized between PFAM domains, inter-domain sizes were plotted (Top). For epitopes that localized within PFAM domains, the domain sizes were plotted (Bottom). The same procedure was performed for Non-epitopes, which were defined as peptides conforming to the I-A$^b$-binding consensus motif (motif score $>5 \times 10^{-11}$). Epitopes preferentially derived from inter-domain regions that are greater than 20 amino acids in length or from within domains of more than 30 amino acids. A.A.; amino acids.

Given the abundance of MHCII-associated peptides derived from endolysosomal proteins, Applicants queried these sequences to define additional features of antigenicity. Using the high-resolution I-A$^b$-binding motif as a reference sequence (FIG. 7C), Applicants scanned endolysosomal proteins identified by proteomics for consensus. As expected, Applicants were able to retrospectively predict peptides that were identified by mass spectrometry; however, Applicants found many instances of consensus sites that were not presented on MHCII. In the vast majority of these cases, consensus sites located within structured protein domains were not detected by proteomics, whereas those located in unstructured inter-domain regions were. For example, MHCII peptidomics identified one peptide derived from the murine cation-independent mannose 6-phosphate receptor (CI-MPR). This peptide is located between two CIMR domains. In contrast, Applicants found three additional peptides conforming to the I-A$^b$-binding consensus motif that were located within CIMR domains and were not detected as processed peptides bound to MHCII (FIG. 8C). Across the entire dataset, epitopes preferentially derived from interdomain regions of greater than 20 amino acids or protein domains greater than 30 amino acids (FIGS. 13 and 16). Thus, epitope accessibility in the context of native proteins is an important factor that impacts MHCII binding and protease processing.

Example 3—Training a Deep Neural Network on MHCII Peptidomics Data

Having demonstrated that MHCII peptidomics can identify antigenic features conferred by lysosomal processing, Applicants leveraged this dataset to devise a neural network-based algorithm for epitope prediction. Historically, predicting MHCII binding strength for a given peptide has been challenging. The concept of epitope accessibility, together with MHCII affinity, adds to the complexity of formulating predictions for immunodominant epitopes. Such features are not adequately captured by linear relationships; rather, a non-linear architecture is more appropriate. Therefore, Applicants explored the use of a deep neural network-based algorithm to predict these epitopes using peptidomics data as a training set.

Figure 8D:
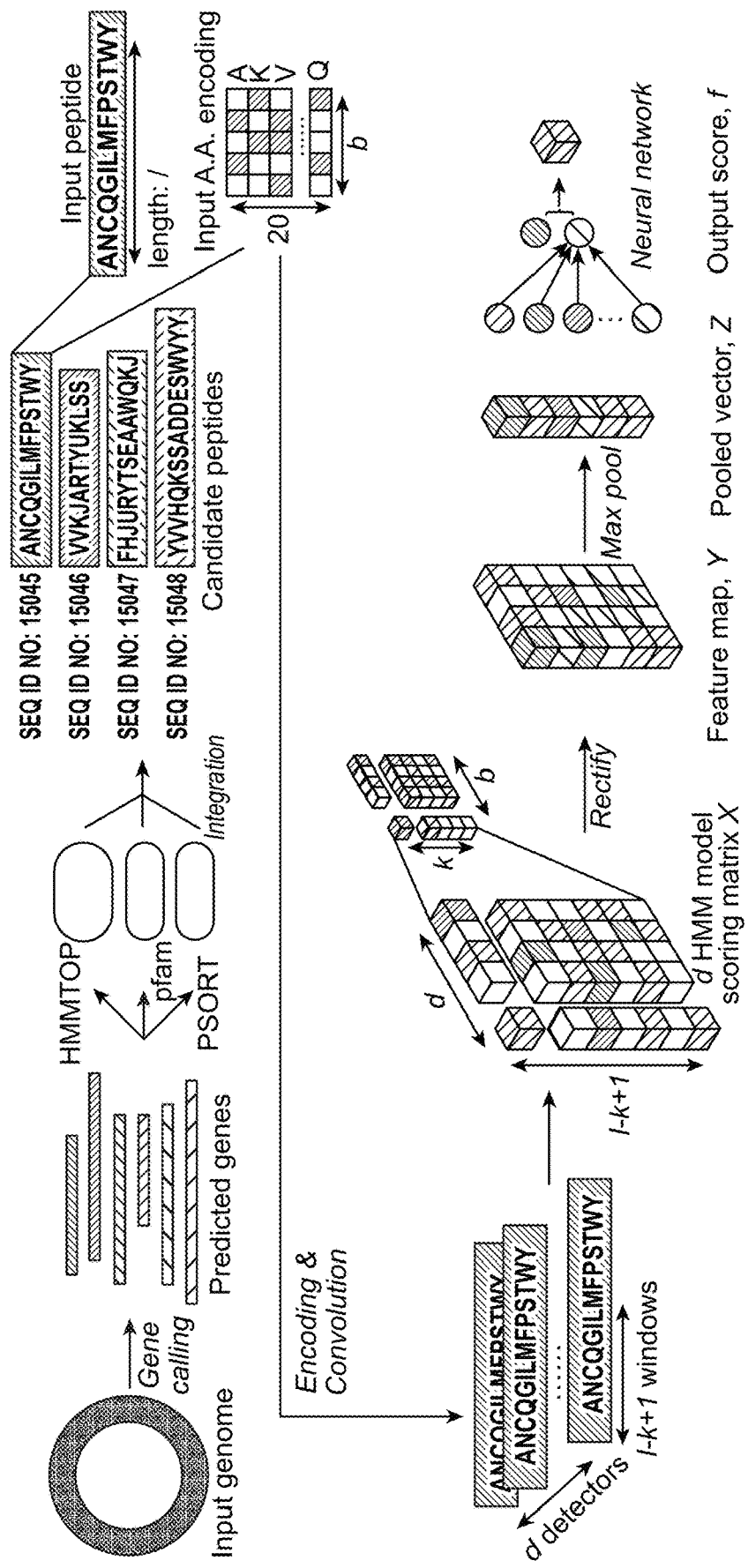
FIG. 8D shows immunodominant epitope prediction with BOTA. Workflow of BOTA with input as genome and output as a binding score. The upper panel shows the extraction of candidate peptides (SEQ ID NOs: 15045-15048), and the lower panel shows the deep neural network core of the BOTA algorithm to assign a binding score to each candidate peptide.
Figure 8E:
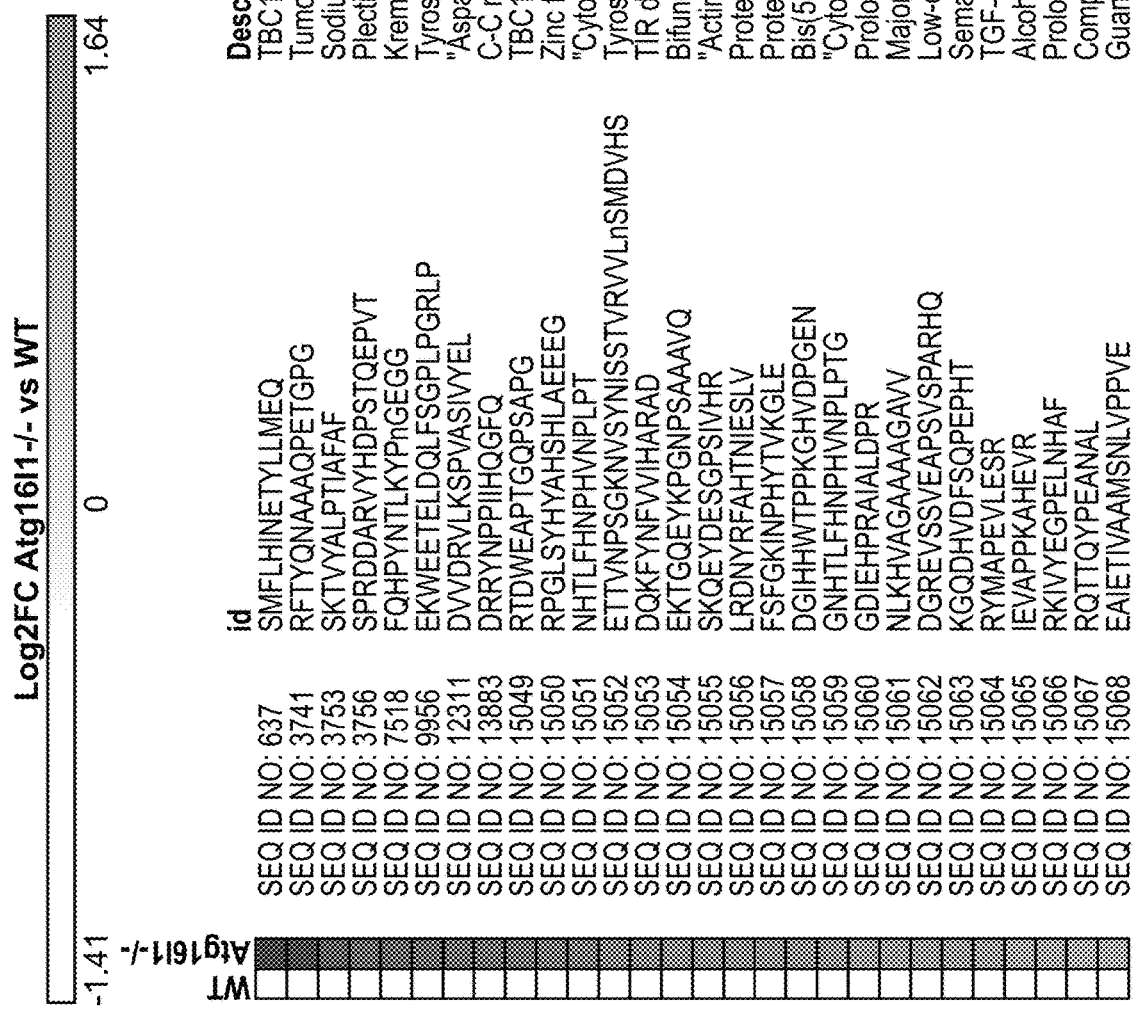
FIG. 8E shows MHCII-associated peptides derived from Atg16l1$^{-/-}$ and WT dendritic cells. Shown are SEQ ID NOs: 637, 3741, 3753, 3756, 7518, 9956, 12311, 13883, and 15049-15100, respectively.

Applicants developed a model, bacteria-origin T cell antigen (BOTA) predictor, that generates a list of candidate peptides utilizing information including protein cellular location, transmembrane structure (if applicable), and domain distribution (FIG. 8D). BOTA requires only an annotated genome input to extract amino acid sequences of protein-coding genes. BOTA then relies on outputs from three algorithms: HMMTOP, PSORT, and HMMER's search against pfam. First, BOTA identifies secreted and cell wall proteins (Yu et al., 2010). Second, it masks intracellular regions and transmembrane domains of cell wall proteins (with an 8-amino acid flanking buffer) (Tusnady and Simon, 1998). Third, it excludes regions that fall within small domains or between a series of adjacent domains (inaccessible, compact folding) (Marchler-Bauer et al., 2015). The metric used for domain mapping includes the distance to the up/downstream domains, the density of flanking domains, and the domain size. Finally, candidate protein regions are piped into the deep neural network predictor to generate their probabilities to be MHCII binders (FIG. 8D). Applicants note that this pipeline is modular and can be used to generate allele-specific models in both human and model animals.

The core algorithm of BOTA is a deep neural network, which employs a sparse representation of input peptides and multiple pre-trained binder models to generate a feature map. The feature map includes many nonlinear summarizations of peptide features that are used to make predictions. The output from the deep neural network is a score (f) that serves as an indicator of MHCII binding. In the case of mouse I-A$^b$, Applicants used proteomics data to train the BOTA model. The model was trained using randomly sampled parameters 30 times on a 3-fold cross-validation scheme. The optimal parameter calibration was selected based on their receiver operating characteristic curves (ROC AUCs).

The advantages of BOTA in comparison to current methods are that BOTA (1) requires only whole genome, not polypeptides, as input, (2) considers epitope accessibility by focusing the search on extracellular regions of proteins and epitope location relative to protein domain organization, (3) is trained on peptidomics data from antigen-presenting cells, which are significantly more accurate than in vitro peptide binding data, and (4) easily scales to thousands of genomes for different alleles. Thus, BOTA is capable of accurately predicting immunogenic epitopes from medically relevant bacterial pathogens.

Figure 9B:
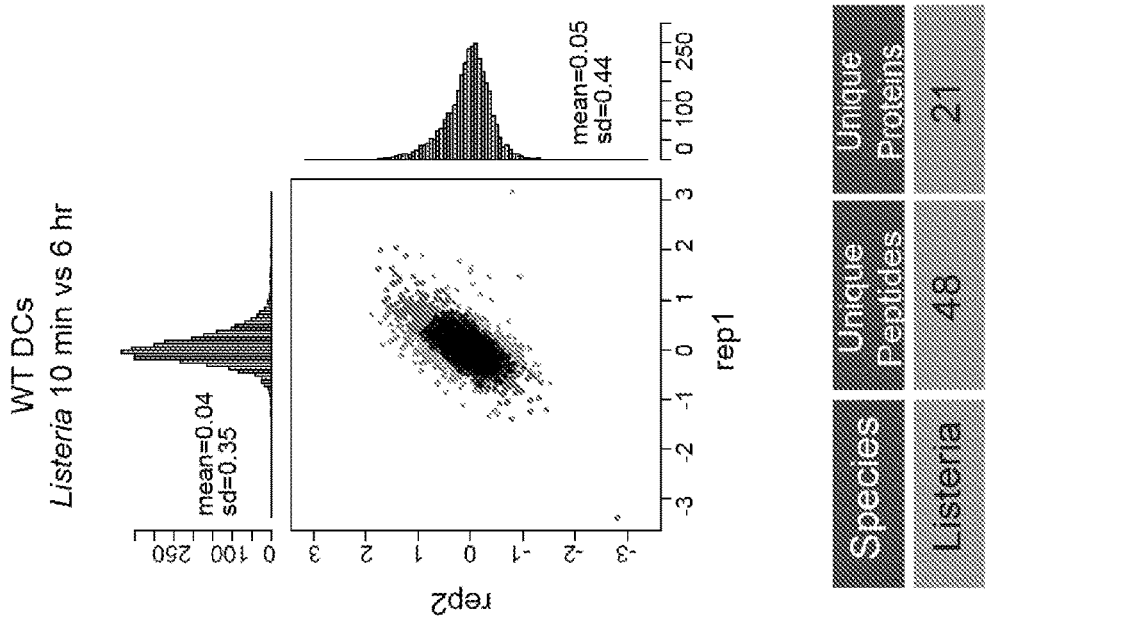
FIG. 9B shows MHCII-bound peptides detected before and after Listeria exposure. Biological replicates (rep) were compared based on log 2 fold change (FC) between time 10 min and 6 hr after exposure to bacteria. Each dot represents a unique peptide sequence. Peptides that were observed to be significantly upregulated or downregulated are shown, while peptide measurements that were not reproducible across both biological replicates are also shown. Dot plot axes: Log 2FC. Histogram axes: number of distinct peptides.
Figure 9A:
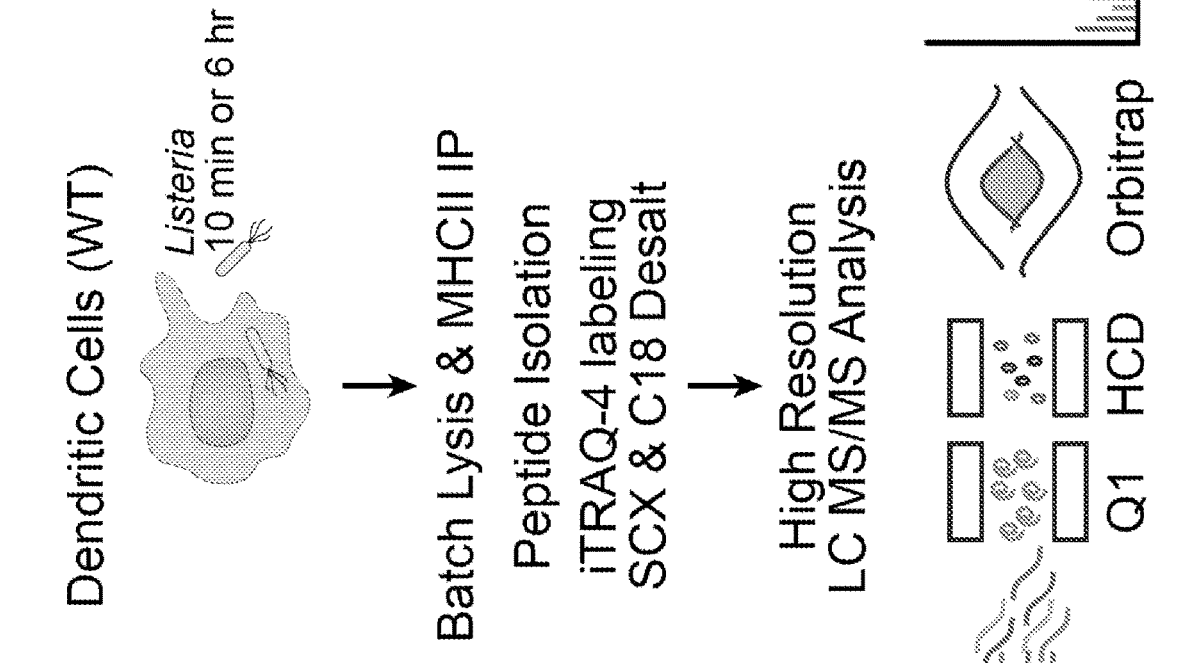
FIG. 9A shows an experimental workflow for immunopurification and sequencing of MHCII-associated peptides from murine dendritic cells. MHCII-peptide complexes were immunopurified from WT cells after a 10-minute or 6-hour Listeria treatment. Associated peptides were then acid-eluted, labeled with iTRAQ4 reagents, desalted with SCX and C18, and analyzed using high resolution LC-MS/MS.

Example 4—Validation of BOTA Epitope Predictions for *Listeria* with MHCII Peptidomics To validate BOTA, Applicants tested its performance in predicting MHCII-restricted epitopes from *Listeria monocytogenes*, one of the most common foodborne pathogens associated with a relatively high mortality rate (Scallan et al., 2011). Despite the epidemiological impact of listeriosis, the number of experimentally validated CD4 T cell epitopes encoded within the *Listeria* genome is limited. Thus, Applicants first sought to identify MHCII-associated peptides in BMDCs exposed to live *Listeria* by peptidomics. In these experiments, primary BMDCs were exposed to live *L. monocytogenes* for 10 minutes or 6 hours prior to immunoprecipitation of mature peptide-MHCII complexes with monoclonal Y3P antibody (Janeway et al., 1984). Associated peptides from biological replicates of the 10-minute and 6-hour timepoints were analyzed using mass spectrometry (LC-MS/MS) (FIGS. 9A and B). These experiments discovered 48 unique peptides derived from exogenous *Listeria* proteins. Twenty-nine of these peptides represented nested sets derived from 7 unique proteins (Table 1). The second-most enriched peptide was the previously identified immunodominant epitope from listeriolysin O ($LLO_{190-205}$), while the remaining peptides represented novel candidate antigens. Notably, all of the detected peptides were derived from secreted proteins or cell wall proteins. These observations highlight the importance of epitope accessibility for antigen presentation. Together, this dataset represents the first example of identifying processed peptide antigens derived from a live bacterial pathogen.

Figure 9C:
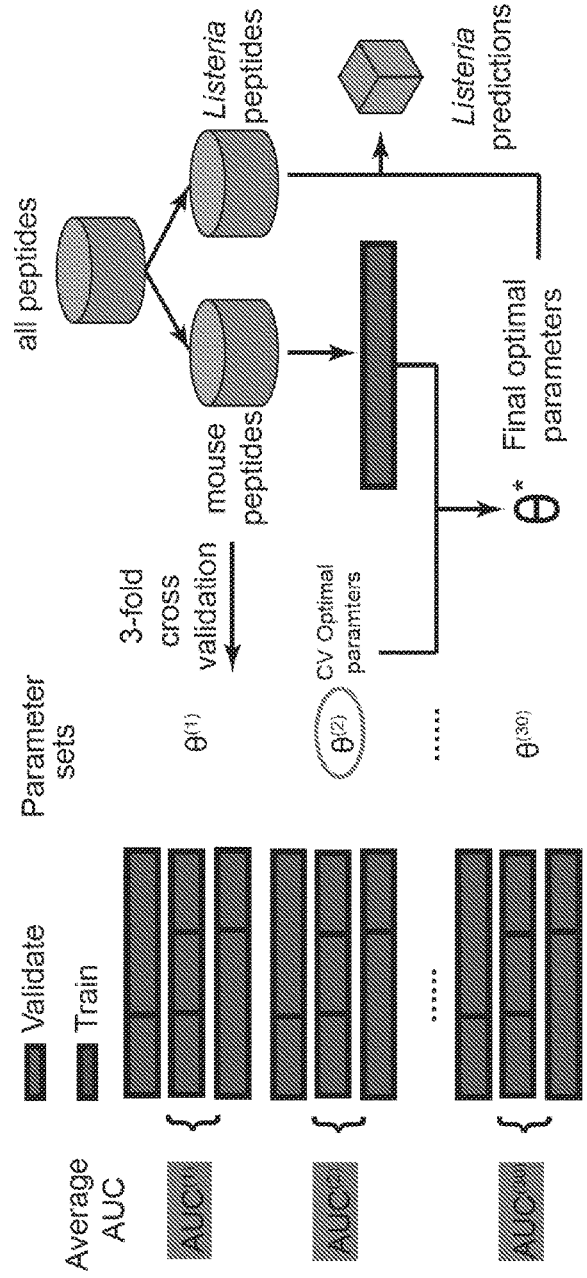
FIG. 9C shows predictions for Listeria epitopes were made using the deep neural network core of BOTA.
Figure 9E:
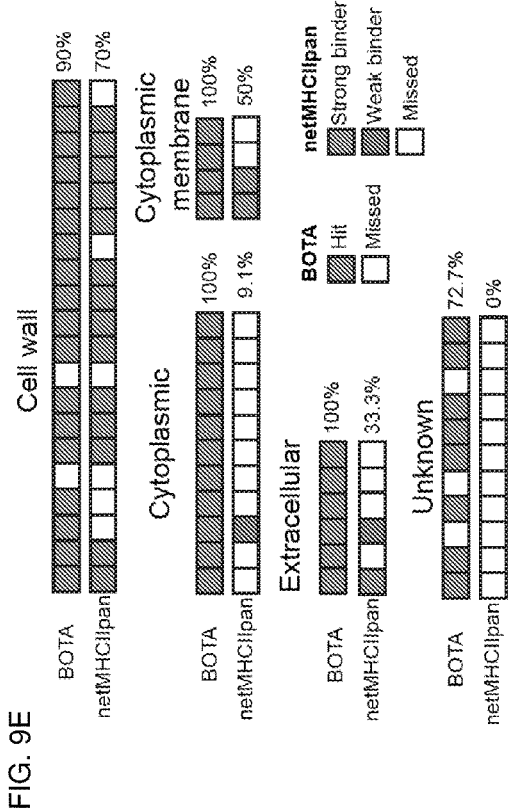
FIG. 9E shows a comparison of predictions for Listeria epitopes in proteins identified by proteomics. Peptides are split into categories based on the protein's subcellular localization using PSORTb.
Figure 9D:
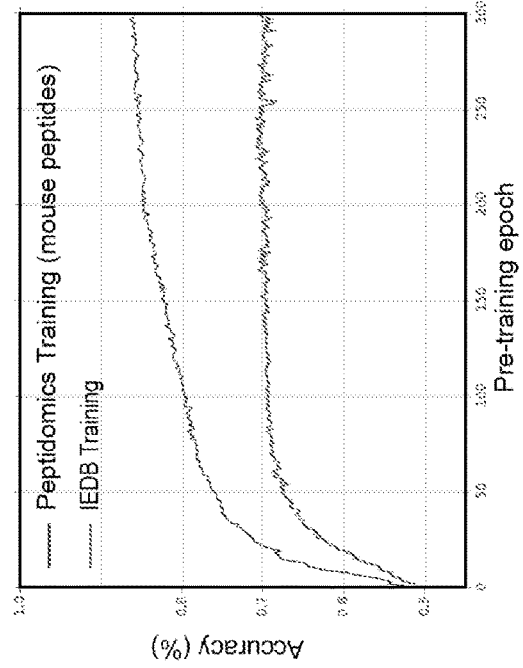
FIG. 9D shows that the BOTA model pre-training accuracy plateaus after 200 epochs in cross-validation. The model was trained using the mouse peptides captured in BMDCs infected by Listeria (line); in contrast, the same model trained solely on Immune Epitope Database (IEDB) data reached a plateau at approximately 70%, signifying a 15% gap in accuracy.

Applicants next compared *Listeria* peptides identified by MHCII peptidomics with BOTA predictions. Nine out of 17 BOTA-predicted epitopes were validated by MHCII peptidomics (Table 2). Of the 35 unique *Listeria* peptides identified by proteomics with an adjusted p value<0.05, BOTA-predicted epitopes were present in 28. Applicants compared the prediction accuracy of the BOTA model between training with two data sets: peptides captured in murine dendritic cells ("Peptidomics Training") and MHCII-associated peptides from the Immune Epitope Database ("IEDB Training") (FIG. 9D). Both BOTA pre-training accuracies plateaued after 200 epochs, but BOTA training with the peptidomics data increased prediction accuracy over training with IEDB data by 15%. Notably, BOTA showed strong improvement over the current prediction methods, including the state-of-the-art netMHCIIpan (Andreatta et al., 2011) (FIG. 9E). Thus, BOTA performs well in predicting dominant CD4 T cell epitopes (Table 2).

Improvement in prediction accuracy by BOTA also signifies the successful application of a deep neural network to a complex biomedical problem. Previous efforts using traditional neural networks or hidden Markov models were limited by their ability to extract highly abstract features, thus leading to insufficient insights into epitope prediction (Wang et al., 2008). The important innovation of BOTA is its utility in predicting CD4 T cell epitopes for virtually any MHCII allele and any antigen source, including commensal microbes, pathogens, autoantigens, and tumor antigens.

Figure 10D:
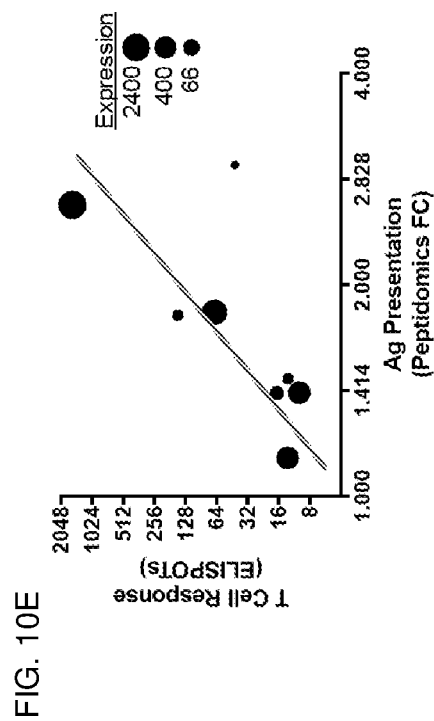
FIG. 10—BOTA and MHCII peptidomics accurately predict immunodominance in vivo.
FIG. 10A shows epitope mapping and domain structure of Listeria antigens indicate preferential presentation of surface-exposed and secreted proteins.
FIG. 10B shows that immunodominance of epitopes was determined by infecting mice with Listeria. At day 7, splenocytes were harvested and restimulated with the indicated peptides for quantification of the T cell response by IFNγ ELISPOT. Data represent the mean number of spots per $1\times10^5$ CD4 T cells±sd for n=6 mice.
Figure 10E:
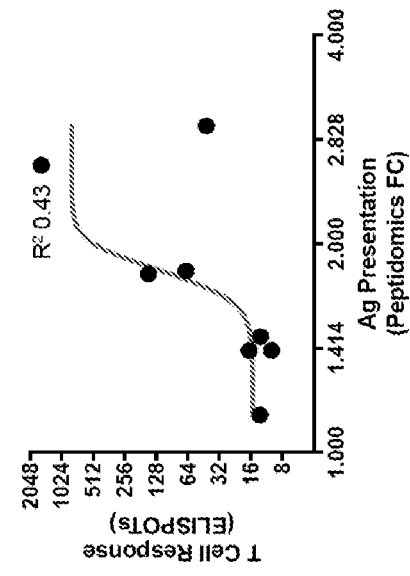
Figure 10B:
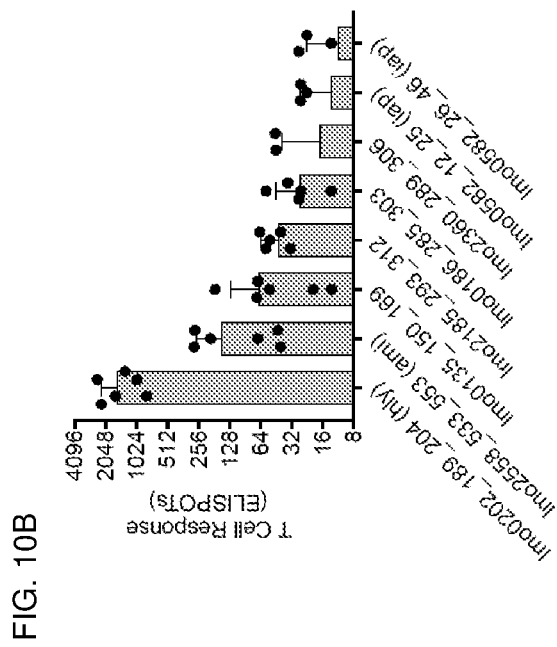
Figure 10C:
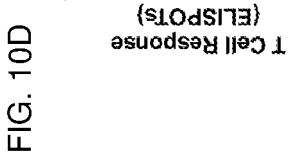

Example 5-BOTA and MHCII Peptidomics Predict Immunodominance of *Listeria* Epitopes In Vivo Given that MHCII peptidomics and BOTA successfully identified *Listeria* peptides and features associated with efficient antigen presentation, Applicants sought to measure T cell responses to these epitopes in vivo. To quantify the CD4 T cell response directed to the top eight candidate *Listeria* epitopes, mice were sacrificed seven days after intraperitoneal (i.p.) infection with *Listeria*. T cells were restimulated in vitro with synthetic peptides, and IFN-γ responses were enumerated by ELISPOT. Robust responses were detected against four of the eight epitopes (lmo0202, lmo2558, lmo2185, lmo0135) (FIG. 10A). The remaining four epitopes elicited weaker responses near the limit of detection for ELISPOT (FIG. 10B). Notably, the T cell response to these eight candidate epitopes correlated remarkably well with their abundances detected by MHCII peptidomics (FIG. 10C). RNA expression of *Listeria* antigens (Chatterjee et al., 2006) correlated with the corresponding T cell response to a lesser extent (FIG. 10D), although low expression did not appear to preclude antigenicity (FIG. 10E).

Figure 17:
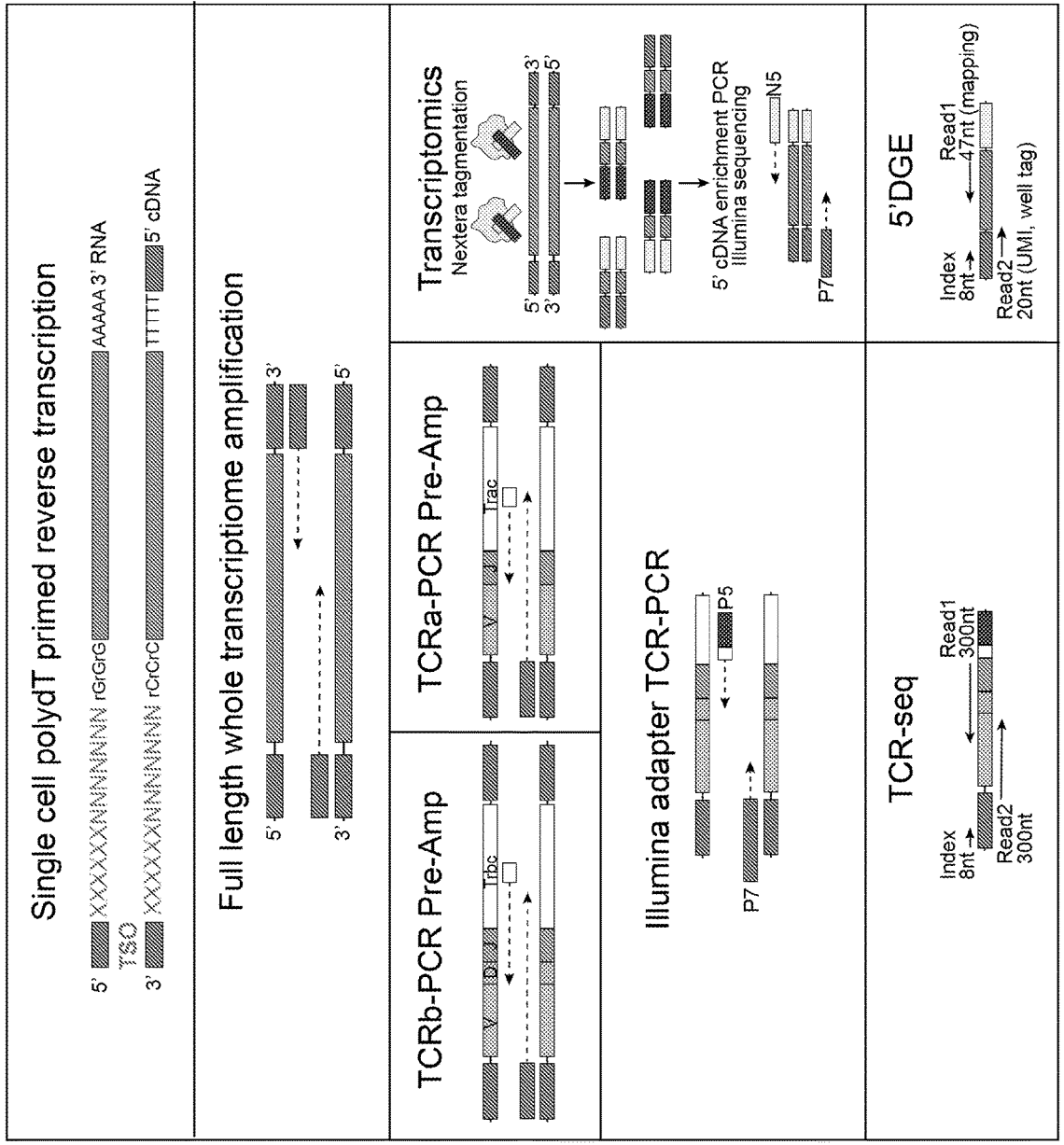
FIG. 17—Strategy for TCRseq coupled with whole transcriptome sequencing. Single T cells are FACS-sorted into individual wells of 384-well PCR plates. First-strand cDNA is primed with polydT oligonucleotide appended with adaptor. Template switching during reverse transcription appends the cDNA with well barcodes (XXXXXX), unique molecular identifiers (NNNNNNN), and adapters. Whole transcriptome amplification (WTA) is then performed with PCR primers complementary to the sequencing adapters. After WTA, individual wells are pooled, DNA is purified, and then divided into three fractions to produce sequencing libraries for TCR-alpha, TCR-beta, and 5' digital gene expression (5'DGE). TCR pre-amplification is performed with PCR primers complementary to 5' adapter and TCR constant domain. A second round TCR PCR is then performed with PCR primers containing full-length P7 Illumina sequencing adapters that are complementary to 5' template DNA and a nested primer complementary to the TCR constant domain and appended with P5 illumina sequencing adapters. TCR libraries were sequenced with a 608 cycle MiSeq run. 5'DGE libraries are produced by tagmentation of pooled WTA reactions. A 5' cDNA enrichment PCR adds full length P7 Illumina sequencing adapters and N5 Nextera sequencing adapters. 5'DGE libraries were sequenced with a 75 cycle NextSeq run.

Example 6—Integration of T Cell Phenotype with TCR Specificity in the *Listeria* Response Having demonstrated the utility of BOTA for predicting bacterial epitopes, Applicants next sought to rigorously characterize the antigen-specific T cell response to *Listeria*. Standard approaches for defining immunodominance, such as ELISPOT, rely on ranking candidate epitopes based on the magnitudes of the T cell responses they elicit in vivo. However, such approaches require prior knowledge of TCR specificity and T cell phenotype (cytokine profile) and cannot account for T cell responses to epitopes that have not been tested, but may be dominant. To address these limitations, Applicants developed a procedure for single cell analysis of T cell phenotypes matched to their corresponding TCR sequences. This TCRseq approach allows for simultaneous enumeration of T cell clonal frequency and cytokine profiles (FIG. 17). Dominant TCR clones can then be screened for reactivity against *Listeria* epitopes.

Figure 11D:
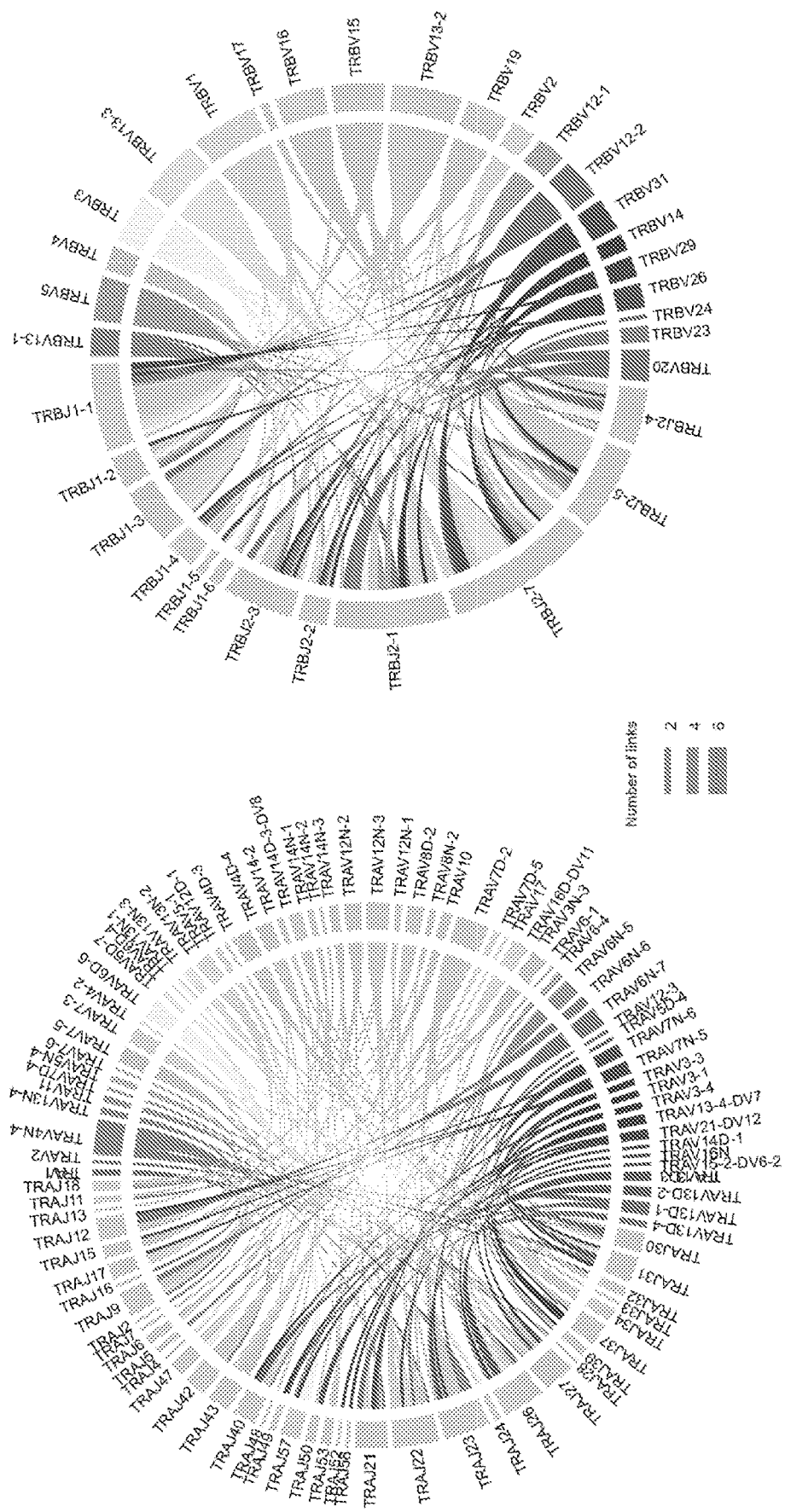
FIG. 11D shows circos plots of the linkages between the two segments in the alpha chain (top) and beta chain (bottom). Segment J's coded in grey and segment V's are differentially shaded. Ribbons link two chains with thickness proportional to the number of corresponding V/J pairs observed, and with the shading identical to the V chain.

Towards this end, Applicants infected mice with *Listeria* and FACS-sorted single CD4 T cells for transcriptomics and TCR sequencing. Based on transcriptional profiles, T cells clustered into distinct functional states (FIG. 11A), with a distinct profile for activated Th1 cells expressing Ifnγ (FIG. 11B) and Tbx21 (FIG. 11C). Amongst these T cells, the TCR repertoire was remarkably diverse with a maximal clonal frequency of ~2% (FIG. 11D).

Figure 12A:
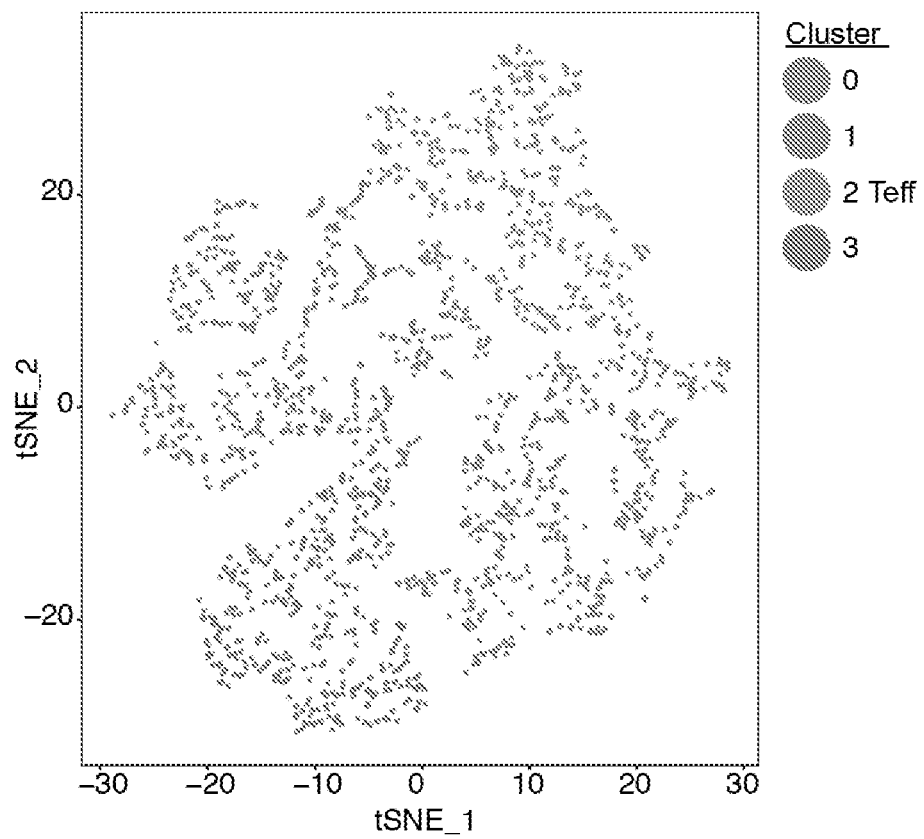
FIG. 12A shows a tSNE plot derived from T cell transcriptomes identifies distinct cell states that cluster according to unique signatures. Each dot represents a single cell that is shaded according to gene signature.
Figure 12B:
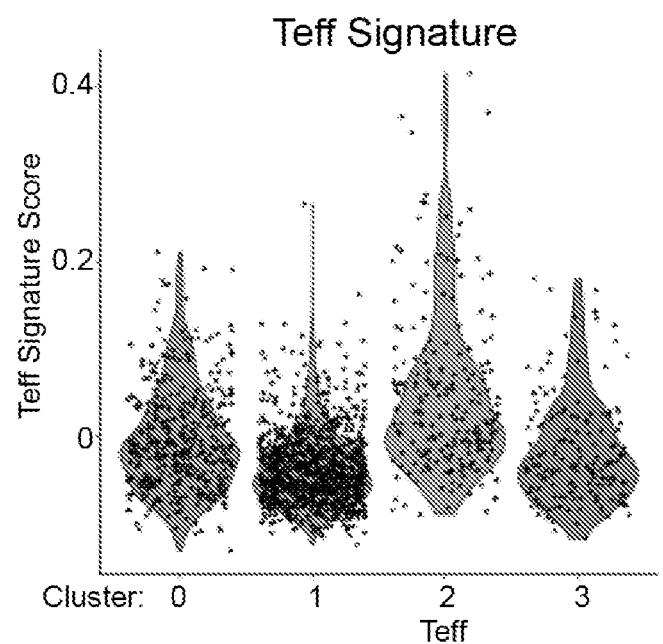
FIG. 12B shows violin plots displaying Teff signature score derived from ImmGen. Each dot represents a single cell classified by clusters defined by tSNE.
Figure 12C:
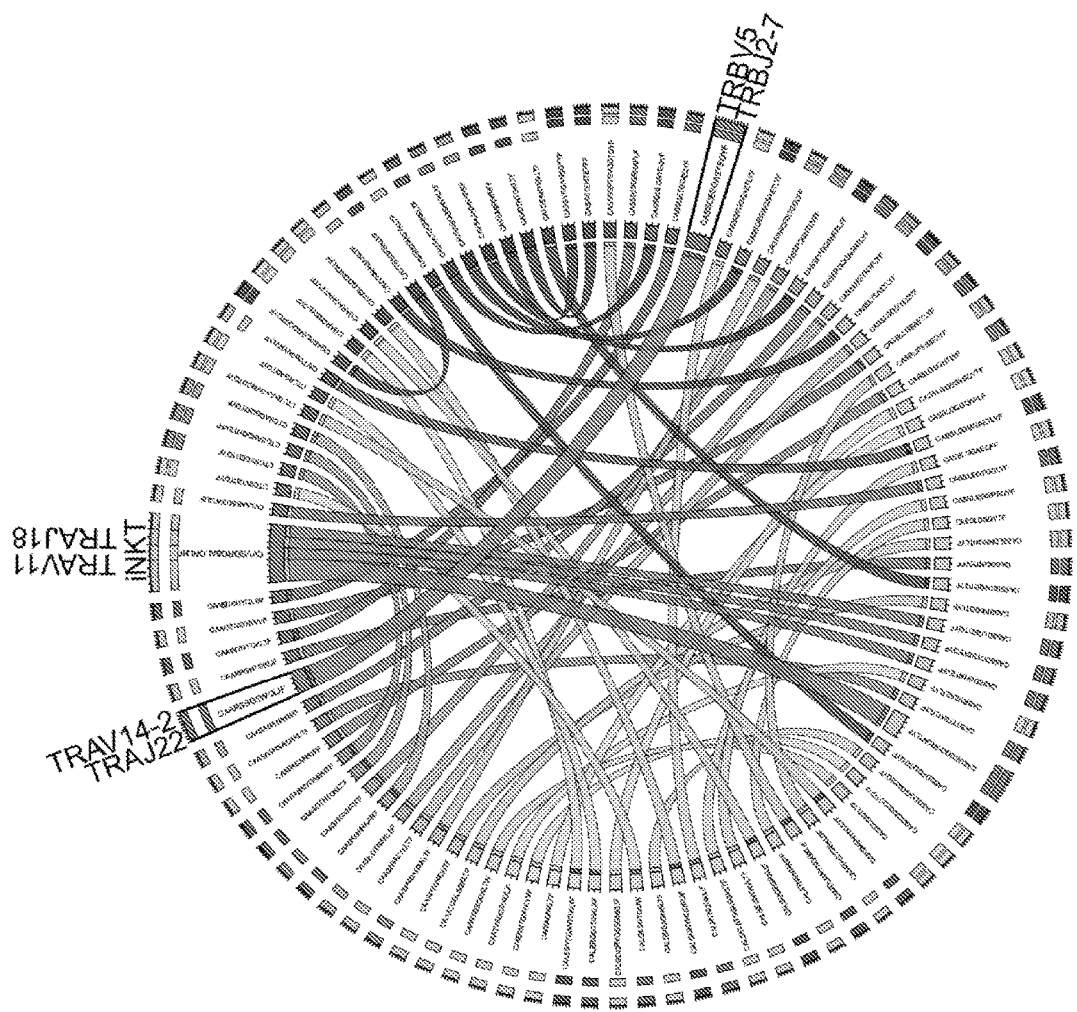
FIG. 12C shows circos plots of the linkages between the TCR alpha chain CDR3 and TCR beta chain CDR3. Ribbons link two chains with thickness proportional to the number of corresponding TCR pairs observed. Dominant TCR clones are labeled according to TCR gene segment usage. Starting with the sequence listed next to the TRBV5/TRBJ2-7 TCR, the plot lists SEQ ID NOs: 15101-15197, going in clock-wise order.

Based on unbiased clustering of transcriptional profiles, T cells partitioned into four distinct subsets (FIG. 12A). To identify the activated T effector (Teff) cluster, Applicants generated a per-cell Teff score that was based on the gene expression signature derived from ImmGen datasets comparing CD4 Teff splenocytes (day 8 after lymphocytic choriomeningitis virus, LCMV, infection) versus naïve CD4 T splenocytes (Heng et al., 2008). These analyses identified cluster 2 as being enriched for Teff cells expressing signature activation markers (Ccl5, Nkg7, Ikzf1), genes that regulate ER homeostasis (Calr, Pdia3), and genes that control cellular metabolism (Acly, Akr1a1) (FIG. 12B). Amongst these T cells, the TCR repertoire was remarkably diverse with a maximal clonal frequency of ~3% for conventional T cells. The most abundant conventional TCR (TRAV14-2TRAJ25|TRBV5TRBJ2-7) was detected exclusively in cells residing in Teff cluster 2. By contrast, NKT cells expressing the invariant alpha chain Trav11Traj18 were found scattered throughout clusters (FIG. 12C).

Figure 13A:
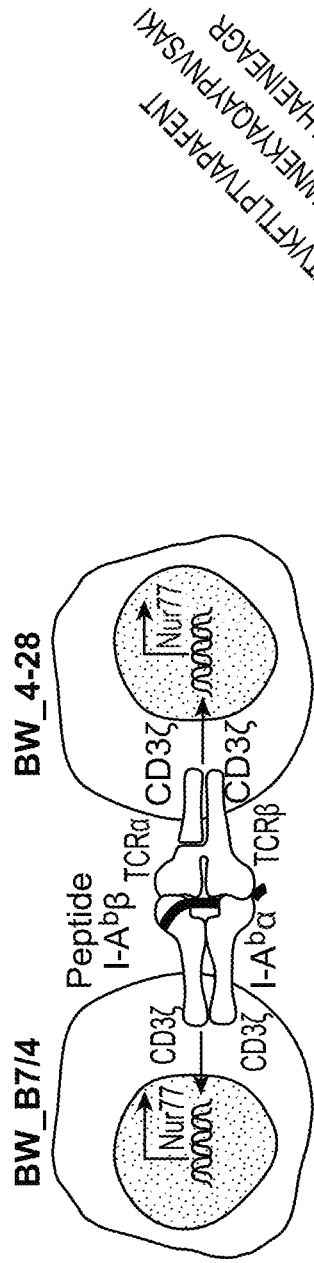
FIG. 13A shows the screen overview. BW5147_B7-4 cells were transduced to express peptide epitopes fused in-frame with the I-A$^b$beta chain bearing CD3zeta cytoplasmic domains. BW5147_CD4-28 cells were transduced to express chimeric single chain TCRs bearing the transmembrane and cytoplasmic domains of CD3zeta. In this coculture system, cognate antigen recognition results in T cell activation characterized by IL-2 production.
Figure 13B:
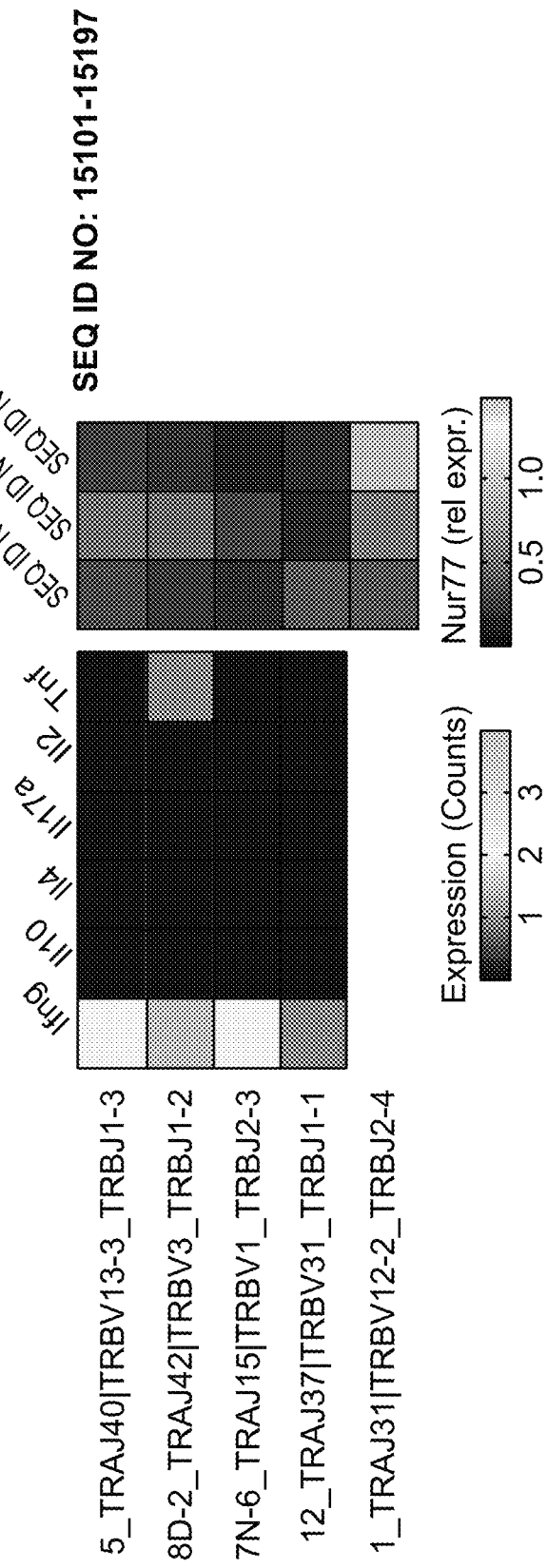
FIG. 13B shows that TCRs associated with high Ifng expression, as identified in CD4 T cells from *Listeria*-infected mice, were screened against *Listeria* epitopes. The positive control OT2 TCR reacted robustly with OT2 peptide I-A$^b$. T cell activation was measured in duplicate by induction of Nur77 expression relative to beta actin. The right side of panel B lists SEQ ID NOs: 15198-15200, from left to right.

Using TCRseq and whole transcriptome data, Applicants prioritized the most abundant TCR to test for reactivity against BOTA predictions (FIGS. 13A and 14A). In designing a screening modality, Applicants took into consideration the low affinity interaction between TCRs and peptide antigen presented on MHCII. This interaction occurs between multiple TCRs and pMHCII complexes within lipid bilayers on adjacent cells. Avidity and kinetics of engagement/disengagement elicit a TCR signaling cascade that amplifies the input signal. Therefore, Applicants designed a heterologous expression system in which TCR-negative BW5147-CD4-CD28 cells are transduced to express single chain TCRa and TCRβ fused to the cytoplasmic tail of CD3ζ. Functional TCRαβ proteins in BW5147-CD4-CD28 cells engage cognate peptide-MHCII on antigen presenting cells to initiate a TCR signaling response that results in expression of IL-2 or the activation marker Nur77 (Nr4al). As a source of surrogate antigen presenting cells, Applicants utilized HEK293T cells or BW5147-B7/4 cells transfected or transduced to express I-A$^b$α-CD3ζ and candidate peptide antigens fused to I-A$^b$β-CD3ζ. For HEK293T experiments, Applicants selected the most abundant TCR clone from TCRseq to test for reactivity with 4 Listeria pMHCII complexes predicted by BOTA (FIG. 14B). For BW5147-B7/4 experiments, Applicants generated 4 TCRs from TCRseq showing high IFN-γ expression and 2 Listeria pMHCII complexes predicted by BOTA (FIG. 13B). As a positive control, Applicants demonstrated that the OT2 TCR expressed in BW5147-CD4-CD28 cells reacted with ovalbumin peptide in the context of I-A$^b$ by inducing IL-2 secretion or Nur77 expression (FIGS. 13B and 14B) and IL-2 production. Among the four candidate Listeria-specific TCRs, three showed evidence of weak reactivity to LLO (FIG. 13B). Similarly, a previously identified TCR (LLO_118) (Weber et al., 2012) reacted robustly with LLO (FIG. 14B). The top TCR candidate identified by TCRseq also reacted with LLO, according to induction of IL-2 and binding to LLO-I-A$^b$ tetramers (FIGS. 14B and C). These findings are consistent with the notion that the primary T cell response to Listeria is characterized by numerous weakly-reactive TCRs. In agreement with this conclusion, the TCRseq experiments revealed a remarkably diverse TCR repertoire associated with the primary Th1 response to Listeria. Taken together, these experiments establish the feasibility of integrating population-level TCR repertoires with antigen specificity by screening individual TCRs for reactivity against candidate antigens predicted in silico.

Example 7—Identification of Commensal Epitopes

Figures 15A, 15B:
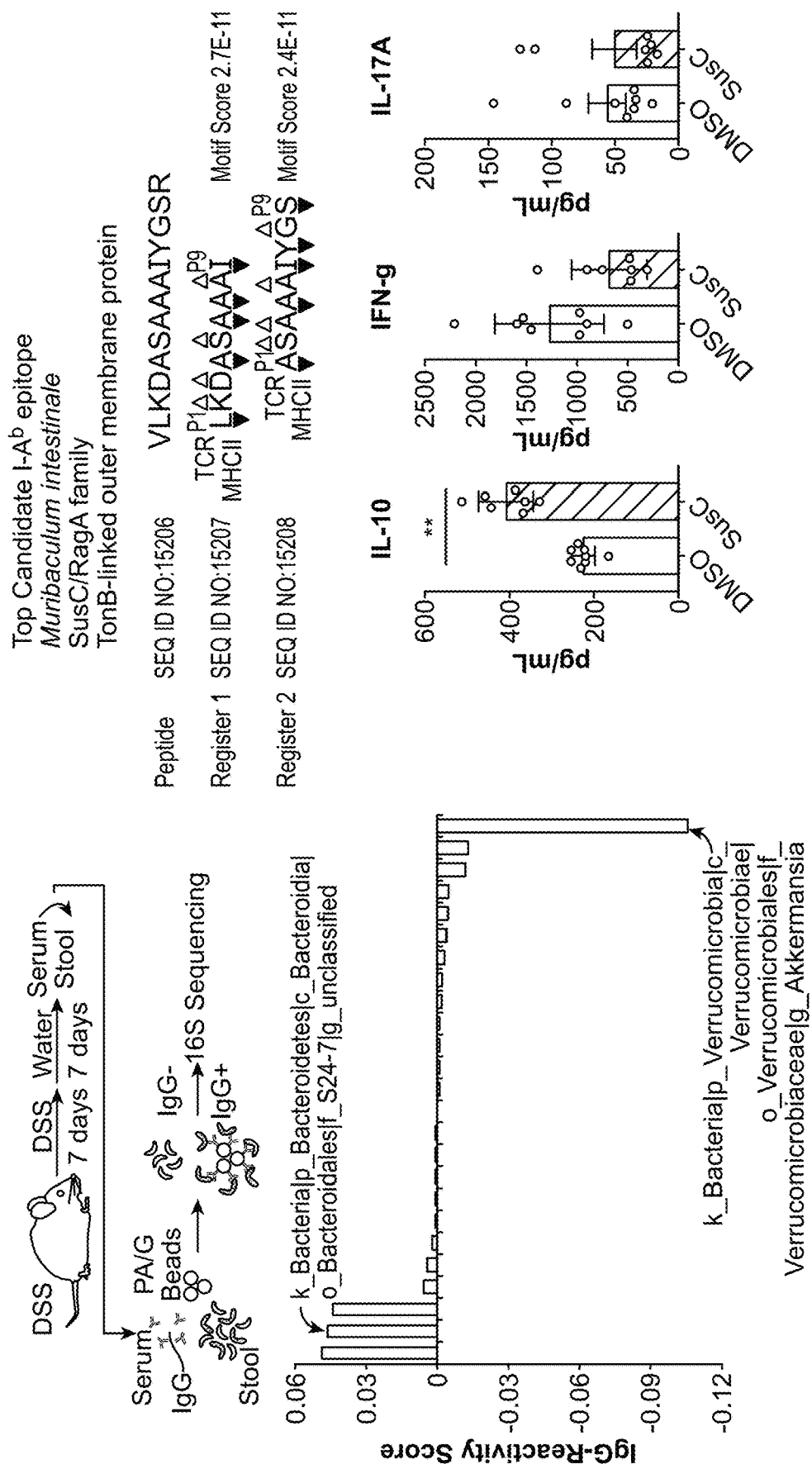
FIG. 15A shows that mice were administered DSS to induce colitis prior to analysis by SICC-seq. At day 14, serum was collected and incubated with stool to allow binding of IgG with commensals. IgG-positive and -negative fractions were separated with magnetic beads covalently attached to protein A/G. The immunogenicity of Bacteroidales was demonstrated by IgG-reactivity score (relative abundance in IgG-positive minus IgG-negative fractions) derived from 16 s sequencing.
FIG. 15B shows that BOTA identified SusC, a highly represented epitope within and a 1 cross Bacteroidales genomes, including the murine commensal *Muribaculum intestinale*. Splenocytes from naive mice were harvested and stimulated in vitro with the indicated peptide. Cytokines were measured 24 hours later by cytometric bead array. IL-10 production was selectively induced by SusC peptide, suggesting that host T cells recognize and tolerate Bacteroidales. Shown are SEQ ID NOs: 15206-15208, starting with the top peptide.

Having validated BOTA epitope predictions for a common pathogenic bacterium, Applicants sought to explore the complex relationship between commensal microbes and host adaptive immunity. In this context, the intestinal microbiome fine-tunes inflammatory thresholds, primes innate immune effector function, and shapes the adaptive immune response through selection and tolerization of lymphocytes (Palm et al., 2015). Thus, the dynamic role of the microbiome in immune education impacts organ systems throughout the body, and in turn, many disease states (Hall et al., 2017). Applicants reasoned that because the host adaptive immune system continuously interacts with the microbiome, monitoring the magnitude and nature of the T cell response to specific commensal antigens can reveal the health status of the immune system. In the state of health, the adaptive immune system maintains tolerance to local gut antigen exposure and protection from systemic infection. The sheer number of bacterial species and diversity of protein-coding elements in the microbiome represents an enormous search space. Towards identifying immunogenic commensals, Applicants developed "serum immunoglobulin commensal capture and sequencing" (SICC-seq). Mice were administered a course of dextran sodium sulfate (DSS) to induce barrier breach and allowed to recover for 7 days. Serum was then harvested from mice and incubated with stool to opsonize commensals. IgG-positive microbes were enriched by selection with Protein A/G-coupled magnetic beads and analyzed along with total stool by 16S rRNA sequencing. Using this approach, Applicants demonstrated that induction of colitis with DSS elicits a systemic T cell-dependent IgG response that preferentially targets bacteria in the genus Bacteroidales (FIG. 15A). In contrast, Akkermansia evade this response, likely due to their ability to induce T cell tolerance and IgA responses under homeostatic conditions (before colitis) (FIG. 15A). Having established the immunogenicity of Bacteroidales, Applicants employed BOTA to predict T cell epitopes from the dominant species inhabiting mice (Ormerod, et al., 2016) (FIG. 15B) and identified a highly abundant epitope in a SusC-like protein that is conserved across the Bacteroidales genus and often duplicated within species (FIGS. 15B and 22). To determine if T cells recognize this SusC epitope in vivo, Applicants harvested splenocytes from a naïve mouse and stimulated them with SusC peptide in vitro. Importantly, the SusC peptide induced IL-10 production by T cells, indicating a homeostatic relationship between host T cells and Bacteroidales in a normal healthy mouse (FIG. 15C). Applicants hypothesize that these interactions extend to many other commensals, and that tumultuous relationships between T cells and commensals typify immune pathologies and autoimmunity.

Example 8—Discussion

Host-microbe interactions cooperatively influence the specificity and diversity of the T cell response. A deeper understanding of this relationship requires new approaches for unbiased antigen discovery, defining the features of antigenicity, and elucidating host pathways underlying preferential selection of these features. Toward these objectives, Applicants report a highly quantitative adaptation of MHCII peptidomics. By recapitulating the interaction between primary murine BMDCs and live L. monocytogenes, Applicants identified four dominant CD4 T cell epitopes and established their immunodominance hierarchy in vivo. In addition, MHCII peptidomics identified over 3600 autologous mouse peptides, which provided an exceptionally detailed view of lysosomal function.

As a consequence of deep profiling of the MHCII immunopeptidome, Applicants generated a rich dataset for identifying features associated with of antigen processing and developed BOTA as a predictive algorithm, incorporating several important attributes of immunodominant epitopes revealed by proteomics. Based on observations from MHCII peptidomics, optimal epitopes tend to (1) derive from secreted proteins or extracellular regions of cell wall proteins in bacteria, (2) have a primary sequence structure that conforms to a defined MHCII binding motif, (3) be located more than 8 amino acids away from transmembrane domains, and (4) have tertiary structure characteristics that promote accessibility to the MHCII binding groove and the enzymes required for proteolytic processing. Notably, Applicants did not identify any features of antigenicity associated with protease specificity, as lysosomal endopeptidases and exopeptidases are highly diverse with respect to substrate selectivity. Importantly, all of the features identified by peptidomics are readily identifiable at the level of DNA sequence; therefore, the only input requirement for BOTA is an annotated genome. Owing to this, BOTA enables large-scale mapping of the immunodominant epitope landscape for any bacterial species or collection of species, such as the human microbiome. Taken together, Applicants demonstrate the utility of MHCII peptidomics for training a deep neural network that specifically identifies candidate epitopes with key features associated with immunodominance and antigenicity. Furthermore, MHCII peptidomics serves as a powerful tool for unbiased discovery of complex pathogen antigens and for interrogation of host pathways underlying human disease.

Inherent to antigen discovery is the significant challenge of validating epitope predictions. Conclusive validation of epitope immunogenicity requires demonstration that a measurable T cell response is elicited in vivo. To address this challenge, Applicants developed an approach for identifying and integrating TCR repertoire, phenotype, and antigen reactivity. Coupling TCRseq with whole transcriptome profiling enabled at the single cell level enabled assignment of transcriptional phenotypes to individual TCRs. While Applicants employed this approach to identify TCRs associated with CD4 T effector cells (e.g., Th1 cells) derived from *Listeria*-infected mice, it is applicable to any immune cell type and any phenotype that can be defined at the level of the transcriptome, including Treg or Th17. Such determinations are challenging in T cell hybridomas because the primary T cell phenotype is not preserved after immortalization. Moreover, generating T cell hybridomas is an inefficient process that is further biased by chromosome loss, drug selection, and screening for antigen reactivity. In contrast, TCRseq is comparatively efficient, which is an important consideration in the context of limited T cell input from precious clinical specimens. A small tissue biopsy is sufficient to generate a permanent archive of TCR sequences matched with transcriptional profiles that can be used to screen defined TCRs for reactivity against candidate epitopes. Thus, immunodominance can be unambiguously defined in the context of epitopes that elicit the strongest T cell responses, as determined by clonal frequency and/or absolute numbers.

Figure 18:
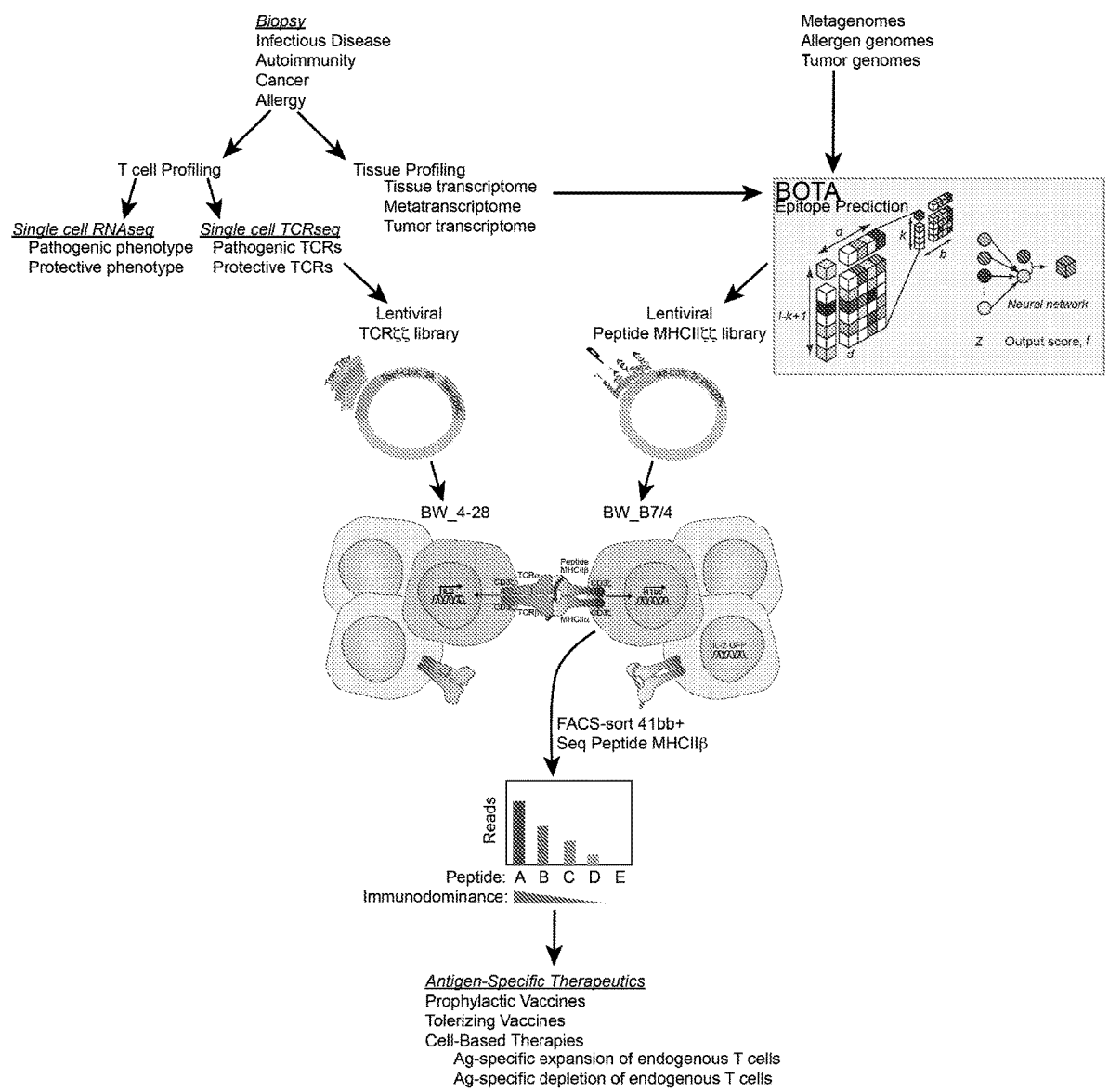
FIG. 18—BOTA Applications: Strategy for specifying immunodominance hierarchies at scale.
Figure 19A:
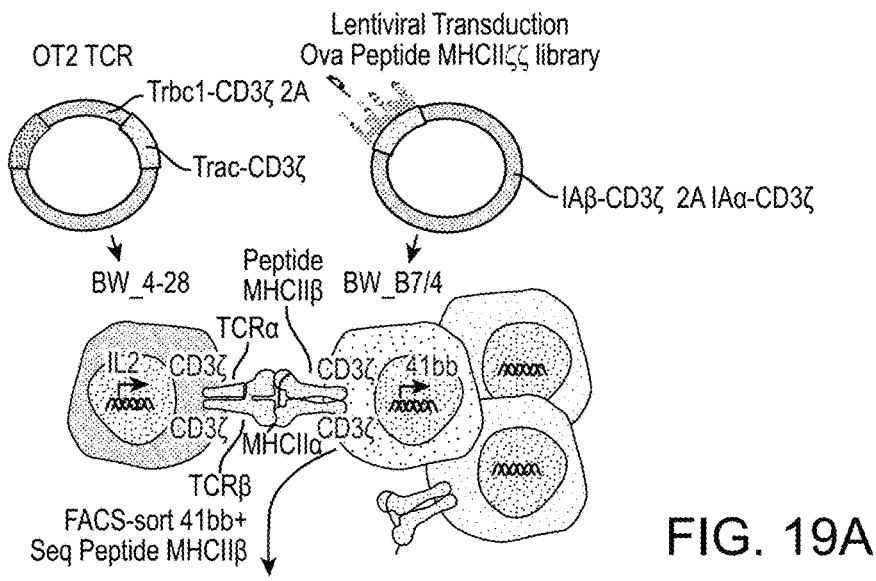
FIG. 19A shows an example schematic overview. Peptide-MHCIIζζ cDNA libraries encoding mutated ovalbumin peptides (Ova 323-339) were delivered to BW_B7/4 T cells by lentiviral transduction. These responder cells were cocultured with BW_4-28 stimulator cells expressing a single chain OT2
Figure 19B:
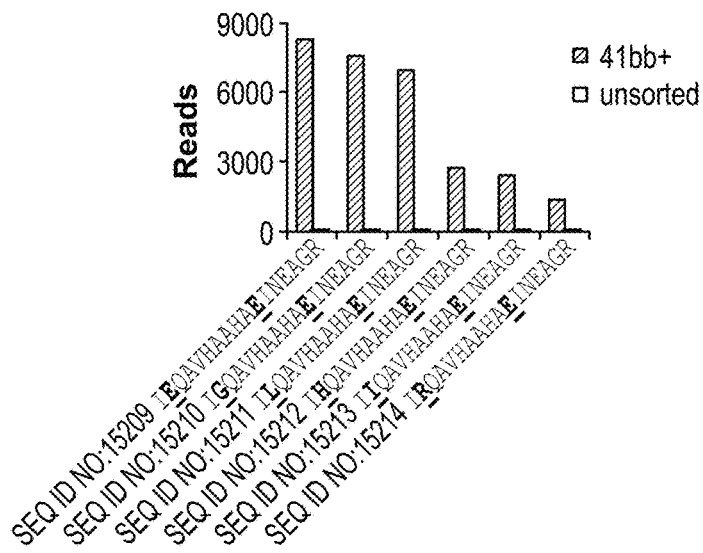
FIG. 19B shows that Illumina sequencing reads were translated in silico and quantified to compare the abundances of Ova-encoding mutants within the 41bb+ samples relative to unsorted samples. Shown are SEQ ID NOs: 15209-15214, from left to right.
Figure 19C:
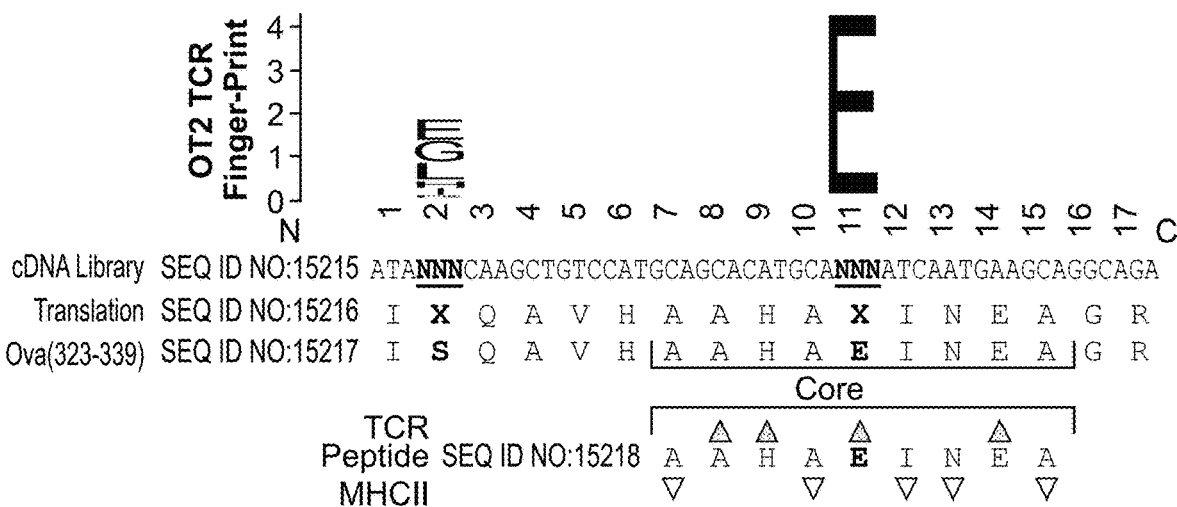
FIG. 19C shows that a glutamate at amino acid position 11 in Ova (323-339) is strictly required for functional interaction with the OT2 TCR. This position represents an outward-facing TCR contact reside within the core MHCII-binding register of Ova(323-339). In contrast, position 2 of Ova(323-339) falls within a region flanking the core MHCII-binding motif and can accommodate several different amino acids while retaining functional interaction with the OT2 TCR. This observation is consistent with the notion that position 2 does not contribute to recognition by the OT2 TCR. Shown are SEQ ID NOs: 15215-15218, starting with the top sequence.

Here, Applicants develop a technology platform with broad utility for antigen discovery. BOTA is capable of predicting CD4 T cell epitopes from multiple sources, including genomes or transcriptomes derived from pathogens, the microbiome, allergens, tumors, and tissue biopsies (FIG. 18). By coupling BOTA predictions with TCRseq from matching specimens, Applicants enable generation of DNA-encoded epitope and TCR libraries that can be screened to define antigen specificity and quantify immunodominance. The screening platform developed can be implemented in arrayed format (well-based screening of individual TCRs by peptide-MHCII antigens) or in a pooled format where cells expressing TCR libraries are cocultured with cells expressing peptide-MHCII libraries. For example, Applicants have performed TCR fingerprinting by coculturing stimulator cells expressing the OT2 TCR with responder cells displaying a library of ovalbumin peptide mutants expressed as a fusion protein with MHCII ectodomain linked to the CD3ζ cytoplasmic domain. After FACS-sorting activated responder cells (41bb+) that had engaged in a productive interaction with stimulator cells, Applicants sequenced the Ova-MHCIIζ libraries to recover the known cognate peptide ligand for the OT2 TCR (FIG. 19). In this context, it is possible to simultaneously screen thousands of epitopes for reactivity with a given TCR.

With the new approaches to effectively predict T cell epitopes and validate TCR reactivity as disclosed herein, it is possible to identify antigenic determinants in bacterial pathogens and even complex communities such as the intestinal microbiome. Applicants identified an I-$A^b$-restricted epitope in a SusC-like protein derived from Bacteroidales that is associated with IL-10 producing T cells derived from mouse spleen. Notably, these experiments identified systemically circulating T cells with reactivity to a benign commensal species. The findings highlight the intimate relationship between commensals and the host adaptive immune system. In this context, previous studies in mouse models have demonstrated that a systemic T cell-dependent IgG response to commensals is cross-protective against pathogen infection (Zeng et al., 2016). Similarly, IgG-reactivity with commensals has been shown to be widespread in healthy humans and qualitatively perturbed in the context of autoimmunity (Christmann et al., 2015; and Stoll et al., 2014). While the understanding of host-commensal mutualism is in its infancy, future research stands to reveal how this relationship promotes homeostatic immune regulation or precipitates immune dysfunction. New approaches to antigen discovery portend opportunities for biomedical research, including vaccine development (prophylactic or tolerizing) and antigen-specific T cell therapies aimed at expanding or deleting endogenous T cells with defined antigen specificities.

The improvement on prediction accuracy by BOTA also signifies the successful application of deep neural network in solving complex biomedical problems. Previous efforts using traditional neural networks or hidden Markov Models were limited by their ability to extract highly abstract features, thus leading to insufficient insights into epitope prediction. The important innovation of BOTA, is that it can be utilized to predict CD4 T cell epitopes for virtually any MHCII allele and any antigen-source, including commensal microbes, pathogens, autoantigens, and tumor antigens. Taken together, Applicants demonstrate the utility of MHCII peptidomics for training a deep neural network that specifically identifies candidate epitopes with key features associated with immunodominance. Furthermore, MHCII peptidomics serves as a powerful tool for unbiased discovery of complex pathogen antigens and for interrogation of host pathways underlying human disease.

TABLE 1

*Listeria* epitopes discovered by MHCII peptidomics.

| SEQ ID NO: | Listeria peptide[a] | logFC[b] | adj.P.Val[c] | entry_name | core | score[d] |
|---|---|---|---|---|---|---|
| 14980 | WNEKYAQAYPNVS | 1.37728 | 7.0568E-18 | lmo0202 (hly) (LLO) | EKYAQAYPN | 9.728E-11 |
| 14981 | WNEKYAQAYPNVSAKI | 1.20234 | 1.0840E-13 | lmo0202 (hly) (LLO) | EKYAQAYPN | 9.728E-11 |

TABLE 1-continued

Listeria epitopes discovered by MHCII peptidomics.

| SEQ ID NO: | Listeria peptide[a] | logFC[b] | adj.P.Val[c] | entry_name | core | score[d] |
|---|---|---|---|---|---|---|
| 14982 | ........VERWNEKYAQAYPNVS.................... | 0.28494 | 1.6720E-01 | lmo0202 (hly) (LLO) | EKYAQAYPN | 9.728E-11 |
| 14983 | .........ERWNEKYAQAYPNVS.................... | 0.20689 | 3.6222E-01 | lmo0202 (hly) (LLO) | EKYAQAYPN | 9.728E-11 |
| 14984 | ....APGQETQHYYGLPVADSAIDR................... | 0.85608 | 3.3989E-07 | lmo2558 (ami) | YGLPVADSA | 6.385E-11 |
| 14985 | ......VWTKPNKIEGAQKISALSTY................. | -0.26248 | 2.1661E-01 | lmo2558 (ami) | WTKPNKIEG | 1.641E-11 |
| 14986 | .......ADFRYVFDTAKATAASSYPG................. | 1.56572 | 6.8456E-23 | lmo2185 | FDTAKATAA | 1.932E-10 |
| 14987 | .......ADFRYVFDTAKATAASSYPGSDETPP.......... | 1.55744 | 1.0148E-22 | lmo2185 | FDTAKATAA | 1.932E-10 |
| 14988 | ........DFRYVFDTAKATAASSYPGSDETPP.......... | 0.67777 | 9.6362E-05 | lmo2185 | FDTAKATAA | 1.932E-10 |
| 14989 | ..........RYVFDTAKATAASSYPGSDETPPVVNPGETNPP | 0.63438 | 3.1562E-04 | lmo2185 | ETPPVVNPG | 2.208E-10 |
| 14990 | ...........YVFDTAKATAASSYPGSDETPP.......... | 0.61121 | 5.4781E-04 | lmo2185 | FDTAKATAA | 1.932E-10 |
| 14991 | ..........RYVFDTAKATAASSYPGSDETPP.......... | 0.27084 | 1.9678E-01 | lmo2185 | FDTAKATAA | 1.932E-10 |
| 14992 | ........YPGSDETPPVVNPGE................... | 0.78521 | 3.8293E-06 | lmo2185 | ETPPVVNPG | 2.208E-10 |
| 14993 | ......SSYPGSDETPPVVNPGETNPP............... | 0.29186 | 1.5520E-01 | lmo2185 | ETPPVVNPG | 2.208E-10 |
| 14994 | ........YPGSDETPPVVNPGETN.................. | 1.86133 | 3.1731E-32 | lmo2185 | ETPPVVNPG | 2.208E-10 |
| 14995 | ......EVEDLNQPLAAHVNYE.................... | 0.15261 | 5.2950E-01 | lmo2185 | PLAAHVNYE | 4.828E-11 |
| 14996 | .....AVDDTTVKFTLPTVAPAFENT................. | 0.87086 | 1.9984E-07 | lmo0135 | FTLPTVAPA | 5.607E-09 |
| 14997 | ......VDDTTVKFTLPTVAPAFENT................. | 0.84368 | 5.3557E-07 | lmo0135 | FTLPTVAPA | 5.607E-09 |
| 14998 | .......DDTTVKFTLPTVAPAFENT................. | 0.78647 | 3.6883E-06 | lmo0135 | FTLPTVAPA | 5.607E-09 |
| 14999 | .....AVDDTTVKFTLPTVAPAFENTIK............... | 0.46417 | 1.2352E-02 | lmo0135 | FTLPTVAPA | 5.607E-09 |
| 15000 | ......VDDTTVKFTLPTVAPAFE................... | 0.45544 | 1.4456E-02 | lmo0135 | FTLPTVAPA | 5.607E-09 |
| 15001 | .......DDTTVKFTLPTVAPAFE................... | 0.38746 | 4.5231E-02 | lmo0135 | FTLPTVAPA | 5.607E-09 |
| 15002 | .......DDTTVKFTLPTVAPAFEN.................. | 0.25955 | 2.2271E-01 | lmo0135 | FTLPTVAPA | 5.607E-09 |
| 15003 | .........TTVKFTLPTVAPAFENT................. | 0.0598 | 8.4126E-01 | lmo0135 | FTLPTVAPA | 5.607E-09 |
| 15004 | .........DGLTWHDGKPLTADDV.................. | 1.01543 | 6.5055E-10 | lmo0135 | WHDGKPLTA | 1.053E-10 |
| 15005 | ........GTKEKVVATPVSNVSTSSA................. | 0.4888 | 7.7931E-03 | lmo0186 | VATPVSNVS | 4.923E-10 |
| 15006 | ........TKEKVVATPVSNVSTSS.................. | -0.2861 | 1.6535E-01 | lmo0186 | VATPVSNVS | 4.923E-10 |
| 15007 | .........KEKVVATPVSNVSTSS.................. | -0.20956 | 3.5407E-01 | lmo0186 | VATPVSNVS | 4.923E-10 |
| 15008 | ........GTKEKVVATPVSNVST................... | 0.03708 | 9.0585E-01 | lmo0186 | VATPVSNVS | 4.923E-10 |
| 15009 | .......GGINQAYTGSTALSDGLN.................. | 0.55469 | 2.0548E-03 | lmo2360 | YTGSTALSD | 7.495E-11 |
| 15010 | ........GINQAYTGSTALSDG.................... | 0.26067 | 2.2070E-01 | lmo2360 | YTGSTALSD | 7.495E-11 |
| 15011 | .......GGINQAYTGSTALSDG.................... | 0.23863 | 2.7631E-01 | lmo2360 | YTGSTALSD | 7.495E-11 |
| 15012 | .........STVVVEAGDTLWGIAQSKGTT............. | 0.48949 | 7.6998E-03 | lmo0582 (lap) | VEAGDTLWG | 3.576E-12 |
| 15013 | ........IAVTAFAAPTIASA.................... | 0.18053 | 4.4262E-01 | lmo0582 (lap) | FAAPTIASA | 8.274E-09 |
| 15014 | ........VETKADIDALSLLSDKIFVTNQT............ | 1.05574 | 1.1992E-10 | lmo1451 (ispH) | DIDALSLLS | 1.864E-11 |

TABLE 1-continued

Listeria epitopes discovered by MHCII peptidomics.

| SEQ ID NO: | Listeria peptide[a] | logFC[b] | adj.P.Val[c] | entry_name | core | score[d] |
|---|---|---|---|---|---|---|
| 15015 | .......EAKELVDNAPKALKEGIA............... | 0.9296 | 2.0391E-08 | lmo0251 (rplL) | DNAPKALKE | 1.319E-10 |
| 15016 | .....SNVNHVLDIGYGGGSnVKN............... | 0.227 | 3.0478E-01 | lmo1715 | IGYGGGSnV | 1.796E-12 |
| 15017 | ............EVVYHNMKQDLE............... | -0.17079 | 4.7439E-01 | lmo2411 | EVVYHNMKQ | 5.047E-14 |
| 15018 | DGLKAGEHFFAAGKDWPDAIYANGDEVAAGVmYH........ | -0.42712 | 2.3527E-02 | lmo2737 | KDWPDAIYA | 4.863E-11 |
| 15019 | ...........EILLQKPnGERLTSFITL............ | -0.04842 | 8.7532E-01 | lmo0429 | ILLQKPnGE | 2.664E-12 |
| 15020 | ..........GLLmAKKYKMNLTIVIVN........... | -0.62908 | 3.$620E-04 | lmo1675 (menD) | AKKYKMNLT | 1.150E-12 |
| 15021 | .......TVRAKSKTYPVYInEFALE............. | 0.14445 | 5.5769E-01 | lmo1927 (aroB) | KTYPVYInE | 1.187E-10 |
| 15022 | ..........mNRVmLPLQQmGAKMHGK............ | 0.14475 | 5.5742E-01 | lmo1923 (aroE) | VmLPLQQmG | 2.556E-13 |
| 15023 | ............VMASDYTRGLSIRAIELVFEnL........ | 0.25073 | 2.4351E-01 | lmo1634 | VMASDYTRG | 6.973E-12 |
| 15024 | .......YMEKHSVSRLVGAPP................. | -0.4422 | 1.8422E-02 | lmo2206 (clpB) | VSRLVGAPP | 3.965E-12 |
| 15025 | ........KTASGIVLPDSAKEKPQSGKIVAVGSGRVLD.... | -0.49627 | 6.8168E-03 | lmo2069 (groES) | IVLPDSAKE | 4.253E-11 |
| 15026 | ..........ESVYLSAQKEnPRLFAKIETF.......... | 0.59506 | 8.1895E-04 | lmo1574 (dnaE) | SVYLSAQKE | 2.233E-11 |
| 15027 | ........RDNYLFQLYEATGTPIHPmSPF............ | -0.05049 | 8.7162E-01 | lmo2712 | FQLYEATGT | 5.383E-11 |

[a] Peptide modifications: oxidized Met (m), deamidated-N (n), and acetyl (k or n-term).
[b] Log2 Fold Change Listeria 6 hr versus 10 min.
[c] Cutoff:alpha = 0.00005
[d] Score based on conformation to I-Ab-binding motif. Max = 9.9E$^{-8}$. Cutoff = 9.0E$^{-11}$.

TABLE 2

Listeria epitopes predicted by BOTA

| SEQ ID NO: | BOTA Prediction (Listeria) | gene name | BOTA score | Motif score | Peptidomics Hit |
|---|---|---|---|---|---|
| 15028 | .....ERWNEKYAQAYPNVSAKID... | lmo0202 (hly) (LLO) | 0.557556 | 9.728E-11 | ..........WNEKYAQAYPNVS......... |
| 15029 | ....ETQHYYGLPVADSAIDRGPL... | lmo2558 (ami) | 0.675373 | 6.385E-11 | ...APGQETQHYYGLPVADSAIDR......... |
| 15030 | .....FRYVFDTAKATAASSYPGS... | lmo2185 | 0.760419 | 1.932E-10 | ......ADFRYVFDTAKATAASSYPG....... |
| 15031 | ....DTTVKFTLPTVAPAFENTIKT.. | lmo0135 | 0.532495 | 5.607E-09 | ......AVDDTTVKFTLPTVAPAFENT...... |
| 15032 | ......EKVVATPVSNVSTSSATSS.. | lmo0186 | 0.616773 | 4.923E-10 | ........GTKEKVVATPVSNVSTSSA...... |
| 15033 | .....INQAYTGSTALSDGLNKM.... | lmo2360 | 0.481871 | 7.495E-11 | ..........GGINQAYTGSTALSDGLN........ |
| 15034 | ...GIAVTAFAAPTIASASTVVV.... | lmo0582 (lap) | 0.671301 | 8.274E-09 | .......IAVTAFAAPTIASA............ |
| 15035 | ....AKELVDNAPKALKEGIA...... | lmo0251 (rpll) | 0.744982 | 1.319E-10 | .........EAKELVDNAPKALKEGIA......... |
| 15036 | ...TVRAKSKTYPVYINEFALED.... | lmo1927 (aroB) | 0.650328 | 1.187E-10 | ..........TVRAKSKTYPVYInEFALE........ |
| 15037 | ....YHGPIFLNASLSGVLE....... | lmo0201 (plcA) | 0.544155 | 6.548E-11 | N/A |
| 15038 | .....FGTHNVSSLSSGALNVHA.... | lmo0551 | 0.367349 | 5.869E-11 | N/A |
| 15039 | ...ANGDLYNAETSQYLGRL....... | lmo0682 | 0.389302 | 5.763E-11 | N/A |
| 15040 | ......YELPKLPYTYDALE....... | sod | 0.463634 | 8.126E-11 | N/A |

TABLE 2-continued

Listeria epitopes predicted by BOTA

| SEQ ID NO: | BOTA Prediction (Listeria) | gene name | BOTA score | Motif score | Peptidomics Hit |
|---|---|---|---|---|---|
| 15041 | YIKKYDGDLKLALAAYNAG | lmo0717 | 0.537408 | 1.079E-10 | N/A |
| 15042 | .FLITMAPEFPYLKPGSA | lmo1883 | 0.547697 | 9.833E-11 | N/A |
| 15043 | ......PKSTVSSATSTAQ | lmo0551 | 0.445178 | 1.292E-10 | N/A |
| 15044 | .....YPYVFGGSSPSTS | lmo1104 | 0.517277 | 5.014E-10 | N/A |

Materials and Methods

Immuno-affinity purification of MHCII complexes. Bone marrow was harvested from C57/BL6 (WT), Atg16l1$^{f/f}$×CD11c-Cre (Conway et al., 2013b), and Atg5$^{f/f}$×CD11c-Cre (Conway et al., 2013a) mice. BMDCs were differentiated from bone marrow for seven days in antibiotic-free DMEM supplemented with 20% FBS and GM-CSF (2% conditioned TOPO medium). In parallel, L. monocytogenes strain EGDe (ATCC BA-679) was cultured overnight in BHI medium, washed in PBS, and cocultured with BMDCs at an MOI of approximately 100:1 for 30 minutes. Tissue culture dishes containing cocultures were washed in PBS and cultured for an additional 10 minutes or 6 hours in DC media containing gentamicin (30 µg/ml). BMDCs were then harvested by scraping, washed in PBS, and lysed in 1% NP-40, 4 mM MgCl$_2$, 6 µg/ml DNaseI from bovine pancreas (Sigma Aldrich), and PBS pH 7.4 at 250×10$^6$ cells/4 ml lysis buffer/sample. Clarified lysates were subjected to immunoprecipitation overnight at 4° C. with gentle rotation. Immunoprecipitation was performed with NHS Mag Sepharose (GE Healthcare) covalently coupled to anti-H2-IA (clone Y3P (Janeway et al., 1984)). Each sample contained 130 µl packed beads and approximately 650 µg antibody. Beads were then washed twice in PBS containing 0.1% NP-40 and three times in PBS.

MHC-peptide elution and desalting. Peptides were eluted from MHC complexes and desalted on in-house-built Empore C18 StageTips (3M, 2315) as described previously (Rappsilber et al., 2007). Sample loading, washes, and elution were performed on a tabletop centrifuge at a maximum speed of 2,000-3,500×g. Briefly, StageTips were equilibrated with 2×100 µL washes of methanol, 2×50 µL washes of 50% acetonitrile/0.1% formic acid (FA), and 2×100 µL washes of 1% FA. In a tube, the dried beads from MHC-associated peptide IPs were thawed at 4° C., reconstituted in 50 µL 3% ACN/5% FA, and loaded onto StageTips. The beads were washed with 50 µL 1% FA, and peptides were further eluted using two rounds of 5-minute incubations in 10% acetic acid. The combined wash and elution volumes were combined and loaded onto StageTips. The tubes containing the IP beads were washed again with 50 µL 1% FA, and this volume was also loaded onto StageTips. Peptides were washed twice on the StageTip with 100 µL 1% FA. Peptides were eluted using a step gradient of 20 µL 20% ACN/0.1% FA, 20 µL 40% ACN/0.1% FA, and 20 µL 60% ACN/0.1% FA. Step elutions were combined and dried to completion.

iTRAQ 4-plex labeling for quantitative proteomics. Quantitative proteomics was performed as described previously (Lassen et al., 2014; Mertins et al., 2014). Briefly, each peptide mixture was reconstituted in 20 µL dissolution buffer labeled with 0.5 units (40 µL of 80 µL iTRAQ4 reagent in ethanol) of iTRAQ 4 reagent for 1 hour at room temperature (RT) (~22° C.). Excess reagent was quenched with 5 µL Tris/HCl for 30 minutes at RT. iTRAQ4-plexes were combined, dried to completion, and acidified by adding 1% FA (150 µL). Samples were desalted on in-house built Empore SCX/C18 StageTips (3M, 2315, 2251) as described previously (Rappsilber et al., 2007). Peptides were eluted from the C18/SCX StageTips with two pH cuts (5.5, 11), and the remaining 20% ACN was diluted with 1% FA. Samples were then loaded on in-house built Empore C18 StageTips, desalted, and dried to completion as described above.

MHC-peptide sequencing by tandem mass spectrometry. All nanoLC-ESI-MS/MS analyses employed the same LC separation conditions described below. Samples were chromatographically separated using a Proxeon Easy NanoLC 1000 (Thermo Scientific, San Jose, CA) fitted with a PicoFrit (New Objective, Woburn, MA) 75-µm inner diameter capillary with a 10-µm emitter was packed under pressure to ~20 cm with of C18 Reprosil beads (1.9 µm particle size, 200 Å pore size, Dr. Maisch GmBH) and heated at 50° C. during separation. Samples were reconstituted in 9 µL 3% ACN/5% FA, and 3 µL (~100×10$^6$ cell equivalents) was injected for analysis. Peptides were eluted with a linear gradient from 7-30% of Buffer B (0.1% FA/90% ACN) over 82 min, 30-90% Buffer B over 6 min, and then held at 90% Buffer B for 15 min at 200 nL/min (Buffer A: 0.1% FA/3% ACN) to yield ~11 sec peak widths. During data-dependent acquisition, eluted peptides were introduced into a Q-Exactive HF mass spectrometer (Thermo Scientific) equipped with a nanoelectrospray source (James A. Hill Instrument Services, Arlington, MA) at 2.15 kV. A full-scan MS was acquired at a resolution of 60,000 from 300 to 1,800 m/z (AGC target 16, 20 ms Max IT). Each full scan was followed by top 15 data-dependent MS2 scans at resolution 15,000, using an isolation width of 1.7 m/z with a 0.3 m/z offset, a fixed first mass at 100 m/z, a collision energy of 29, an ACG Target of 5e4, and a max fill time of 100 ms max injection time. An isolation offset of 0.3 m/z was used so that doubly charged precursor isotope distributions would be centered in the isolation window. Some MHC-associated peptides tend to be short (<15 amino acids) so the monoisotopic peak is nearly always the tallest peak in the isotope cluster and the mass spectrometer acquisition software places the tallest isotopic peak in the center of the isolation window in the absence of a specified offset. Dynamic exclusion was enabled with a repeat count of 1 and an exclusion duration of 10 sec. Charge state screening was enabled along with monoisotopic precursor selection using Peptide Match Preferred to prevent triggering of MS/MS on precursor ions with charge state 1, >6, or unassigned.

Interpretation of MS/MS data. Mass spectra were interpreted using the Spectrum Mill software package v5.1 pre-Release (Agilent Technologies). MS/MS spectra were excluded from searching if they did not have a precursor MH+ in the range of 600-4000, had a precursor charge >5, or had a minimum of <5 detected peaks. Merging of similar spectra with the same precursor m/z acquired in the same chromatographic peak was disabled. High resolution MS/MS spectra were searched against a UniProt database containing reference proteome sequences (including isoforms and excluding fragments) from human mouse (41,157 entries) with a set of common laboratory contaminant proteins (150 sequences) to yield a total of 41,307 redundant sequences. The sequences were downloaded from the UniProt website in April 2013.

Prior to both search rounds all MS/MS had to pass the spectral quality filter with a sequence tag length >3, i.e., minimum of 4 masses separated by the in-chain mass of an amino acid. In the first round search, all spectra were searched using a no-enzyme specificity, fixed modification of cysteine as unmodified, fixed modification of partial iTRAQ labeling, the following variable modifications (oxidized methionine, deamidation, acetyl-N-term), a precursor mass tolerance of ±10 ppm, product mass tolerance of ±20 ppm, and a minimum matched peak intensity of 50%. Peptide spectrum matches (PSMs) for individual spectra were automatically designated as confidently assigned using the Spectrum Mill autovalidation module to apply target-decoy based FDR estimation at the PSM level to set scoring threshold criteria. Peptide autovalidation was performed with an auto thresholds strategy using a minimum sequence length of 7, automatic variable range precursor mass filtering, and score and delta Rank1-Rank2 score thresholds optimized across all LC-MS/MS runs. This yielded a PSM level FDR estimate for precursor charges 1 thru 7 of <1.0% for each precursor charge state. In the second round search, all remaining spectra that were not confidently identified in the first round were searched using the above parameters against a RefSeq database containing *L. monocytogenes* EGD-e reference protein sequences (2,867) downloaded in December 2014. An additional round of FDR thresholding as described above was applied to PSMs from the second round search to estimate FDR by species (mouse vs. *L. monocytogenes* EGD-e). The combined PSMs from each round had a peptide level FDR<2.0%. Only *L. monocytogenes* EGD-e peptides that did not overlap with human peptides were reported.

*Listeria* infection and ELISPOT. *L. monocytogenes* strain EGDe (ATCC BA-679) was grown to log phase in BHI, washed in PBS, and used to inoculate mice by i.p. injection with a dose of $1\times10^4$ CFU/200 µl/mouse. Seven days after infection, spleens were harvested, red blood cells were lysed, and single cell suspensions were replated at $2.5\times10^5$/200 µl/well on 96-well ELISPOT plates (Millipore MAIPS4510) precoated with anti-IFNγ (BD Pharmingen 551881) at a concentration of 5 µg/ml in PBS. Peptides were added at a concentration of 100 nM to restimulate splenocytes overnight. After stimulation, plates were washed, blocked, and incubated with biotinylated anti-IFNγ (BD Pharmingen 551881) at a concentration of 2 µg/ml and streptavidin-AKP (BD Pharmingen 554065) at a dilution of 1:1000. After 60 minutes, plates were washed and developed with 3-amino-9-ethylcarbazole (AEC, Sigma-Aldrich, A6926). IFNγ-secreting cells were scanned and enumerated using an Immunospot Analyzer ELISpot reader (CTL). All samples were run in triplicate. The following peptides were synthesized by New England Peptide: lmo2185_293-312 ADFRYVFDTAKATAASSYPG (SEQ ID NO: 14986), lmo0202_189-204 WNEKYAQAYPNVSAKI (SEQ ID NO: 14981), lmo0135_150-169 VDDTTVKFTLPTVAPAFENT (SEQ ID NO: 14997), lmo2558_533-553 APGQETQHYYGLPVADSAIDR (SEQ ID NO: 14984), lmo2360_289-306 GGINQAYTGSTALSDGLN (SEQ ID NO: 15009), lmo0186_285-303 GTKEKVVATPVSNVSTSSA (SEQ ID NO: 15005), lmo0582a_26-46 STVVVEAGDTLWGIAQSKGTT (SEQ ID NO: 15012), lmo0582b_12-25 IAVTAFAAPTIASA (SEQ ID NO: 15013). To calculate the frequency of CD4+ cells in each splenocyte sample from infected mice, an aliquot of cells from each mouse was stained for flow cytometric analysis. $1\times10^6$ cells were incubated with 2.4G2 Mouse Fc block in PBS/FBS (BD Pharmingen, 553142) for 20 min at 4° C. Cells were then washed and stained with FITC-conjugated anti-mouse CD4 (Biolegend, 100510) for 20 min at 4° C. Fluorescently labeled cells were acquired on the FACSVerse flow cytometer (BD Biosciences) and analyzed using FlowJo Analysis Software (Tree Star).

BOTA algorithm architecture. BOTA starts with an input genome and the associated genome annotation. The genome annotation may be in GFF3 format. It first extracts the amino acid sequences of the protein-coding genes and then performs the following analysis: (i) domain identification using hmmscan of HMMER3.1b2 (Eddy, 2011) against (Finn et al., 2016); (ii) cellular localization prediction using PSORTb v3.0.2 (Yu et al., 2010) with default settings; and (iii) transmembrane topology prediction by HMMTOP (Tusnady and Simon, 1998). This information is then integrated to generate a list of candidate peptides following three criteria: (i) the protein should be located in the outer membrane, cell wall (if applicable), or extracellular space; (ii) if located in the outer membrane or cell wall, only the outfacing part of the protein will be considered; and (iii) the peptide should present sufficient accessibility as decided by three rules: (iii-a) it cannot be fewer than eight amino acids away from anchoring domain in the cell wall or outer membrane; (iii-b) it cannot be located in domains shorter than 30 amino acids due to the fact that small domains are usually tightly folded; and (iii-c) it cannot be flanked by two domains that are fewer than 20 amino acids apart. These candidate peptides are then scored by the deep neural network as described below. For each peptide classified as a candidate epitope, BOTA further validates it with the motif score as defined previously, and a randomized score. For the motif score validation, it calculates all the 9-mers within the peptide and requires the maximum to be larger than $5\times10^{-11}$; for the randomized score, BOTA shuffles the amino acids in the 9-mer and calculates the motif score for each of the randomized 9-mers. The original 9-mer's motif score requires a rank in the top 30% of all randomized 9-mers.

In certain example embodiments, protein intracellular prediction may be achieved by using a lowest common ancestor (LCA) database to train a convolutional neural network (CNN) model, a generative adversarial network (GAN) models, or both. In other example embodiments, multiple transmembranal databases may be used to train a domain prediction model for use in conjunction with, or as an alternative to HMMTOP.

Deep neural network for MHCII binder prediction. Applicants employed a deep neural network scheme to develop an MHCII-binder predictor. In brief, Applicants first encoded every amino acid into a p-dimensional binary vector b, with half of its elements being 1 and the rest being 0, chosen at random. Therefore, given a peptide with length l longer than k, it is first converted to an l×b descriptor matrix S, in which $S_{ij}=1$ if the i-th amino acid's 1-valued indices overlap with j, otherwise $S_{ij}=0$. The matrix S is then normalized by row sum to become S' such that $$S_{ij}' = S_{ij}/\Sigma_{j=1}^{b} S_{ij}$$

S' is then convoluted into an (l−k+1)×d matrix X, where d is the number of pre-trained motif network models within the overall model and k is the length of such binding cores. $X_{ij}$ represents the score of motif network model j aligned to position i. The cohort of motif network models are arranged in a d×k×b array H with $H_{ijk}$ being the d-th motif network model aligned to the k-th position of the b-th set of amino acids (FIG. 8D). This sequence conversion and convolution setup is similar to model developed by Alipanahi et al (Alipanahi et al., 2015).

With the convoluted matrix X, Applicants filter it with a max-rectified linear unit (ReLU) layer, and the rectified matrix Y is then fed into a max pooling stage to be transformed into d-dimensional vector Z, in which $$z_j = \max(Y_{1j}, Y_{2j}, \ldots, Y_{nj})$$

This d-dimensional vector Z is then used as input for a neural network with Maxout dropout model. Z is then used as the input for a standard output layer for final prediction calculation.

The goal is to minimize the prediction error as measured by 1-norm distance of all the peptides. Back propagation with a stochastic gradient descent method using mini batch size at 64 was used to reach optimal weights. To train the weights, the mouse epitope peptides were used as training set true positive; Applicants also added in silico true negative peptides by surveying an equal number of the peptides that are not part of the peptidomics data readout at random. Applicants first randomly constructed 100 replicates of 3-fold cross validation datasets using the epitopes and the in silico true negative sequences. For each replicate, BOTA's initial state weights were assigned randomly and then trained until performance plateaued (<0.1% improvement in ten iterations). The validation's average AUC was used as a measure of model fitness; and the one with the highest average AUC among the 100 replicates was chosen to generate the final optimal parameters by using all mouse peptides (FIG. 9C). Then the optimal model constructed from the previous step were used to predict the unique *Listeria* peptides, and netMHCIIpan was used to predict the affinity of the same set of peptides with default settings.

TCRseq and 5' digital gene expression (DGE). 5'DGE RNA-seq data were analyzed using an in-house data analysis pipeline. Reads were aligned to the mm10 genome using bwa (Li et al., 2009). The downstream analysis was carried out using the Seurat package (www.satijalab.org/seurat). The dataset was filtered to remove genes that were expressed in less than 10% of the data or cells that expressed transcripts that mapped to fewer than 500 unique genes. Further, to remove doublet cells, cells that displayed more heterogeneity than the $90^{th}$ quantile (1846 unique genes) were filtered out. Highly variable, highly expressed genes (log $(\sigma/\mu)>0.75$ and log $(\mu)>1.5$) were identified from a mean-variance dispersion analysis. These genes were then used for clustering the single cells using the SNN-Cliq algorithm, which maps the cells onto a k-nearest neighbor graph and then finds "cliques" of cells expressing similar genes (McDavid et al., 2014; Xu and Su, 2015). It was found that cells expressing Ifng and Tbx21 belonged primarily to cluster 0. Cluster identities of Th17 single cells were overlaid on a t-SNE plots. The cells were clustered on the basis of highly expressed, highly varying genes, using a graph-based method, SNN-Cliq (McDavid et al., 2014). Violin/Feature plot: Ifng is identified as a marker gene for cluster 0 based on the bimod test for differential expression (Xu et al., 2015).

TCR Screening. TCR-negative BW5147 cells were obtained from ATCC. The stable sub-line BW_4-28 was produced by introduction of murine CD4 and CD28 by lentiviral transduction. The Orf encoding CD4-P2A-CD28 was synthesized (IDT) and cloned in place of spCas9-P2A-BlastR into pXPR_BRD101 (Genetic Perturbation Platform, Broad Institute) by Gibson assembly. The stable sub-line BW_B7/4 was produced by introduction of chimeric murine CD86 cytoplasmic domain fused in-frame with CD4 transmembrane and cytoplasmic domains by lentiviral transduction. The Orf encoding CD86/CD4 was synthesized (IDT) and cloned in place of spCas9-P2A-BlastR into pXPR_BRD101 (Genetic Perturbation Platform, Broad Institute) by Gibson assembly.

scTCRz_v3 vector was derived from pLX_TRC307 (Genetic Perturbation Platform, Broad Institute) by replacing the stuffer sequence with the following codon-optimized Orf: mTrbc1-hCD3zeta (transmembrane and cytoplasmic domains)-P2A-hIgKleader-mTrac hCD3zeta (transmembrane and cytoplasmic domains). Single-chain TCRs were synthesized as gBlocks (IDT) comprising Trav-Traj-linker (3×G$_4$SGGGG)-Trbv-Trbj and cloned by Gibson assembly into NheI and BsrGI sites upstream of Trbc1 in scTCRz_v3 vector. MHCIIz_v2 vector was derived from pLX_TRC307 (Genetic Perturbation Platform, Broad Institute) by replacing the stuffer sequence with the following sequence: H2Ab1leader-XmaI-linker (3×G$_4$S)-H2Ab1 (extracellular and transmembrane domains)-hCD3zeta (cytoplasmic domain)-P2A H2Aa (extracellular and transmembrane domains)-hCD3zeta (cytoplasmic domain). Peptide epitope-encoding sequences were synthesized as ultramers (IDT) and cloned by Gibson assembly into the XmaI site in the MHCIIz_v2 vector. pMHCII and scTCRs were introduced into BW_B7/4 and BW_4-28 cells, respectively, by lentiviral transduction and maintained under puromycin selection (3 ug/ml). To define antigen specificity of TCRs, BW_4-28 cells expressing scTCRs were cocultured with HEK 293T cells transfected with pMHCII and CD86/CD4 or BW_B7/4 cells expressing pMHCII. Cells were combined at a 1:1 ratio in 96-well flat-bottom plates (total 100,000 cells/well). Culture supernatants were harvested after 18 hours, and IL-2 was measured by cytokine bead array (BD Pharmingen) or cells were harvested after 18 hours, and mRNA expression of the activation marker Nur77 (Nr4a1) was quantified relative to Actb.

Animals. Mice were bred in specific-pathogen-free facilities at Massachusetts General Hospital (Boston, MA) prior to infection and transferred to biosafety level 2 (BL2) housing upon *L. monocytogenes* infection. All animal studies were conducted in compliance with ethical regulations and were approved by the Institutional Care and Use Committee (IACUC) at Massachusetts General Hospital. Atg5$^{f/f}$ and Atg16l1$^{f/f}$ mice were generated as previously described (Conway et al., 2013b; Hara et al., 2006) and bred with mice expressing Cre recombinase under the control of the CD11c promoter (CD11c-Cre) (Jackson Laboratories). All mice were maintained on food and water ad libitum, used between 8-12 weeks of age, and age- and sex-matched for each experiment.

Statistical analysis. For data analysis, iTRAQ 4 ratios for the two biological replicates were filtered to retain only those deemed reproducible as described previously (Kronke et al., 2015). Reproducibility was based on replicates being confined within the 95% limits of agreement of a Bland-Altman plot (Bland and Altman, 1986). Reproducible replicates were then subjected to a moderated t-test to assess statistical significance (Smyth, 2004). To generate the I-A$^b$-binding motif, all mouse peptides were aligned by MultAlin (Corpet, 1988) and visualized with WebLogo (Crooks et al., 2004). The frequencies of each amino acid at each position of the 9-mer core were used to generate a position-weight matrix. I-A$^b$ binding scores for *Listeria* peptides were produced from this matrix and represented as the product of amino acid frequencies for each position of the 9-mer core (Table 1). Epitope mapping and protein domain overlay were performed with NCBI's Conserved Domain Database (Marchler-Bauer et al., 2015). Subcellular localization of antigenic *Listeria* proteins was predicted by PSORTb v3.0.2 (Yu et al., 2010), and by COMPARTMENTS (Binder et al., 2014) for mouse proteins. Transmembrane topology was predicted with HMMTOP (Tusnady and Simon, 1998).

REFERENCES

Alipanahi, B., Delong, A., Weirauch, M. T., and Frey, B. J. (2015). Predicting the sequence specificities of DNA- and RNA-binding proteins by deep learning. Nat Biotechnol 33, 831-838.

Anders, S., Pyl, P. T., and Huber, W. (2015). HTSeq$^{-/-}$ a Python framework to work with high-throughput sequencing data. Bioinformatics 31, 166-169.

Andreatta, M., Schafer-Nielsen, C., Lund, O., Buus, S., and Nielsen, M. (2011). NNAlign: a web-based prediction method allowing non-expert end-user discovery of sequence motifs in quantitative peptide data. PLOS ONE 6, e26781.

Arunachalam, B., Phan, U. T., Geuze, H. J., and Cresswell, P. (2000). Enzymatic reduction of disulfide bonds in lysosomes: characterization of a gamma-interferon-inducible lysosomal thiol reductase (GILT). Proc Natl Acad Sci USA 97, 745-750.

Babbitt, B. P., Allen, P. M., Matsueda, G., Haber, E., and Unanue, E. R. (1985). Binding of immunogenic peptides to Ia histocompatibility molecules. Nature 317, 359-361.

Binder, J. X., Pletscher-Frankild, S., Tsafou, K., Stolte, C., O'Donoghue, S. I., Schneider, R., and Jensen, L. J. (2014). COMPARTMENTS: unification and visualization of protein subcellular localization evidence. Database (Oxford) 2014, bau012.

Bland, J. M., and Altman, D. G. (1986). Statistical methods for assessing agreement between two methods of clinical measurement. Lancet 1, 307-310.

Chatterjee, S. S., Hossain, H., Otten, S., Kuenne, C., Kuchmina, K., Machata, S., Domann, E., Chakraborty, T., and Hain, T. (2006). Intracellular gene expression profile of *Listeria monocytogenes*. Infect Immun 74, 1323-1338.

Chicz, R. M., Urban, R. G., Gorga, J. C., Vignali, D. A., Lane, W. S., and Strominger, J. L. (1993). Specificity and promiscuity among naturally processed peptides bound to HLA-DR alleles. J Exp Med 178, 27-47.

Chicz, R. M., Urban, R. G., Lane, W. S., Gorga, J. C., Stern, L. J., Vignali, D. A., and Strominger, J. L. (1992). Predominant naturally processed peptides bound to HLA-DR1 are derived from MHC-related molecules and are heterogeneous in size. Nature 358, 764-768.

Christmann, B. S., et al. Human seroreactivity to gut microbiota antigens. J. Allergy Clin. Immunol. 136, 1378-1386 e1371-1375 (2015).

Conway, K. L., Kuballa, P., Song, J. H., Patel, K. K., Castoreno, A. B., Yilmaz, O. H., Jijon, H. B., Zhang, M., Aldrich, L. N., Villablanca, E. J., et al. (2013a). Atg16l1 is required for autophagy in intestinal epithelial cells and protection of mice from *Salmonella* infection. Gastroenterology 145, 1347-1357.

Conway, K. L., Kuballa, P., Khor, B., Zhang, M., Shi, H. N., Virgin, H. W., and Xavier, R. J. (2013b). ATG5 regulates plasma cell differentiation. Autophagy 9, 528-537.

Corpet, F. (1988). Multiple sequence alignment with hierarchical clustering. Nucleic Acids Res 16, 10881-10890.

Cresswell, P., Arunachalam, B., Bangia, N., Dick, T., Diedrich, G., Hughes, E., and Maric, M. (1999). Thiol oxidation and reduction in MHC-restricted antigen processing and presentation. Immunol Res 19, 191-200.

Crooks, G. E., Hon, G., Chandonia, J. M., and Brenner, S. E. (2004). WebLogo: a sequence logo generator. Genome Res 14, 1188-1190.

Depontieu, F. R., Qian, J., Zarling, A. L., McMiller, T. L., Salay, T. M., Norris, A., English, A. M., Shabanowitz, J., Engelhard, V. H., Hunt, D. F., et al. (2009). Identification of tumor-associated, MHC class II-restricted phosphopeptides as targets for immunotherapy. Proc Natl Acad Sci USA 106, 12073-12078.

Dongre, A. R., et al. In vivo MHC class II presentation of cytosolic proteins revealed by rapid automated tandem mass spectrometry and functional analyses. Eur. J. Immunol. 31, 1485-1494 (2001).

Eddy, S. R. (2011). Accelerated Profile HMM Searches. PLOS Comput Biol 7, e1002195.

Finn, R. D., Coggill, P., Eberhardt, R. Y., Eddy, S. R., Mistry, J., Mitchell, A. L., Potter, S. C., Punta, M., Qureshi, M., Sangrador-Vegas, A., et al. (2016). The Pfam protein families database: towards a more sustainable future. Nucleic Acids Res 44, D279-285.

Hall, A. B., Tolonen, A. C. & Xavier, R. J. Human genetic variation and the gut microbiome in disease. Nat. Rev. Genet. 18, 690-699 (2017).

Hara, T., Nakamura, K., Matsui, M., Yamamoto, A., Nakahara, Y., Suzuki-Migishima, R., Yokoyama, M., Mishima, K., Saito, I., Okano, H., et al. (2006). Suppression of basal autophagy in neural cells causes neurodegenerative disease in mice. Nature 441, 885-889.

Heng, T. S., Painter, M. W. & Immunological Genome Project, C. The Immunological Genome Project: networks of gene expression in immune cells. Nat. Immunol. 9, 1091-1094 (2008).

Hsieh, C. S., deRoos, P., Honey, K., Beers, C., and Rudensky, A. Y. (2002). A role for cathepsin L and cathepsin S in peptide generation for MHC class II presentation. J Immunol 168, 2618-2625.

Hsing, L. C., and Rudensky, A. Y. (2005). The lysosomal cysteine proteases in MHC class II antigen presentation. Immunol Rev 207, 229-241.

Hunt, D. F., Michel, H., Dickinson, T. A., Shabanowitz, J., Cox, A. L., Sakaguchi, K., Appella, E., Grey, H. M., and Sette, A. (1992). Peptides presented to the immune system by the murine class II major histocompatibility complex molecule I-Ad. Science 256, 1817-1820.

Janeway, C. A., Jr., Conrad, P. J., Lerner, E. A., Babich, J., Wettstein, P., and Murphy, D. B. (1984). Monoclonal antibodies specific for Ia glycoproteins raised by immunization with activated T cells: possible role of T cell-bound Ia antigens as targets of immunoregulatory T cells. J Immunol 132, 662-667.

Kim, A., and Sadegh-Nasseri, S. (2015). Determinants of immunodominance for CD4 T cells. Curr Opin Immunol 34, 9-15.

Kim, D., Pertea, G., Trapnell, C., Pimentel, H., Kelley, R., and Salzberg, S. L. (2013). TopHat2: accurate alignment of transcriptomes in the presence of insertions, deletions and gene fusions. Genome Biol 14, R36.

Kronke, J., Fink, E. C., Hollenbach, P. W., MacBeth, K. J., Hurst, S. N., Udeshi, N. D., Chamberlain, P. P., Mani, D. R., Man, H. W., Gandhi, A. K., et al. (2015). Lenalidomide induces ubiquitination and degradation of CK1alpha in del(5q) MDS. Nature 523, 183-188.

Lassen, K. G., Kuballa, P., Conway, K. L., Patel, K. K., Becker, C. E., Peloquin, J. M., Villablanca, E. J., Norman, J. M., Liu, T. C., Heath, R. J., et al. (2014). Atg16L1 T300A variant decreases selective autophagy resulting in altered cytokine signaling and decreased antibacterial defense. Proc Natl Acad Sci USA 111, 7741-7746.

Li, H. & Durbin, R. Fast and accurate short read alignment with Burrows-Wheeler transform. Bioinformatics 25, 1754-1760 (2009).

Lippolis, J. D., White, F. M., Marto, J. A., Luckey, C. J., Bullock, T. N., Shabanowitz, J., Hunt, D. F., and Engelhard, V. H. (2002). Analysis of MHC class II antigen processing by quantitation of peptides that constitute nested sets. J Immunol 169, 5089-5097.

Liu, X., et al. Alternate interactions define the binding of peptides to the MHC molecule IA(b). Proc. Natl. Acad. Sci. U.S.A. 99, 8820-8825 (2002).

Marchler-Bauer, A., Derbyshire, M. K., Gonzales, N. R., Lu, S., Chitsaz, F., Geer, L. Y., Geer, R. C., He, J., Gwadz, M., Hurwitz, D. I., et al. (2015). CDD: NCBI's conserved domain database. Nucleic Acids Res 43, D222-226.

McDavid, A., et al. Modeling bi-modality improves characterization of cell cycle on gene expression in single cells. PLOS Comput. Biol. 10, e1003696 (2014).

Mertins, P., Yang, F., Liu, T., Mani, D. R., Petyuk, V. A., Gillette, M. A., Clauser, K. R., Qiao, J. W., Gritsenko, M. A., Moore, R. J., et al. (2014). Ischemia in tumors induces early and sustained phosphorylation changes in stress kinase pathways but does not affect global protein levels. Mol Cell Proteomics 13, 1690-1704.

Miyazaki, T., Wolf, P., Tourne, S., Waltzinger, C., Dierich, A., Barois, N., Ploegh, H., Benoist, C., and Mathis, D. (1996). Mice lacking H2-M complexes, enigmatic elements of the MHC class II peptide-loading pathway. Cell 84, 531-541.

Mommen, G. P., Marino, F., Meiring, H. D., Poelen, M. C., van Gaans-van den Brink, J. A., Mohammed, S., Heck, A. J., and van Els, C. A. (2016). Sampling From the Proteome to the Human Leukocyte Antigen-DR (HLA-DR) Ligandome Proceeds Via High Specificity. Mol Cell Proteomics 15, 1412-1423.

Nelson, C. A., Roof, R. W., McCourt, D. W., and Unanue, E. R. (1992). Identification of the naturally processed form of hen egg white lysozyme bound to the murine major histocompatibility complex class II molecule I-Ak. Proc Natl Acad Sci USA 89, 7380-7383.

Ormerod, K. L., et al. Genomic characterization of the 1 uncultured Bacteroidales family S24-7 inhabiting the guts of homeothermic animals. Microbiome 4, 36 (2016).

Palm, N. W., de Zoete, M. R. & Flavell, R. A. Immune-microbiota interactions in health and disease. Clin. Immunol. 159, 122-127 (2015).

Rappsilber, J., Mann, M., and Ishihama, Y. (2007). Protocol for micro-purification, enrichment, pre-fractionation and storage of peptides for proteomics using StageTips. Nat Protoc 2, 1896-1906.

Robinson, M. D., McCarthy, D. J., and Smyth, G. K. (2010). edgeR: a Bioconductor package for differential expression analysis of digital gene expression data. Bioinformatics 26, 139-140.

Rudensky, A., Preston-Hurlburt, P., Hong, S. C., Barlow, A., and Janeway, C. A., Jr. (1991). Sequence analysis of peptides bound to MHC class II molecules. Nature 353, 622-627.

Scallan, E., Hoekstra, R. M., Angulo, F. J., Tauxe, R. V., Widdowson, M. A., Roy, S. L., Jones, J. L., and Griffin, P. M. (2011). Foodborne illness acquired in the United States—major pathogens. Emerg Infect Dis 17, 7-15.

Schindelin, J., Arganda-Carreras, I., Frise, E., Kaynig, V., Longair, M., Pietzsch, T., Preibisch, S., Rueden, C., Saalfeld, S., Schmid, B., et al. (2012). Fiji: an open-source platform for biological-image analysis. Nat Methods 9, 676-682.

Schulze, M. S., and Wucherpfennig, K. W. (2012). The mechanism of HLA-DM induced peptide exchange in the MHC class II antigen presentation pathway. Curr Opin Immunol 24, 105-111.

Seamons, A., Sutton, J., Bai, D., Baird, E., Bonn, N., Kafsack, B. F., Shabanowitz, J., Hunt, D. F., Beeson, C., and Goverman, J. (2003). Competition between two MHC binding registers in a single peptide processed from myelin basic protein influences tolerance and susceptibility to autoimmunity. J Exp Med 197, 1391-1397.

Sette, A., Ceman, S., Kubo, R. T., Sakaguchi, K., Appella, E., Hunt, D. F., Davis, T. A., Michel, H., Shabanowitz, J., Rudersdorf, R., et al. (1992). Invariant chain peptides in most HLA-DR molecules of an antigen-processing mutant. Science 258, 1801-1804.

Smyth, G. K. (2004). Linear models and empirical bayes methods for assessing differential expression in microarray experiments. Stat Appl Genet Mol Biol 3, Article3.

Sofron, A., Ritz, D., Neri, D., and Fugmann, T. (2016). High-resolution analysis of the murine MHC class II immunopeptidome. Eur J Immunol 46, 319-328.

Stern, L. J., Brown, J. H., Jardetzky, T. S., Gorga, J. C., Urban, R. G., Strominger, J. L., and Wiley, D. C. (1994). Crystal structure of the human class II MHC protein HLA-DR1 complexed with an influenza virus peptide. Nature 368, 215-221.

Stoll, M. L., et al. Altered microbiota associated with abnormal humoral immune responses to commensal organisms in enthesitis-related arthritis. Arthritis Res. Ther. 16, 486 (2014).

Suri, A., Walters, J. J., Rohrs, H. W., Gross, M. L., and Unanue, E. R. (2008). First signature of islet beta-cell-derived naturally processed peptides selected by diabetogenic class II MHC molecules. J Immunol 180, 3849-3856.

Tusnady, G. E., and Simon, I. (1998). Principles governing amino acid composition of integral membrane proteins: application to topology prediction. J Mol Biol 283, 489-506.

Wang, P., Sidney, J., Dow, C., Mothe, B., Sette, A., and Peters, B. (2008). A systematic assessment of MHC class II peptide binding predictions and evaluation of a consensus approach. PLOS Comput Biol 4, e1000048.

Weber, K. S., et al. Distinct CD4+ helper T cells involved in primary and secondary responses to infection. Proc. Natl. Acad. Sci. U.S.A. 109, 9511-9516 (2012).

Xu, C. & Su, Z. Identification of cell types from single-cell transcriptomes using a novel clustering method. Bioinformatics 31, 1974-1980 (2015).

Yu, N. Y., Wagner, J. R., Laird, M. R., Melli, G., Rey, S., Lo, R., Dao, P., Sahinalp, S. C., Ester, M., Foster, L. J., et al. (2010). PSORTb 3.0: improved protein subcellular localization prediction with refined localization subcategories and predictive capabilities for all prokaryotes. Bioinformatics 26, 1608-1615.

Zeng, M. Y., et al. Gut Microbiota-Induced Immunoglobulin G Controls Systemic Infection by Symbiotic Bacteria and Pathogens. Immunity 44, 647-658 (2016).

Zhu, Y., Rudensky, A. Y., Corper, A. L., Teyton, L. & Wilson, I. A. Crystal structure of MHC class II I-Ab in complex with a human CLIP peptide: prediction of an I-Ab peptide-binding motif. J. Mol. Biol. 326, 1157-1174 (2003).

The invention is further described by the following numbered paragraphs:

1. A method for identifying MHCII antigenic epitopes comprising:
   generating, by a processor, a set of candidate antigens from one or more input genome sequences; and
   generating, by the processor, a ranked set of antigenic epitopes from the candidate antigens using a deep neural network, wherein the deep neural network is trained using a set of MHCII-presented peptides isolated from antigen presenting cells.
2. The method of paragraph 1, wherein the antigen presenting cells are dendritic cells.
3. The method of paragraph 1, wherein generating a set of candidate antigens from one or more input genome sequences comprises:
   predicting, by the processor, genes from an input genome sequence; and
   defining, by the processor, a set of candidate antigens from the set of predicted genes based on one or more of protein cellular location, transmembrane structure, and domain distribution.
4. The method of paragraph 3, wherein defining, by the processor, a set of candidate antigens from the set of predicted genes, comprises:
   a) selecting surface and secreted proteins;
   b) masking intracellular regions and transmembrane domains of the surface and extracellular proteins;
   c) excluding regions that are within domains of less than 30 amino acids;
   d) excluding regions between a series of inaccessible domains; and
   e) excluding inter-domain regions between a series of adjacent domains wherein the inter-domain regions are less than or equal to 20 amino acids.
5. The method of paragraph 4, further comprising masking up to 20 amino acids flanking the intracellular regions and transmembrane domains.
6. The method of paragraph 4, wherein 8 amino acids flanking the intracellular regions and transmembrane domains are masked.
7. The method of paragraph 4, wherein the surface protein is a cell wall protein.
8. The method of paragraph 4, wherein the surface protein is an outer membrane protein.
9. The method of any of paragraphs 1 to 8, wherein the antigenic epitopes are derived from candidate antigens more than 20 amino acids away from a transmembrane domain.
10. The method of any of paragraphs 1 to 9, wherein the candidate antigens comprise a tertiary structure required for proteolytic enzyme accessibility.
11. The method of any of paragraphs 1 to 10, wherein the candidate antigens comprise a defined MHCII-binding motif in the primary amino acid sequence of the predicted genes.
12. The method of paragraph 11, wherein the defined MHCII-binding motif is the I-A$^b$-binding motif.
13. The method of any of paragraphs 1 to 12, wherein the antigenic epitopes comprise a tertiary structure required for accessibility to a MHCII binding groove.
14. The method of any of paragraphs 1 to 13, wherein generating, by the processor, a ranked set of antigenic epitopes from the candidate antigens using a deep neural network comprises:
   a) encoding each amino acid of an input candidate antigen into a p-dimensional binary vector;
   b) converting the binary vector to a descriptor matrix S;
   c) convoluting the descriptor matrix S to a scoring matrix X; and
   d) transforming the scoring matrix X into a d-dimensional vector Z, wherein vector Z is input for a neural network.
15. The method of any of paragraphs 1 to 14, wherein the method further comprises:
   isolating MHCII-peptide complexes from antigen presenting cells;
   isolating the peptides from the MHCII-peptide complexes;
   sequencing the isolated peptides; and
   training the deep neural network using the set of isolated peptides.
16. The method of paragraph 15, wherein the antigen presenting cells are exposed to a target cell type or target pathogen.
17. The method of paragraph 15 or 16, wherein the antigen presenting cells are dendritic cells.
18. The method of any of paragraphs 1 to 17, wherein the input genome sequence is derived from a target cell type or target pathogen.
19. The method of paragraph 18, wherein the candidate antigens are expressed in the target cell type or target pathogen.
20. The method of any of paragraph 16 to 19, wherein the target cell type or target pathogen is selected from the group consisting of a bacterium, a virus, a protozoa, an allergen and a diseased cell.
21. The method of paragraph 20, wherein the diseased cell is a cancer cell.
22. The method of paragraph 21, wherein the cancer cell is obtained from a subject.
23. The method of paragraph 22, further comprising identifying non-silent tumor specific somatic mutations from the subject specific cancer cell, wherein the ranked set of antigenic epitopes are generated from said mutations.
24. The method of paragraph 20, wherein the diseased cell is associated with an autoimmune disease.
25. The method of paragraph 20, wherein the target pathogen comprises a bacteria belonging to a family selected from the group consisting of *Bacillus, Bartonella, Bordetella, Borrelia, Brucella, Campylobacter, Chlamydia* and *Chlamydophila, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Ureaplasma, Vibrio,* and *Yersinia.*

26. The method of any of paragraphs 1 to 25, wherein the antigen presenting cell comprises a subject specific MHCII allele.
27. The method of any of paragraphs 1 to 26, wherein the antigen presenting cell comprises a human MHCII allele.
28. The method of any of paragraphs 1 to 27, wherein the one or more input genome sequences is obtained by whole genome or whole exome sequencing.
29. The method of any of paragraphs 1 to 20, further comprising detecting whether one or more the antigenic epitopes is present in a sample from a subject suffering from an infection, autoimmune disease, allergy, or cancer.
30. The method of any one of paragraphs 1 to 29, wherein the antigenic epitopes are about 9 to 20 amino acids in length.
31. The method of any of paragraphs 1 to 30, wherein the deep neural network is trained using a set of MHCII-presented peptides comprising one or more of SEQ ID NOs: 1-14979.
32. The method of any of paragraphs 1 to 31, wherein the deep neural network is trained using a set of MHCII-presented peptides comprising one or more of SEQ ID NOs: 14980-15027.
33. The method of any of paragraphs 1 to 32, further comprising preparing a vaccine composition comprising one or more antigenic epitopes from the set of antigenic epitopes generated by the processor.
34. The method of paragraph 33, wherein the vaccine composition is directed to a bacterium, a virus or a protozoa.
35. The method of paragraph 33, wherein the vaccine composition is directed to a cancer.
36. The method of paragraph 33, wherein the vaccine composition is directed to an autoimmune disease, whereby administration of the vaccine induces tolerance to the antigenic epitope.
37. The method of paragraph 34, wherein the vaccine composition is directed to *Listeria*.
38. The method of paragraph 37, wherein the vaccine composition comprises one or more *Listeria* peptides selected from the peptides listed in Table 1.
39. The method of paragraph 38, wherein the one or more *Listeria* peptides are derived from lmo0202, lmo2558, lmo2185, or lmo0135.
40. The method of paragraph 39, wherein the one or more *Listeria* peptides are selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT).
41. The method of any of paragraphs 33 to 40, wherein the vaccine comprises autologous dendritic cells or antigen presenting cells pulsed with the one or more peptides.
42. A method of identifying immunodominant epitopes comprising:
   a) expressing in a first population of immune cells a peptide MHCII library comprising antigenic epitopes identified according to the method of any of paragraphs 1 to 32, wherein the first population of immune cells comprise a detectable reporter gene;
   b) expressing in a second population of CD4+ immune cells a TCRab library expressing TCRab pairs identified in a subject suffering from an infectious disease, autoimmunity, cancer or allergy;
   c) incubating the first population of immune cells with the second population of immune cells;
   d) sorting immune cells positive for the detectable reporter gene; and
   e) identifying peptides bound to MHCII in immune cells positive for the detectable reporter gene.
43. The method of paragraph 42, wherein the TCRab pairs are identified by single cell profiling.
44. The method of paragraphs 43, wherein TCRab pairs are determined by targeted single cell RNA-seq (TCRseq).
45. The method of paragraphs 43 or 44, wherein T cells are analyzed by RNA-seq to determine single cells that are activated and TCRab pairs are identified in the activated T cells.
46. The method of any of paragraphs 42 to 45, wherein the reporter is an inducible fluorescent marker protein, wherein the marker protein is induced when a TCRab pair detects a MHCII epitope.
47. The method of paragraph 46, wherein the fluorescent marker is under control of the IL-2 promoter.
48. The method of any of paragraphs 42 to 47, further comprising administering to the subject a vaccine comprising one or more of the immunodominant epitopes.
49. The method of paragraph 48, wherein the vaccine is a protective vaccine or a tolerizing vaccine.
50. The method of paragraphs 48 or 49, wherein the vaccine comprises autologous dendritic cells or antigen presenting cells pulsed with one or more of the immunodominant epitopes.
51. A method of identifying peptide antigens from a live bacterial pathogen comprising: isolating MHCII-peptide complexes from dendritic cells exposed to a bacterial pathogen; isolating the peptides from the MHCII-peptide complexes; and sequencing the isolated peptides.
52. A peptide set for training a MHCII neural network comprising one or more of SEQ ID NOs: 1-14979.
53. A peptide set for training a MHCII neural network comprising one or more of SEQ ID Nos: 14980-15027.
54. A *Listeria* vaccine comprising one or more peptides selected from the peptides listed in Table 1.
55. The *Listeria* vaccine of paragraph 42, wherein the one or more peptides is derived from lmo0202, lmo2558, lmo2185, or lmo0135.
56. The *Listeria* vaccine of paragraph 43, wherein the one or more *Listeria* peptides is selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT).
57. The *Listeria* vaccine of any of paragraphs 42 to 44, wherein the vaccine comprises autologous dendritic cells or antigen presenting cells pulsed with the one or more peptides.

Various modifications and variations of the described methods, pharmaceutical compositions, and kits of the invention will be apparent to those skilled in the art without departing from the scope and spirit of the invention. Although the invention has been described in connection with specific embodiments, it will be understood that it is capable of further modifications and that the invention as claimed should not be unduly limited to such specific embodiments. Indeed, various modifications of the described modes for carrying out the invention that are obvious to those skilled in the art are intended to be within the scope of the invention. This application is intended to cover any variations, uses, or adaptations of the invention following, in general, the principles of the invention and including such departures from the present disclosure come within known customary practice within the art to which the invention pertains and may be applied to the essential features herein before set forth.

SEQUENCE LISTING

The patent contains a lengthy sequence listing. A copy of the sequence listing is available in electronic form from the USPTO web site (https://seqdata.uspto.gov/?pageRequest=docDetail&DocID=US12374423B2). An electronic copy of the sequence listing will also be available from the USPTO upon request and payment of the fee set forth in 37 CFR 1.19(b)(3).

What is claimed is:

1. A method of identifying one or more immunodominant epitopes, comprising:
   a) generating, using one or more processors, a set of candidate antigens from one or more input genome sequences, wherein the one or more input genome sequences is derived from a target pathogen, a commensal microorganism, or a diseased cell;
   b) generating, using the one or more processors, a ranked set of antigenic epitopes from the candidate antigens using a deep neural network, wherein the deep neural network is trained using a set of MHCII-presented peptides bound to antigen presenting cells, wherein the antigen presenting cells are dendritic cells;
   c) detecting whether one or more of the antigenic epitopes is present in a sample from a subject suffering from an infection, autoimmune disease, allergy, or cancer;
   d) formulating an immunological composition comprising one or more of the identified epitopes; and
   e) identifying one or more immunodominant epitopes by:
      i) administering the immunological composition to a first population of immune cells to allow expression of the one or more identified epitopes, and wherein the first population of immune cells comprise a detectable reporter gene;
      ii) expressing in a second population of CD4+ immune cells a TCRαβ library expressing TCRαβ pairs identified in a subject suffering from an infectious disease, autoimmunity, cancer or allergy;
      ii) incubating the first population of immune cells with the second population of immune cells;
      iv) sorting immune cells positive for the detectable reporter gene; and
      v) identifying peptides bound to MHCII in immune cells positive for the detectable reporter gene, wherein the peptides identified comprise the immunodominant epitopes.

2. The method of claim 1, wherein generating a set of candidate antigens from one or more input genome sequences comprises:
   predicting, by the processor, genes from an input genome sequence; and
   defining, by the processor, a set of candidate antigens from the set of predicted genes based on one or more of protein cellular location, transmembrane structure, and domain distribution, wherein defining, by the processor, a set of candidate antigens from the set of predicted genes, comprises one or more of:

a) selecting surface and secreted proteins;
b) masking intracellular regions and transmembrane domains of the surface and extracellular proteins;
c) excluding regions that are within domains of less than 30 amino acids;
d) excluding regions between a series of inaccessible domains; and
e) excluding inter-domain regions between a series of adjacent domains wherein the inter-domain regions are less than or equal to 20 amino acids.

3. The method of claim 2, further comprising masking up to 20 amino acids flanking the intracellular regions and transmembrane domains, wherein 8 amino acids flanking the intracellular regions and transmembrane domains are masked; and/or
   wherein the surface protein is a cell wall protein; or
   wherein the surface protein is an outer membrane protein.

4. The method of claim 1, wherein the antigenic epitopes are derived from candidate antigens more than 20 amino acids away from a transmembrane domain; and/or
   wherein the candidate antigens comprise a tertiary structure required for proteolytic enzyme accessibility; and/or
   wherein the candidate antigens comprise a defined MHCII-binding motif in the primary amino acid sequence of the predicted genes, such as, the I-Ab-binding motif; and/or
   wherein the antigenic epitopes comprise a tertiary structure required for accessibility to a MHCII binding groove; and/or
   wherein generating, by the processor, a ranked set of antigenic epitopes from the candidate antigens using a deep neural network comprises:
a) encoding each amino acid of an input candidate antigen into a p-dimensional binary vector;
b) converting the binary vector to a descriptor matrix S;
c) convoluting the descriptor matrix S to a scoring matrix X; and
d) transforming the scoring matrix X into a cl-dimensional vector Z, wherein vector Z is input for a neural network; and/or
   wherein the antigenic epitopes are specific for an HLA type; and/or
   wherein the candidate antigens are expressed in the pathogen, commensal microorganism or diseased cell; and/or
   wherein the one or more input genome sequences is obtained by whole genome or whole exome sequencing; and/or
   wherein the antigenic epitopes are about 9 to 20 amino acids in length.

5. The method of claim 1, wherein the method further comprises:
   a) isolating MHCII-peptide complexes from antigen presenting cells, wherein the antigen presenting cells are exposed to a target pathogen, commensal microorganism or diseased cell; wherein the antigen presenting cells are dendritic cells; and/or wherein the antigen presenting cell comprises a subject specific MHCII allele, wherein the antigen presenting cell comprises a human MHCII allele;
   b) identifying bound peptides from the MHCII-peptide complexes; and
   c) training the deep neural network using the set of identified peptides.

6. The method of claim 1, wherein the pathogen is selected from the group consisting of a bacterium, a virus, a protozoan, and an allergen, wherein the pathogen comprises a bacteria belonging to a family selected from the group consisting of *Bacillus*, *Bartonella*, *Bordetella*, *Borrelia*, *Brucella*, *Campylobacter*, *Chlamydia* and *Chlamydophila*, *Clostridium*, *Corynebacterium*, *Enterococcus*, *Escherichia*, *Francisella*, *Haemophilus*, *Helicobacter*, *Legionella*, *Leptospira*, *Listeria*, *Mycobacterium*, *Mycoplasma*, *Neisseria*, *Pseudomonas*, *Rickettsia*, *Salmonella*, *Shigella*, *Staphylococcus*, *Streptococcus*, *Treponema*, *Ureaplasma*, *Vibrio*, and *Yersinia*; or
   wherein the diseased cell is a cancer cell, wherein the cancer cell is obtained from a subject; or
   wherein the diseased cell is associated with an autoimmune disease; or
   wherein the commensal microorganism comprises a bacterium belonging to a genus selected from the group consisting of *Bacteroides*, *Clostridium*, *Faecalibacterium*, *Eubacterium*, *Ruminococcus*, *Peptococcus*, *Peptostreptococcus*, *Bifidobacterium*, *Lactobacillus* and *Akkermansia*; or a fungus selected from the group consisting of *Candida*, *Saccharomyces*, *Aspergillus*, *Penicillium*, *Rhodotorula*, *Trametes*, *Pleospora*, *Sclerotinia*, *Bullera*, and *Galactomyces*.

7. The method of claim 6, further comprising identifying non-silent tumor specific somatic mutations from the subject specific cancer cell, wherein the ranked set of antigenic epitopes are generated from said mutations.

8. The method of claim 1, wherein the deep neural network is trained using a set of MHCII-presented peptides comprising one or more of SEQ ID NOs: 1-14979; or
   wherein the deep neural network is trained using a set of MHCII-presented peptides comprising one or more of SEQ ID NOs: 14980-15027.

9. The method of claim 1, wherein the immunological composition is a protective vaccine or tolerizing vaccine composition comprising one or more of the antigenic epitopes,
   wherein the vaccine composition comprises autologous dendritic cells or antigen presenting cells pulsed with the one or more epitopes; or
      wherein the vaccine composition is directed to a bacterium, a virus or a protozoan; or
      wherein the vaccine composition is directed to a cancer; or
      wherein the vaccine composition is directed to an autoimmune disease or allergy, whereby administration of the vaccine induces tolerance to the one or more antigenic epitopes.

10. The method of claim 9, wherein the vaccine composition is directed to *Listeria*.

11. The method of claim 10, wherein the one or more *Listeria* peptides are derived from lmo0202, lmo2558, lmo2185, or lmo0135.

12. The method of claim 10, wherein the one or more *Listeria* peptides are selected from the group consisting of SEQ ID NO: 14981 (WNEKYAQAYPNVSAKI), SEQ ID NO: 14984 (APGQETQHYYGLPVADSAIDR), SEQ ID NO: 14986 (ADFRYVFDTAKATAASSYPG), and SEQ ID NO: 14997 (VDDTTVKFTLPTVAPAFENT).

13. The method of claim 1, wherein the method comprises determining immune related health status in a subject comprising:
   a) exposing the immunological composition comprising one or more peptides to immune cells obtained from the subject; and
   b) measuring cytokine secretion, wherein the cytokines measured comprise IL-2, IFN-y, IL-17, and/or IL-10.

14. The method of claim 13, further comprising measuring immune cell types reactive to the epitopes in the subject,
   wherein the immune cell types comprise Treg, Th1, Th17 and/or Th2 cells; and/or
   wherein the immune cells are measured using MHCII tetramers.

15. The method of claim 1, wherein the method comprises determining immune related health status in a subject comprising:
   measuring immune cell types reactive to the immunological composition comprising one or more of the identified epitopes in the subject,
   wherein the immune cell types comprise Treg, Th1, Th17 and/or Th2 cells; and/or
   wherein the immune cells are measured using MHCII tetramers.

16. The method of claim 1, wherein the TCRαβ pairs are identified by T cell profiling,
   wherein TCRαβ pairs are determined by targeted single cell RNA-seq (TCRseq); or
   wherein T cells are analyzed by RNA-seq to determine single cells having a specific cell state and TCRαβ pairs are identified in the T cells having a specific cell state, wherein the specific cell state is a pathogenic phenotype or a protective phenotype.

17. The method of claim 1, wherein the reporter is an inducible fluorescent marker protein, wherein the marker protein is induced when a TCRαβ pair detects an MHCII epitope, wherein the fluorescent marker is under control of the IL-2 promoter.

18. The method of claim 1, further comprising formulating a vaccine composition comprising one or more of the immunodominant epitopes,
   wherein the vaccine is a protective vaccine or a tolerizing vaccine; or
   wherein the vaccine comprises autologous dendritic cells or antigen presenting cells pulsed with one or more of the immunodominant epitopes.

* * * * *